(12) United States Patent
Chang et al.

(10) Patent No.: US 12,201,613 B2
(45) Date of Patent: Jan. 21, 2025

(54) BIOSENSING PLATFORM FOR DETECTING VIRAL INFECTIONS AND METHODS FOR SCREENING A MODULATOR OF VIRAL INFECTIONS AND PROTECTING THEREFROM

(71) Applicant: PIN JYE BIO TECH CO., LTD., Taipei (TW)

(72) Inventors: Chia-Ching Chang, Hsinchu (TW); Dar-Bin Shieh, Hsinchu (TW); Chia-Yu Chang, Hsinchu (TW); Lik Voon Kiew, Hsinchu (TW); Choon-Han Heh, Hsinchu (TW); Bey-Fen Leo, Hsinchu (TW); Lip-Yong Chung, Hsinchu (TW)

(73) Assignee: PIN JYE BIO TECH CO., LTD., Taipei (TW)

( * ) Notice: Subject to any disclaimer, the term of this patent is extended or adjusted under 35 U.S.C. 154(b) by 743 days.

(21) Appl. No.: 17/505,693

(22) Filed: Oct. 20, 2021

(65) Prior Publication Data

US 2022/0117936 A1 Apr. 21, 2022

Related U.S. Application Data

(60) Provisional application No. 63/094,403, filed on Oct. 21, 2020.

(51) Int. Cl.
*G01N 27/02* (2006.01)
*A61K 31/401* (2006.01)
(Continued)

(52) U.S. Cl.
CPC .......... *A61K 31/404* (2013.01); *A61K 31/401* (2013.01); *G01N 27/026* (2013.01); *G01N 27/3272* (2013.01)

(58) Field of Classification Search
CPC .... A61K 31/401; A61K 31/404; C12Q 1/005; C12Q 1/00; C12Q 1/02; C12Q 1/006;
(Continued)

(56) References Cited

PUBLICATIONS

Herenda et al., Int. J. Electrochem. Sci., 2019, 10130-10138 (Year: 2019).*

(Continued)

*Primary Examiner* — Gurpreet Kaur
(74) *Attorney, Agent, or Firm* — Amin, Turocy & Watson, LLP

(57) ABSTRACT

Provided is a method for screening a modulator of a viral infection by detecting an interaction of angiotensin converting enzyme 2 (ACE2) and a spike protein with a biosensing platform. Also provided is a compound of formula (I) as a modulator of a viral infection, where R, X, A, $R_3$ to $R_5$, and m are as defined herein, and a method for protecting a subject from a viral infection by administering with the compound.

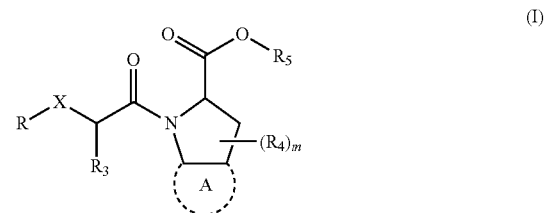

20 Claims, 46 Drawing Sheets
Specification includes a Sequence Listing.

(51) Int. Cl.
*A61K 31/404* (2006.01)
*G01N 27/327* (2006.01)

(58) Field of Classification Search
CPC ... C12Q 1/34; C12Q 1/54; C12Q 1/18; G01N 2333/165; G01N 27/3272; G01N 27/327; G01N 27/3275; G01N 27/3276; G01N 27/4875; G01N 33/56983
See application file for complete search history.

(56) References Cited

PUBLICATIONS

Kiew, et al. "Development of flexible electrochemical impedance spectroscopy-based biosensing platform for rapid screening of SARS-CoV-2 inhibitors", Elsevier Biosensors and Bioelectronics 183, Apr. 3, 2021.

Huang, et al. "Stability of SARS-CoV-2 Spike G614 Variant Surpasses That of the D614 Variant after Cold Storage", American Society for Microbiology mSphere, vol. 6, Issue 2, Mar. 31, 2021.

* cited by examiner

MLN-4760

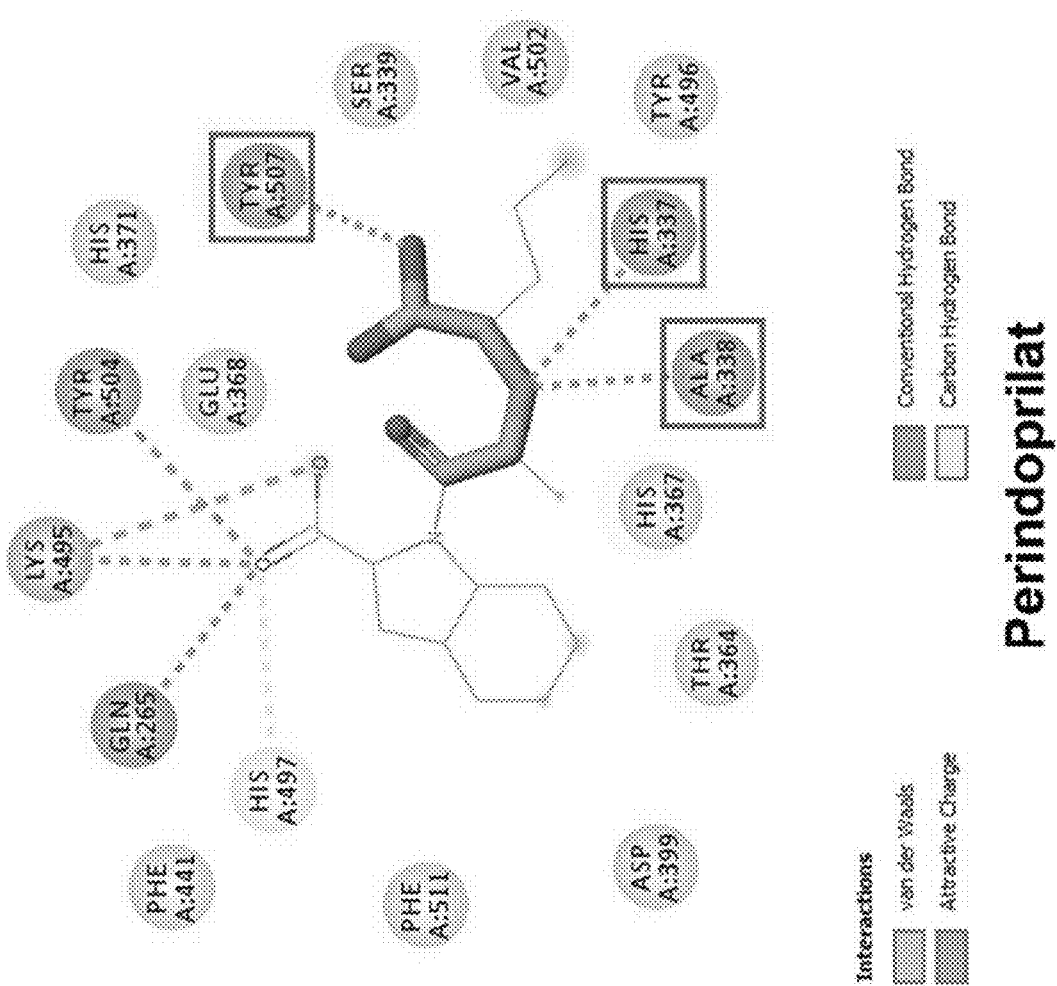
FIG. 3C Perindoprilat

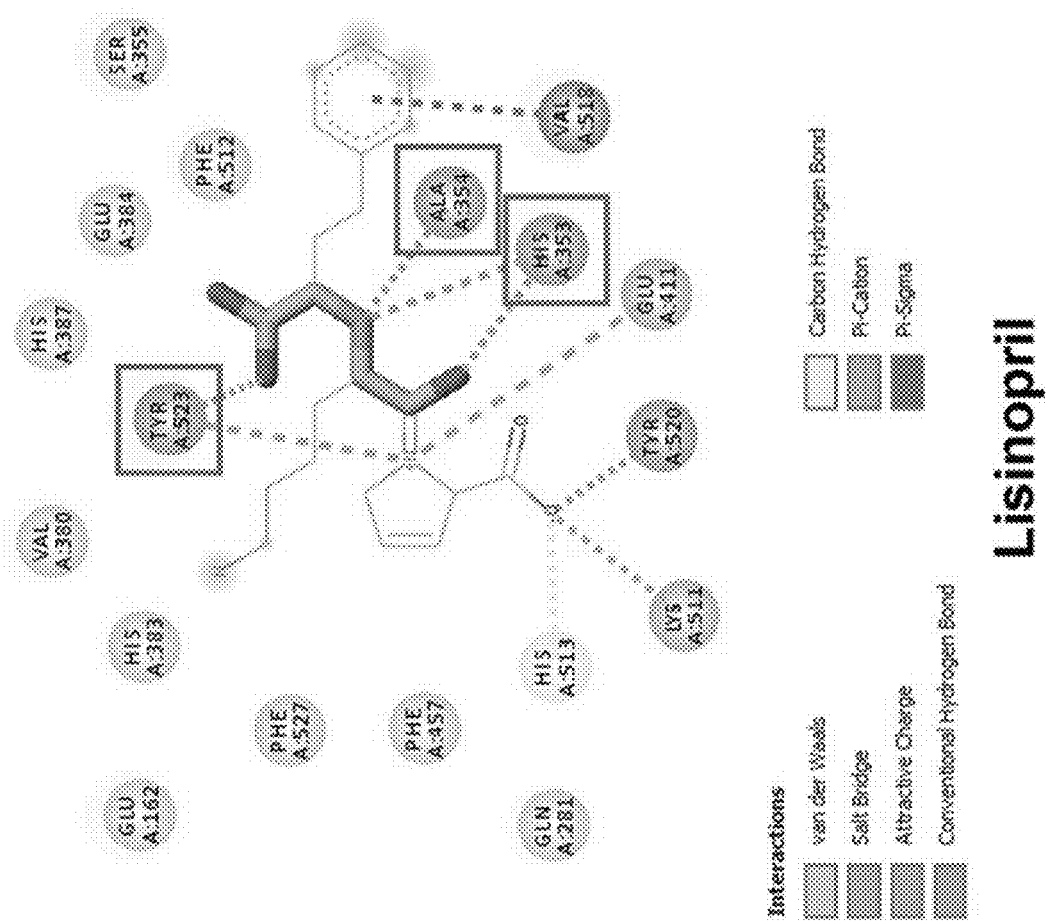
FIG. 3D Lisinopril

SEQUENCE LISTING

```
<160> NUMBER OF SEQ ID NOS: 5

<210> SEQ ID NO 1
<211> LENGTH: 805
<212> TYPE: PRT
<213> ORGANISM: Artificial Sequence
<220> FEATURE:
<223> OTHER INFORMATION: ACE2

<400> SEQUENCE: 1

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
```

```
            115                 120                 125
Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
145                 150                 155                 160

Arg Leu Trp Ala Trp Glu Ser Trp Arg Ser Glu Val Gly Lys Gln Leu
                    165                 170                 175

Arg Pro Leu Tyr Glu Glu Tyr Val Val Leu Lys Asn Glu Met Ala Arg
                180                 185                 190

Ala Asn His Tyr Glu Asp Tyr Gly Asp Tyr Trp Arg Gly Asp Tyr Glu
            195                 200                 205

Val Asn Gly Val Asp Gly Tyr Asp Tyr Ser Arg Gly Gln Leu Ile Glu
        210                 215                 220

Asp Val Glu His Thr Phe Glu Glu Ile Lys Pro Leu Tyr Glu His Leu
225                 230                 235                 240

His Ala Tyr Val Arg Ala Lys Leu Met Asn Ala Tyr Pro Ser Tyr Ile
                    245                 250                 255

Ser Pro Ile Gly Cys Leu Pro Ala His Leu Leu Gly Asp Met Trp Gly
                260                 265                 270

Arg Phe Trp Thr Asn Leu Tyr Ser Leu Thr Val Pro Phe Gly Gln Lys
                275                 280                 285

Pro Asn Ile Asp Val Thr Asp Ala Met Val Asp Gln Ala Trp Asp Ala
290                 295                 300

Gln Arg Ile Phe Lys Glu Ala Glu Lys Phe Phe Val Ser Val Gly Leu
305                 310                 315                 320

Pro Asn Met Thr Gln Gly Phe Trp Glu Asn Ser Met Leu Thr Asp Pro
                    325                 330                 335

Gly Asn Val Gln Lys Ala Val Cys His Pro Thr Ala Trp Asp Leu Gly
                340                 345                 350

Lys Gly Asp Phe Arg Ile Leu Met Cys Thr Lys Val Thr Met Asp Asp
                355                 360                 365

Phe Leu Thr Ala His His Glu Met Gly His Ile Gln Tyr Asp Met Ala
    370                 375                 380

Tyr Ala Ala Gln Pro Phe Leu Leu Arg Asn Gly Ala Asn Glu Gly Phe
385                 390                 395                 400

His Glu Ala Val Gly Glu Ile Met Ser Leu Ser Ala Ala Thr Pro Lys
                    405                 410                 415

His Leu Lys Ser Ile Gly Leu Leu Ser Pro Asp Phe Gln Glu Asp Asn
                420                 425                 430

Glu Thr Glu Ile Asn Phe Leu Leu Lys Gln Ala Leu Thr Ile Val Gly
            435                 440                 445

Thr Leu Pro Phe Thr Tyr Met Leu Glu Lys Trp Arg Trp Met Val Phe
        450                 455                 460

Lys Gly Glu Ile Pro Lys Asp Gln Trp Met Lys Lys Trp Trp Glu Met
465                 470                 475                 480

Lys Arg Glu Ile Val Gly Val Val Glu Pro Val Pro His Asp Glu Thr
                    485                 490                 495

Tyr Cys Asp Pro Ala Ser Leu Phe His Val Ser Asn Asp Tyr Ser Phe
                500                 505                 510

Ile Arg Tyr Tyr Thr Arg Thr Leu Tyr Gln Phe Gln Phe Gln Glu Ala
                515                 520                 525

Leu Cys Gln Ala Ala Lys His Glu Gly Pro Leu His Lys Cys Asp Ile
530                 535                 540
```

-continued

Ser Asn Ser Thr Glu Ala Gly Gln Lys Leu Phe Asn Met Leu Arg Leu
545                 550                 555                 560

Gly Lys Ser Glu Pro Trp Thr Leu Ala Leu Glu Asn Val Val Gly Ala
                565                 570                 575

Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Gln Ser Ile Lys Val Arg Ile Ser Leu
    610                 615                 620

Lys Ser Ala Leu Gly Asp Arg Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
                660                 665                 670

Ala Asn Leu Lys Pro Arg Ile Ser Phe Asn Phe Val Thr Ala Pro
            675                 680                 685

Lys Asn Val Ser Asp Ile Ile Pro Arg Thr Glu Val Glu Lys Ala Ile
            690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735

Pro Pro Val Ser Ile Trp Leu Ile Val Phe Gly Val Val Met Gly Val
                740                 745                 750

Ile Val Val Gly Ile Val Ile Leu Ile Phe Thr Gly Ile Arg Asp Arg
                755                 760                 765

Lys Lys Lys Asn Lys Ala Arg Ser Gly Glu Asn Pro Tyr Ala Ser Ile
        770                 775                 780

Asp Ile Ser Lys Gly Glu Asn Asn Pro Gly Phe Gln Asn Thr Asp Asp
785                 790                 795                 800

Val Gln Thr Ser Phe
            805

<210> SEQ ID NO 2
<211> LENGTH: 287
<212> TYPE: PRT
<213> ORGANISM: Artificial Sequence
<220> FEATURE:
<223> OTHER INFORMATION: S protein

<400> SEQUENCE: 2

Met Arg Cys Glu Ile Pro His Arg Cys Val Arg Lys Tyr Arg Ile
1               5                   10                  15

Arg Arg His Ser Pro Phe Arg Leu Arg Asn Cys Trp Glu Gly Arg Ser
            20                  25                  30

Val Arg Ala Ser Ser Leu Leu Arg Gln Leu Ala Lys Gly Gly Cys Ala
        35                  40                  45

Ala Arg Arg Leu Ser Trp Val Thr Pro Gly Phe Ser Gln Ser Arg Arg
    50                  55                  60

Cys Lys Thr Thr Ala Ser Glu Phe Glu Leu Gly Thr Ser Arg Met His
65                  70                  75                  80

Leu Asp Met Glu Lys Gly Ile Tyr Gln Thr Ser Asn Phe Arg Val Gln
                85                  90                  95

Pro Thr Glu Ser Ile Val Arg Phe Pro Asn Ile Thr Asn Leu Cys Pro
            100                 105                 110

Phe Gly Glu Val Phe Asn Ala Thr Arg Phe Ala Ser Val Tyr Ala Trp
            115                 120                 125

Asn Arg Lys Arg Ile Ser Asn Cys Val Ala Asp Tyr Ser Val Leu Tyr
            130                 135                 140

Asn Ser Ala Ser Phe Ser Thr Phe Lys Cys Tyr Gly Val Ser Pro Thr
145                 150                 155                 160

Lys Leu Asn Asp Leu Cys Phe Thr Asn Val Tyr Ala Asp Ser Phe Val
                165                 170                 175

Ile Arg Gly Asp Glu Val Arg Gln Ile Ala Pro Gly Gln Thr Gly Lys
            180                 185                 190

Ile Ala Asp Tyr Asn Tyr Lys Leu Pro Asp Asp Phe Thr Gly Cys Val
            195                 200                 205

Ile Ala Trp Asn Ser Asn Asn Leu Asp Ser Lys Val Gly Gly Asn Tyr
            210                 215                 220

Asn Tyr Leu Tyr Arg Leu Phe Arg Lys Ser Asn Leu Lys Pro Phe Glu
225                 230                 235                 240

Arg Asp Ile Ser Thr Glu Ile Tyr Gln Ala Gly Ser Thr Pro Cys Asn
                245                 250                 255

Gly Val Glu Gly Phe Asn Cys Tyr Phe Pro Leu Gln Ser Tyr Gly Phe
            260                 265                 270

Gln Pro Thr Asn Gly Val Gly Tyr Gln Pro Tyr Arg Val Val Val
            275                 280                 285

<210> SEQ ID NO 3
<211> LENGTH: 26
<212> TYPE: DNA
<213> ORGANISM: Artificial Sequence
<220> FEATURE:
<223> OTHER INFORMATION: Primer Forward

<400> SEQUENCE: 3
acaggtacgt taatagttaa tagcgt                                          26

<210> SEQ ID NO 4
<211> LENGTH: 22
<212> TYPE: DNA
<213> ORGANISM: Artificial Sequence
<220> FEATURE:
<223> OTHER INFORMATION: Primer Reverse

<400> SEQUENCE: 4
atattgcagc agtacgcaca ca                                              22

<210> SEQ ID NO 5
<211> LENGTH: 26
<212> TYPE: DNA
<213> ORGANISM: Artificial Sequence
<220> FEATURE:
<223> OTHER INFORMATION: Probe

<400> SEQUENCE: 5
acactagcca tccttactgc gcttcg                                          26

BIOSENSING PLATFORM FOR DETECTING VIRAL INFECTIONS AND METHODS FOR SCREENING A MODULATOR OF VIRAL INFECTIONS AND PROTECTING THEREFROM

BACKGROUND

1. Technical Field

The present disclosure relates to the field of antiviral therapy, and, in particular, to biosensing platforms for detecting viral infections and screening modulators of viral infections, and methods for preventing or treating viral infections.

2. Description of Related Art

Epidemics caused by coronaviruses (CoVs), e.g., severe acute respiratory syndrome (SARS) in 2003, Middle East respiratory syndrome (MERS) in 2012, and coronavirus disease 2019 (COVID-19) in 2019, have triggered a global public health emergency. For example, SARS-CoV-2 (i.e., virus of COVID-19) has infected more than 21 million people and caused over 755,000 deaths worldwide. It is conceivable that COVID-19 infection may continue into the foreseeable future even with the availability of vaccines and other therapeutics.

The structural proteins of CoVs include nucleocapsid (N), small envelope (E), matrix (M) and trimeric spike (S) glycoproteins, which are essential for virion assembly and function to complete the viral life cycle during infections. Numerous studies have suggested that SARS-CoV-2 enters human cells, in particular the type II alveolar (AT2) cells, through interaction with the cell surface angiotensin converting enzyme 2 (ACE2) via its spike (S)-protein[1-3]. However, this also raises the concern that the pharmacological inducers of ACE2 expression, such as angiotensin converting enzyme inhibitors (ACEi) that are commonly prescribed for the management of cardiovascular diseases and hypertension, may increase the infection risk or exacerbate the severity of SARS-CoV-2 infection in this patient population[4, 5].

Hence, there exists an unmet need to identify competent compounds that have potential to effectively treat coronavirus infections.

SUMMARY

In view of the foregoing, the present disclosure provides a biosensing platform for screening a modulator that is capable of modulating a protein-protein interaction between coronavirus S-protein and ACE2 on the host cell surface, thereby protecting a subject from a viral infection.

In at least one embodiment of the present disclosure, the modulator is a compound represented by formula (I) below:

(I)

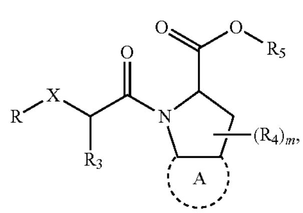

wherein:

A is absent or a 4- to 6-membered ring optionally substituted with 1 to 5 moieties of deuterium, halo, amino, hydroxyl, $C_{1-6}$ alkyl, or $C_{1-6}$ alkoxy;

X is NH or $CH_2$;

R is —SH or —$CHR_2C(=O)OR_1$;

$R_1$ is H, deuterium, or a substituted or unsubstituted moiety selected from the group consisting of $C_{1-6}$ alkyl, $C_{3-10}$ cycloalkyl, $C_{3-10}$ cycloheteroalkyl, $C_{6-10}$ aryl, and $C_{4-10}$ heteroaryl;

$R_2$ is a substituted or unsubstituted moiety selected from the group consisting of $C_{1-6}$ alkyl, $C_{2-6}$ alkenyl, $C_{2-6}$ alkynyl, $C_{1-6}$ alkoxy, $C_{2-6}$ alkenyloxy, $C_{1-6}$ alkylcarbonyl, $C_{1-6}$ alkyloxycarbonyl, $C_{1-6}$ alkylamino, $C_{3-20}$ cycloalkyl, $C_{3-20}$ cycloheteroalkyl, $C_{6-20}$ aryl, and $C_{4-20}$ heteroaryl;

$R_3$ is H, deuterium, halo, cyano, hydroxyl, carboxyl, amino, formyl, nitro, or a substituted or unsubstituted moiety selected from the group consisting of $C_{1-6}$ alkyl, $C_{2-6}$ alkenyl, $C_{2-6}$ alkynyl, $C_{1-6}$ alkoxy, $C_{2-6}$ alkenyloxy, $C_{1-6}$ alkylcarbonyl, $C_{1-6}$ alkyloxycarbonyl, $C_{1-6}$ alkylamino, $C_{3-20}$ cycloalkyl, $C_{3-20}$ cycloheteroalkyl, $C_{6-20}$ aryl, and $C_{4-20}$ heteroaryl;

$R_4$ is H, deuterium, amino, halo, hydroxyl, or a substituted or unsubstituted moiety selected from the group consisting of $C_{1-6}$ alkyl and $C_{1-6}$ alkoxy;

$R_5$ is H, deuterium, or a substituted or unsubstituted $C_{1-6}$ alkyl; and m is an integer of 1 to 4.

In at least one embodiment of the present disclosure, the modulator is a compound represented by formula (II) below:

(II)

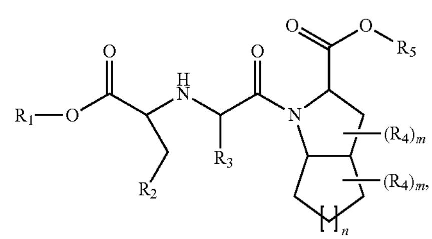

wherein $R_1$ to $R_5$ and m are defined as above, and n is 0, 1 or 2.

In at least one embodiment of the present disclosure, the modulator is a compound represented by formula (III) below:

(III)

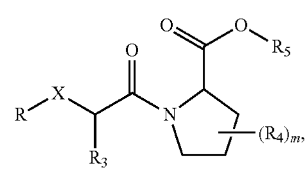

wherein R, X, $R_3$ to $R_5$ and m are defined as above.

In at least one embodiment of the present disclosure, the substituted moiety in the compound of formula (I), (II) or (III) is substituted by one or more substituents selected from the group consisting of deuterium, alkyl, alkenyl, alkynyl, hydroxyalkyl, fluoroalkyl, chloroalkyl, bromoalkyl, iodoalkyl, perfluoroalkyl, aryl, heteroaryl, cycloalkyl, cycloalkenyl, cycloheteroalkyl, carboxyl, aralkyl, aralkenyl, aralkynyl, heteroaralkyl, heteroaralkenyl, heteroaralkynyl, heterocyclyl, acyl, aminocarbonyl, aminoalkyl, amino, alkylamino, hydroxyl, alkoxy, aryloxy, silyloxy, amido, imidoyl, carbamoyl, halo, cyano, nitro, phosphate group, thio, thioether, sulfo, and sulfamido. In some embodiments, the substituted moiety consists of the moiety and at least one substituent (e.g., 1 to 5 substituents) as mentioned above.

In at least one embodiment of the present disclosure, in the compound of formula (I), (II) or (III), $R_1$ is H or $C_{1-6}$ alkyl optionally substituted with 1 to 5 moieties of deuterium, halo, amino, hydroxyl, $C_{1-6}$ alkyl, or $C_{1-6}$ alkoxy. In some embodiments of the present disclosure, $R_1$ may be H, methyl, ethyl, or propyl.

In at least one embodiment of the present disclosure, in the compound of formula (I), (II) or (III), $R_2$ is $C_{1-6}$ alkyl, $C_{1-6}$ alkoxy, $C_{1-6}$ alkylamino, $C_{3-20}$ cycloalkyl, $C_{3-20}$ cycloheteroalkyl, $C_{6-20}$ aryl, or $C_{4-20}$ heteroaryl, and is optionally substituted with one or more substituents selected from the group consisting of deuterium, halo, amino, hydroxyl, $C_{1-6}$ alkyl, $C_{1-6}$ alkoxy, $C_{3-10}$ cycloalkyl, $C_{3-10}$ cycloheteroalkyl, $C_{6-10}$ aryl, and $C_{4-10}$ heteroaryl. In some embodiments of the present disclosure, $R_2$ is $C_{1-6}$ alkyl optionally substituted with 1 to 5 moieties of $C_{1-6}$ alkyl, $C_{3-10}$ cycloalkyl, $C_{3-10}$ cycloheteroalkyl, $C_{6-10}$ aryl, or $C_{4-10}$ heteroaryl. In some embodiments of the present disclosure, $R_2$ may be methyl, ethyl, propyl, or benzyl.

In at least one embodiment of the present disclosure, in the compound of formula (I), (II) or (III), $R_3$ is $C_{1-6}$ alkyl, $C_{2-6}$ alkenyl, $C_{2-6}$ alkynyl, $C_{1-6}$ alkoxy, $C_{2-6}$ alkenyloxy, $C_{1-6}$ alkylcarbonyl, $C_{1-6}$ alkyloxycarbonyl, or $C_{1-6}$ alkylamino, and is optionally substituted with one or more substituents selected from the group consisting of deuterium, halo, hydroxyl, cyano, amino, nitro, carboxyl, $C_{1-6}$ alkyl, $C_{1-6}$ alkoxy, and $C_{1-6}$ alkylamino. In some embodiments of the present disclosure, $R_3$ is $C_{1-6}$ alkyl optionally substituted with 1 to 5 moieties of deuterium, halo, hydroxyl, cyano, amino, nitro, carboxyl, $C_{1-6}$ alkyl, $C_{1-6}$ alkoxy, or $C_{1-6}$ alkylamino. In some embodiments of the present disclosure, $R_3$ may be methyl, ethyl, propyl, n-butyl, or n-butylamine.

In at least one embodiment of the present disclosure, in the compound of formula (I), (II) or (III), $R_4$ is H, halo, $C_{1-6}$ alkyl or $C_{1-6}$ alkoxy, wherein $C_{1-6}$ alkyl or $C_{1-6}$ alkoxy is optionally substituted with 1 to 5 moieties of deuterium, halo or hydroxyl. In some embodiments of the present disclosure, $R_4$ is H, deuterium, amino, halo, or hydroxyl.

In at least one embodiment of the present disclosure, in the compound of formula (I), (II) or (III), $R_5$ is H or $C_{1-6}$ alkyl optionally substituted with 1 to 5 moieties of deuterium, halo, amino, hydroxyl, $C_{1-6}$ alkyl, or $C_{1-6}$ alkoxy. In some embodiments of the present disclosure, $R_4$ and $R_5$ are H.

In at least one embodiment of the present disclosure, the modulator is an angiotensin-converting enzyme (ACE, also known as ACE1) inhibitor. In some embodiments of the present disclosure, the modulator is selected from the group consisting of perindopril, perindoprilat, ramipril, ramiprilat, enalapril, enalaprilat, lisinopril, and captopril.

In at least one embodiment of the present disclosure, the compound of formula (II) is selected from the group consisting of:

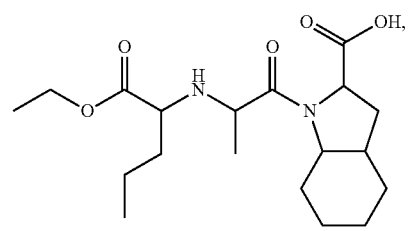

perindopril

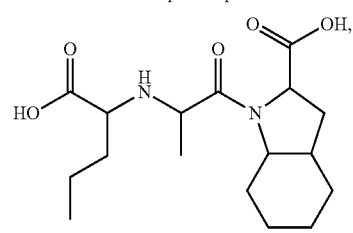

perindoprilat

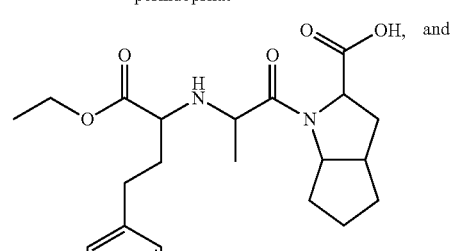

ramipril

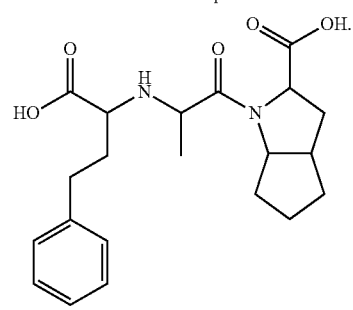

ramiprilat

In at least one embodiment of the present disclosure, the compound of formula (III) is selected from the group consisting of:

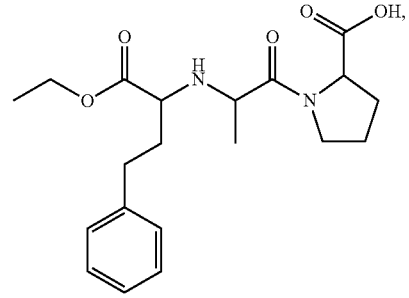

enalapril

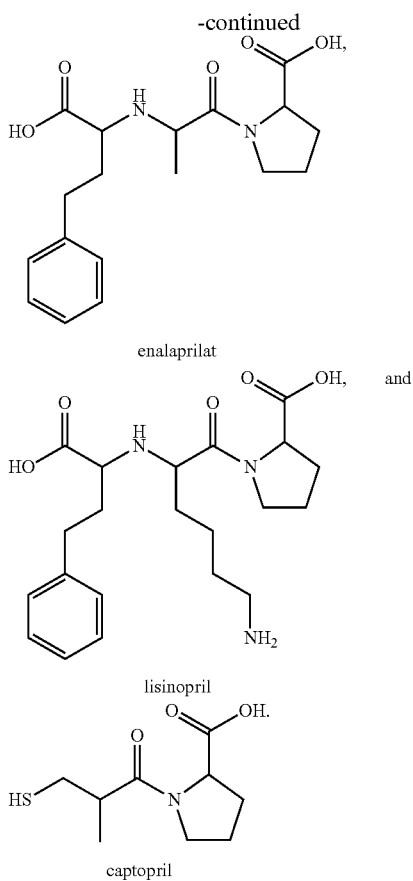

enalaprilat lisinopril captopril

In at least one embodiment of the present disclosure, a method for protecting a subject from a viral infection is provided. The method comprises administering to the subject an effective amount of at least one of the above-mentioned modulators.

In at least one embodiment of the present disclosure, the viral infection is caused by a coronavirus. In some embodiments, the coronavirus is SARS-CoV, MERS-CoV, SARS-CoV-2, mouse hepatitis virus (MHV), porcine epidemic diarrhea virus (PEDV), or a variant thereof. In some embodiments, the coronavirus may be a variant of SARS-CoV-2, such as a D614G mutant strain, a B.1.1.7 (alpha) mutant strain, a B.1.351 (beta) mutant strain, a P1 mutant strain, and a B.1.617.2 (delta) mutant strain, but not limited thereto.

In at least one embodiment of the present disclosure, the compound of formula (II) is administered to the subject for inhibiting infectivity of the virus in the subject. In some embodiments of the present disclosure, the compound of formula (II) is formulated into an antiviral medicine for administration.

In at least one embodiment of the present disclosure, the compound of formula (III) is administered to the subject for inducing an immune response against the virus in the subject. In some embodiments of the present disclosure, the compound of formula (III) is formulated into a vaccine composition for administration. In some embodiments of the present disclosure, the compound of formula (III) severs as an adjuvant in the vaccine composition against the virus.

In at least one embodiment of the present disclosure, a method for preventing, treating, or reducing a risk of a viral infection in a subject in need thereof is provided. The method comprises administering to the subject an effective amount of at least one of the above-mentioned compounds. In another embodiment of the present disclosure, the method comprises administering the compound of formula (II) to the subject.

In at least one embodiment of the present disclosure, the subject is taking or has taken a medication for the management of hypertension or a cardiovascular disease, and/or at a risk of developing the viral infection. In some embodiments of the present disclosure, the medication for the management of hypertension or a cardiovascular disease may be enalapril, enalaprilat, lisinopril, or captopril. In some embodiments of the present disclosure, the subject suffers from hypertension or a cardiovascular disease.

In at least one embodiment of the present disclosure, the modulator is administered orally, intraperitoneally, intravenously, intradermally, intramuscularly, subcutaneously, or transdermally.

In at least one embodiment of the present disclosure, the biosensing platform comprises an insulating support, a working electrode formed from an electrically conductive layer deposited on a surface of the insulating support, and ACE2 coated on the working electrode.

In at least one embodiment of the present disclosure, the electrically conductive layer is composed of palladium, platinum, gold, ruthenium, silver, copper, nickel, indium tin oxide (ITO) or any combination thereof.

In at least one embodiment of the present disclosure, the insulating support is composed of polyethylene terephthalate (PET), polyethersulfone (PES), polyacrylate (PA), polyetherimide (PEI), polyethylene naphthalate (PEN), polyphenylene sulfide (PPS), polyarylate (PAR), polyimide (PI), polycarbonate (PC), cellulose triacetate (TAC), cellulose acetate propionate (CAP), or any combination thereof.

In at least one embodiment of the present disclosure, a method for screening a modulator of a viral infection is provided. The method comprises providing the above-mentioned biosensing platform, pretreating the working electrode of the biosensing platform with a modulator candidate, contacting the working electrode with S-protein or a fragment thereof from the virus in the absence or presence of the modulator candidate, and measuring a level of electrochemical impedance of the working electrode, wherein a difference in the level of the electrochemical impedance of the working electrode pretreated with the modulator candidate compared to a reference level (e.g., pretreated without a modulator) indicates the modulator candidate as the modulator capable of altering an interaction of ACE2 and the S-protein or a variant thereof, thereby modulating the viral infection.

In at least one embodiment of the present disclosure, the fragment of the S-protein is a receptor binding domain of the S-protein.

In at least one embodiment of the present disclosure, the modulator may be the compound represented by formula (I) as mentioned above. In some embodiments of the present disclosure, the modulator may be an ACE inhibitor.

In at least one embodiment of the present disclosure, the biosensing platform provided herein may be used in a method for detecting a viral infection in a subject in need thereof. The method comprises providing a biological sample from the subject, contacting the working electrode of the biosensing platform with the biological sample, and measuring a level of electrochemical impedance of the working electrode, wherein a difference in the level of the electrochemical impedance of the working electrode compared to a control (or a reference level) indicates the presence of the virus in the biological sample.

In at least one embodiment of the present disclosure, the biosensing platform provided herein may further comprise the compound represented by formula (III) as mentioned above, which binds to the ACE2 on the working electrode and improves the binding of the ACE2 to the S-protein of the virus.

In some embodiments of the present disclosure, the biosensing platform provided herein comprises an insulating support, a working electrode formed from an electrically conductive layer deposited on a surface of the insulating support, ACE2 coated on the working electrode, and a sensitivity enhancer binding to the ACE2 on the working electrode. In some embodiments of the present disclosure, the sensitivity enhancer is enalapril, enalaprilat, lisinopril, captopril, or any combination thereof.

In the present disclosure, the modulator screened by the method provided in the present disclosure as an antivirus agent may inhibit the entry of a virus into a host cell and thus reduce the infection risk or the severity of virus infection. Also, the modulator as an adjuvant may improve the immunogenicity of a vaccine composition, such as those comprising virus-like particles, and thus raise or induce an immune response against the virus in the host. Additionally, the modulator as a sensitivity enhancer may improve the interaction between coronavirus S-protein and ACE2, and thus enhance the sensitivity of the biosensing platform for detecting the presence of a virus of interest. The present disclosure further provides an alternative strategy for the treatment of hypertension or a cardiovascular disease, which protects patients from increasing viral infection risk and thus meets safety and treatment requirements for such patient population. Hence, the present disclosure is useful in accelerating the development of anti-coronavirus drugs and controlling the outbreak of coronavirus.

BRIEF DESCRIPTION OF THE DRAWINGS

The present disclosure can be more fully understood by reading the following descriptions of the embodiments, with reference made to the accompanying drawings.

FIGS. 3A to 3F show two dimensional interactions diagrams of ACE2 inhibitor (MLN-4760, FIG. 3A) and ACE inhibitors (enalaprilat, perindoprilat, lisinopril, captopril, and ramiprilat, FIGS. 3B to 3F) with the amino acid residues at the corresponding binding pockets. The amino acid residues that interact with the acetone-glycine moiety at the binding site are highlighted in red boxes.

FIG. 6C demonstrates S-protein concentration-dependent elevation in the intensity of the color dots (reflecting increase S-protein-ACE2 interactions) in image form and quantified-intensity form. AU: arbitrary unit.

FIG. 7A demonstrates the X-ray diffractometer (XRD) spectra of Pd-NTF covered with indium tin oxide ITO (upper panel) and after removal of ITO (lower panel). The black lines denote the noise reduction XRD spectra. The red dash lines denote the Gaussian fitting peaks of Pd (111) or Pd (200). FIG. 7B demonstrates time-dependent ACE2 bio-conjugation. FIG. 7C demonstrates Raman spectra of ACE2 on Pd-NTF (black line) and Pd-NTF only (red line). The black arrows denote the vibration mode of Pd—S bonding. The red asterisks denote the typical polyethylene terephthalate (PET) signal, and S—S denotes the vibration mode of protein disulfide bonds. The A regions represent the protein specific signals.

FIGS. 8A to 8C show the characterization of ACE2-Pd-NTF electrode. FIG. 8A shows the Nyquist plots of the binding of SARS-CoV-2 pseudovirus (expressed in relative infection unit, RIU) to the ACE2-Pd-NTF electrode. The concentrations of SARS-CoV-2 pseudovirus increases from 0 (black squares), 158 (red circles), 316 (cyan triangles), 1,263 (pink inverted triangles) to 2,526 RIU (deep green diamonds). FIG. 8B shows escalating impedance reading ($dR_{ct}$) collected by the EIS-biosensing platform upon exposure to the ascending concentration of SARS-CoV-2 pseudo virus. FIG. 8C shows dose-response curve representing the concentration-dependent interaction of S-protein with the ACE2 (base-D-RC, $EC_{50\ S\text{-}protein\ @baseline}$=1.75±0.34 μM, generated via the biosensing platform).

FIGS. 9A to 9D show the modulation effects of different ACEi on the S-protein-ACE2 binding. FIG. 9A shows that enalapril positively modulates the S-protein-ACE2 binding in a dose dependent manner. FIG. 9B shows that the dose dependent positive modulation effect is enhanced in the presence of enalaprilat. FIG. 9C shows that lisinopril demonstrates similar positive modulation on the S-protein-ACE2 binding. FIG. 9D shows that captopril devoid of a glycine moiety in its molecular structure has no significant effect on the S-protein-ACE2 binding.

FIGS. 10A to 10D show the modulation effects of different ACEi on the S-protein-ACE2 binding. FIGS. 10A and 10C show that perindopril and ramipril exhibit comparable dose-dependent and non-competitive inhibition against the binding of S-protein to the ACE2, and ramipril exhibits stronger antagonism effect than perindopril. FIGS. 10B and 10D show that the antagonism effect is significantly enhanced when perindoprilat or ramiprilat is used. Near full inhibition of S-protein-ACE2 binding is observed at 4 μg/mL ramiprilat.

FIGS. 11A to 11C show the binding selectivity of the S-protein to the Pd-NTF electrodes under different conditions. FIGS. 11A and 11B show the binding of S-protein to the plain Pd-NTF electrodes (FIG. 11A) and to the lysozyme-coated Pd-NTF electrodes (FIG. 11B). FIG. 11C shows the selective interaction of ACE2-Pd-NTFE with the S-protein (as reflected by the concentration-dependent escalation in $\Delta R_{ct}$) but not with albumin or lysozyme.

FIG. 16A shows the titers of virus stocks stored at −80° C. for 8 days and 2.5 months. FIGS. 16B and 16C show the comparison of viral titers of the S-D614 (D614) and S-G614 (D614G) variants. The stocks of SARS-CoV-2 variants were diluted to $10^4$ plaque-forming unit (PFU)/mL and stored at 4° C. and −20° C. for indicated durations. FIGS. 16D to 16G show the comparison of viral titers of the S-D614 and S-G614 variants stored at 4° C. or −20° C. for 30 days, with indicated initial viral concentrations (PFU/mL). Error bars represent the standard deviations (SD) of three independent experiments (*$p<0.05$, **$p<0.01$, ns: not significant, unpaired t-test).

(FIG. 18A) or −20° C. (FIG. 18B) for 30 days. The respective regression equations and $r^2$ values are shown.

DETAILED DESCRIPTION OF THE EMBODIMENTS

Figure 1:
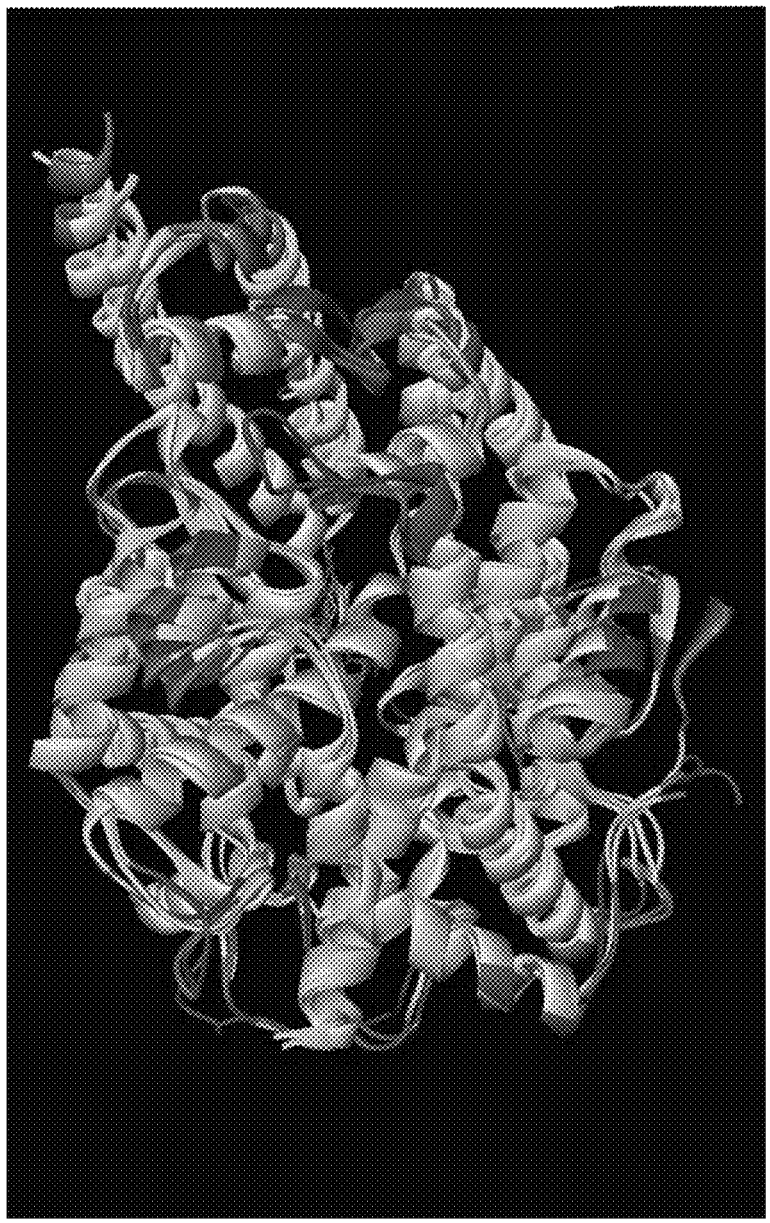
FIG. 1 shows superimposition of ACE2 complex and ACEI complex. The overlapping regions colored in yellow (main-chain root-mean-square deviation (RMSD) values for aligned residues are ≤2.0 Å with PDB ID: 1R4L as reference) while the nonoverlapping regions are colored in red for ACE1 (main-chain RMSD values for aligned residues are >2.0 Å with PDB ID: 1R4L as reference) and blue for the related ACE2 regions.

The following examples are used for illustrating the present disclosure. A person skilled in the art can easily conceive the other advantages and effects of the present disclosure, based on the disclosure of this specification. The present disclosure can also be implemented or applied as described in different examples. It is possible to modify or alter the following examples for carrying out this disclosure without contravening its scope for different aspects and applications.

It is further noted that, as used in this disclosure, the singular forms "a," "an," and "the" include plural referents unless expressly and unequivocally limited to one referent. The term "or" is used interchangeably with the term "and/or" unless the context clearly indicates otherwise.

As used herein, the term "comprising" or "comprises" is used in reference to compositions, methods, and respective component(s) thereof, which are included in the present disclosure, yet open to the inclusion of unspecified elements or steps.

The present disclosure is directed to a method for preventing or treating a viral infection in a subject in need thereof. In at least one embodiment, the method of the present disclosure is effective in protecting the subject from the viral infection by reducing risk of the viral infection and/or alleviating the severity of the viral infection.

In at least one embodiment, the viral infection prevented or treated by the method of the present disclosure may be caused by coronavirus, such as SARS-CoV, MERS-CoV, SARS-CoV-2, mouse hepatitis virus (MHV), porcine epidemic diarrhea virus (PEDV), or a variant thereof.

In at least one embodiment, the method of the present disclosure comprises administering to a subject a modulator that may alter the interaction of coronavirus S-protein and ACE2, thereby influencing the risk of contracting the viral infection or aggravating the disease progression. Accordingly, the modulator identified by the present disclosure may have antiviral activity and/or enhance the host immune response, so as to effectively prevent or treat viral infections.

In at least one embodiment, the modulator is identified by the biosensing platform and the screening method of the present disclosure. In at least one embodiment, the modulator provided in the present disclosure exhibits structural-dependent paradoxical modulations to the S-protein-ACE2 binding. In some embodiments, the modulators of the present disclosure that may enhance the affinity of S-protein to ACE2 are useful in improving the sensitivity of the biosensing platform for detecting the presence of a target virus or raising an immune response against the virus in the subject, while the modulators of the present disclosure that may antagonize the binding of S-protein to ACE2 are useful in inhibiting an infectivity of the virus in the subject.

In at least one embodiment, the modulator provided in the present disclosure is an angiotensin converting enzyme inhibitor (ACEi), such that the modulator is suitable for administration to a subject in need of ACEi. The term "ACEi" as used herein refers to a compound that competitively inhibits angiotensin converting enzyme I (ACE1, also known as ACE) to suppress the formation of angiotensin II, and consequently decrease the activation of angiotensin II type 1 (AT1) receptor and related pharmacological events thereof, such as vasoconstriction, sodium and water retention, and sympathetic activation[6]. In some embodiments, the modulator provided in the present disclosure is administered to a subject suffering from hypertension or a cardiovascular disease.

In at least one embodiment, a method for screening a compound capable of inhibiting entry of a coronavirus into a host cell is also provided. The method comprises determining whether a compound among members of the ACEi family has a cyclopenta[b]pyrrole-2-carboxylic acid moiety or a 1H-indole-2-carboxylic acid moiety. The method further comprises determining whether the compound among members of the ACEi family has a glycine moiety. In some embodiments, the members of the ACEi family include, but are not limited to, lisinopril, captopril, enalapril, enalaprilat, perindopril, perindoprilat, ramipril, and ramiprilat.

In at least one embodiment, the modulator identified by the present disclosure is represented by formula (I) below:

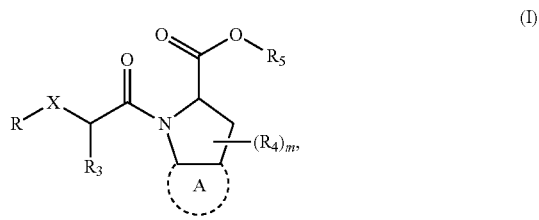

(I)

wherein:
A is absent or a 4- to 6-membered ring;
X is NH or $CH_2$;
R is —SH or —$CHR_2C(=O)OR_1$;
$R_1$ is H, deuterium, $C_{1-6}$ alkyl, $C_{3-10}$ cycloalkyl, $C_{3-10}$ cycloheteroalkyl, $C_{6-10}$ aryl, or $C_{4-10}$ heteroaryl;
$R_2$ is $C_{1-6}$ alkyl, $C_{2-6}$ alkenyl, $C_{2-6}$ alkynyl, $C_{1-6}$ alkoxy, $C_{2-6}$ alkenyloxy, $C_{1-6}$ alkylcarbonyl, $C_{1-6}$ alkyloxycarbonyl, $C_{1-6}$ alkylamino, $C_{3-20}$ cycloalkyl, $C_{3-20}$ cycloheteroalkyl, $C_{6-20}$ aryl, or $C_{4-20}$ heteroaryl;
$R_3$ is H, deuterium, halo, cyano, hydroxyl, carboxyl, amino, formyl, nitro, $C_{1-6}$ alkyl, $C_{2-6}$ alkenyl, $C_{2-6}$ alkynyl, $C_{1-6}$ alkoxy, $C_{2-6}$ alkenyloxy, $C_{1-6}$ alkylcarbonyl, $C_{1-6}$ alkyloxycarbonyl, $C_{1-6}$ alkylamino, $C_{3-20}$ cycloalkyl, $C_{3-20}$ cycloheteroalkyl, $C_{6-20}$ aryl, or $C_{4-20}$ heteroaryl;
$R_4$ is H, deuterium, amino, halo, hydroxyl, $C_{1-6}$ alkyl or $C_{1-6}$ alkoxy;
$R_5$ is H, deuterium, or $C_{1-6}$ alkyl; and
m is an integer of 1 to 4.

It should also be recognized that all, or almost all, of the above-defined groups may be substituted with one or more substituents, which may in turn be substituted as well. For example, the phrase "substituted alkyl" refers to alkyl as just described including one or more substituents of deuterium, alkyl, alkenyl, alkynyl, hydroxyalkyl, fluoroalkyl, chloroalkyl, bromoalkyl, iodoalkyl, perfluoroalkyl, aryl, heteroaryl, cycloalkyl, cycloalkenyl, cycloheteroalkyl, carboxyl, aralkyl, aralkenyl, aralkynyl, heteroaralkyl, heteroaralkenyl, heteroaralkynyl, heterocyclyl, acyl, aminocarbonyl, aminoalkyl, amino, alkylamino, hydroxyl, alkoxy, aryloxy, silyloxy, amido, imidoyl, carbamoyl, halo, cyano, nitro, phosphate group, thio, thioether, sulfo, and sulfamido.

The term "one or more" as used herein refers to either one or a number above one (e.g., 2, 3, 4, 5, 6, 7 or more).

The term "halo" or "halogen" alone or as part of another substituent as used herein refers to a fluorine, chlorine, bromine, or iodine atom.

The term "alkyl" as used herein refers to saturated hydrocarbon groups in a straight, branched, or cyclic configuration (also referred to as "cycloalkyl" below). The term "$C_{1-6}$ alkyl" (alone or in combination with another term) refers to an alkyl containing 1 to 6 (e.g., 1 to 5, 1 to 4, or 1 to 3) carbon atoms. Exemplary $C_{1-6}$ alkyl include methyl, ethyl, n-propyl, isopropyl, n-butyl, isobutyl, sec-butyl, tert-butyl, n-pentyl, and the like.

The term "alkenyl" as used herein refers to an alkyl as defined above and having at least one double bond. For example, the term "$C_{2-6}$ alkenyl" (alone or in combination with another term) refers to a straight or branched chain hydrocarbyl substituent containing 2 to 6 (e.g., 2 to 5, 2 to 4, or 2 to 3) carbon atoms and one or more double bonds. Exemplary alkenyl groups include straight, branched, or cyclic alkenyl groups having two to twelve carbon atoms (e.g., ethenyl, propenyl, butenyl, and pentenyl).

Similarly, the term "alkynyl" as used herein refers to an alkyl or alkenyl as defined above and having at least one triple bond. Exemplary alkynyl groups include straight, branched, or cyclic alkynes having two to twelve carbon atoms (e.g., ethynyl, propynyl, butynyl, and pentynyl).

The term "cycloalkyl" as used herein refers to a cyclic alkane (in which a chain of carbon atoms of a hydrocarbon forms a ring) including from 3 to 20 ($C_{3-20}$) ring atoms. In some embodiments, the exemplary cycloalkyl may have from 3 to 10 ($C_{3-10}$), from 3 to 8 ($C_{3-8}$), from 4 to 8 ($C_{4-8}$), from 3 to 6 ($C_{3-6}$), from 4 to 6 ($C_{4-6}$), or from 5 to 6 ($C_{5-6}$) ring atoms. Exemplary cycloalkyl groups include cyclopropyl, cyclobutyl, cyclopentyl, cyclohexyl, cycloheptyl, and cyclooctyl. In the present disclosure, the cycloalkyl groups may also include a double or triple bond (and may therefore also be termed cycloalkenyl or cycloalkynyl).

The term "cycloheteroalkyl" refers to a saturated or partially unsaturated (i.e., "cycloheteroalkenyl" monocyclic or bicyclic (fused, bridged, or spiro) ring containing from 3 to 20 ($C_{3-20}$) ring atoms which can comprise one, two or three heteroatoms selected from O, S, and N. In some embodiments, the exemplary heterocyclyl may have from 3 to 10 ($C_{3-10}$), from 3 to 8 ($C_{3-8}$), from 4 to 8 ($C_{4-8}$), from 3 to 6 ($C_{3-6}$), from 4 to 6 ($C_{4-6}$), or from 5 to 6 ($C_{5-6}$) ring atoms. The cycloheteroalkyl may be attached to a main structure at any heteroatom or carbon atom which results in the creation of a stable compound. Exemplary cycloheteroalkyl groups include azetidinyl, pyrrolidinyl, piperidinyl, piperazinyl, morpholinyl, oxetanyl, tetrahydropyranyl, tetrahydrothiopyranyl, and tetrahydrofuryl.

The term "aryl" as used herein refers to an aromatic carbon atom-containing ring, which may further include one or more non-carbon atoms (also referred to as "heteroaryl"). In some embodiments, the exemplary aryl may have from 6 to 20 ($C_{6-20}$), from 6 to 14 ($C_{6-14}$), or from 6 to 10 ($C_{6-10}$) ring atoms. Exemplary aryl groups include cycloalkenyls (e.g., phenyl and naphthyl) and pyridyl. Exemplary heteroaryl groups include 5- and 6-membered rings with one, two, three or four heteroatoms independently selected from O, S, and N (e.g., imidazole, pyrrole, triazole, dihydropyrimidine, indole, pyridine, thiazole, and tetrazole).

The term "alkoxy" as used herein refers to straight or branched chain alkoxides, wherein the hydrocarbon portion may have any number of carbon atoms (and may further include a double or triple bond), such as alkyl, aryl, arylalkyl, and cycloalkyl. For example, suitable alkoxy groups include methoxy, ethoxy, and isopropoxy. Furthermore, the term "aryloxy" denotes groups "—OAr," where Ar is aryl or heteroaryl.

In at least one embodiment, the present disclosure provides a method for preventing or treating a viral infection in a subject in need thereof, comprising administering to the subject an effective amount of the above-mentioned modulator or compound.

As used herein, the terms "treat," "treating," and "treatment" are meant to obtaining a desired pharmacologic and/or physiologic effect, e.g., attenuating the progression of viral infection. The effect may be prophylactic in terms of completely or partially preventing a disease or symptom thereof, or may be therapeutic in terms of completely or partially curing, alleviating, relieving, remedying, ameliorating a disease or an adverse effect attributable to the disease or symptom.

As used herein, the terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

As used herein, the terms "patient," "individual" and "subject" are used interchangeably. The term "subject" means a human or animal. Examples of the subject include, but are not limited to, human, monkey, mice, rat, woodchuck, ferret, rabbit, hamster, cow, horse, pig, deer, dog, cat, fox, wolf, chicken, emu, ostrich, and fish. In some embodiments of the present disclosure, the subject is a mammal, e.g., a primate such as a human.

As used herein, the phrase "an effective amount" refers to the amount of an active compound (e.g., an antivirus agent and an adjuvant) that is sufficient to prevent development of, or alleviate to some extent, one or more of the symptoms of the disorder, disease, or condition being prevented or treated. Effective doses will vary, as recognized by those skilled in the art, depending on routes of administration, excipient usage, the possibility of co-usage with other therapeutic treatment, and the condition to be prevented or treated.

As used herein, the term "administering" or "administration" refers to the placement of an active compound (e.g., an antivirus agent and an adjuvant) into a subject by a method or route which results in at least partial localization of the active compound at a desired site to produce a desired effect. The active compound described herein may be administered by any appropriate route known in the art including, but not limited to, oral or parenteral routes, including intraperitoneal, intravenous, intradermal, intramuscular, subcutaneous, or transdermal routes.

As used herein, the term "adjuvant" refers to any substance that may enhance an immunological response in a host in addition to an antigen protein.

In at least one embodiment, the compound may be formulated into an antiviral medicine for administration. The antiviral medicine comprises the above compound as an antivirus agent in an effective amount and a pharmaceutically acceptable carrier thereof.

As used herein, the term "pharmaceutically acceptable carrier" refers to a pharmaceutically acceptable material, composition, or vehicle, such as diluents, disintegrating agents, binders, lubricants, glidants, and surfactants, which does not abrogate the biological activity or properties of the compound, and is relatively non-toxic; that is, the material may be administered to an individual without causing an undesirable biological effect or interacting in a deleterious manner with any of the components of the composition in which it is contained.

In at least one embodiment, the compound may be formulated into a vaccine composition for administration. The vaccine composition comprises an antigen (e.g., virus-like particles (VLPs)) and the above compound as an adjuvant in an effective amount sufficient to promote immune responses.

In at least one embodiment, a method for detecting a viral infection in a subject in need thereof is also provided. The method comprises detecting the presence of the virus in a biological sample from the subject by the biosensing platform provided herein.

As used herein, the terms "detecting," "determining," "assessing," "assaying," and "measuring" refer to both quantitative and qualitative determinations and as such, the term "detecting" is used interchangeably herein with "assaying," "measuring," and the like. Where a quantitative determination is intended, the phrase "determining an amount" and the like is used. Where either a qualitative or quantitative determination is intended, the phrase "measuring a level" or "detecting a level" may be used.

As used herein, the term "biological sample" refers to a sample to be analyzed by any of the methods described herein that can be of any type of samples obtained from a subject to be detected. The biological samples used herein include, but are not limited to: tissue samples (such as tissue sections and needle biopsies of a tissue); cell samples (e.g., cytological smears (such as Pap or blood smears) or samples of cells obtained by microdissection); samples of whole organisms (such as samples of yeasts or bacteria); or cell fractions, fragments or organelles (such as those obtained by lysing cells and separating the components thereof by centrifugation or otherwise). Other examples of biological samples include, but are not limited to, body fluid samples, such as blood, serum, plasma, urine, sputum, saliva, cerebrospinal fluid, interstitial fluid, mucous, sweat, stool extract, fecal matter, synovial fluid, tears, semen, peritoneal fluid, nipple aspirates, milk, vaginal fluid, or any combination thereof. In some embodiments, a blood sample can be whole blood or a faction thereof, e.g., serum or plasma, heparinized or EDTA treated to avoid blood clotting.

Many examples have been used to illustrate the present disclosure. The examples below should not be taken as a limit to the scope of the present disclosure.

EXAMPLES

The materials used in the present disclosure but unannotated herein are commercially available.

Example 1: Computational Structural Superimposition Analysis

The crystal structures of ACE2 (Protein Data Bank (PDB) ID: 1R4L, complexed with MLN-4760) and ACE1 (PDB ID: 1UZE, complexed with enalaprilat; PDB ID: 2X94, complexed with perindoprilat; PDB ID: 1086, complexed with lisinopril; and PDB ID: 2X92, complexed with ramiprilat) were obtained from SWISS-MODEL server and superimposed to assess the structural similarities. To select the candidates for the biosensing-based SARS-CoV-2-ACE2 binding inhibitor screening experiments, the chemical structures of a panel of peptide analogs known to inhibit ACE (such as captopril, enalaprilat, perindoprilat, ramiprilat and lisinopril) were respectively superimposed virtually onto MLN-4760 (ACE2 inhibitor)-ACE2 complex and examined via superimposition function in Discovery Studio Visualizer to generate ACEi-ACE2 interaction diagrams.

Figure 2:
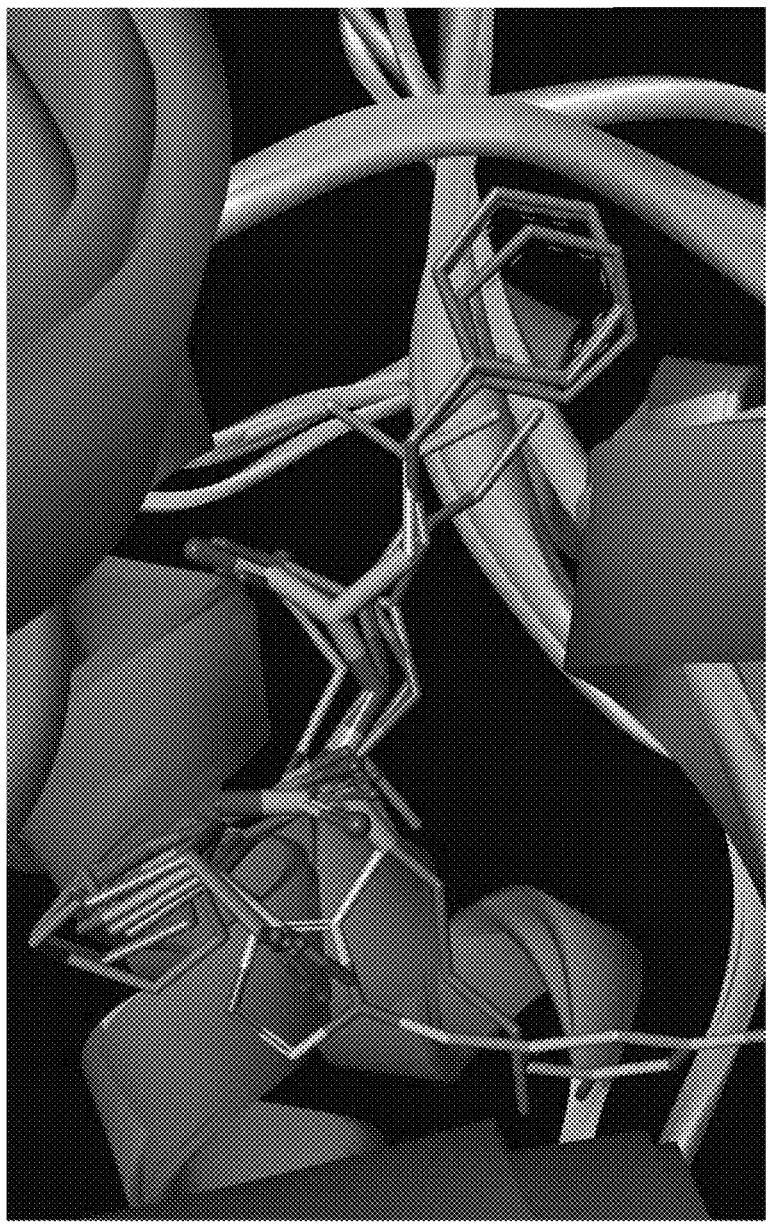
FIG. 2 shows superimposition of ACE2 inhibitor (MLN-4760) (in white tube form) and its analogs, i.e., enalaprilat (green), perindoprilat (pink), lisinopril (gold) and ramiprilat (orange). The superimposed ACEi (or their metabolites), i.e., enalaprilat, perindoprilat, lisinopril and ramiprilat, possess an acetone-glycine moiety (the carbon atoms are colored in yellow) resembled to that of the classical ACE2 inhibitor MLN-4760.
Figure 3A:
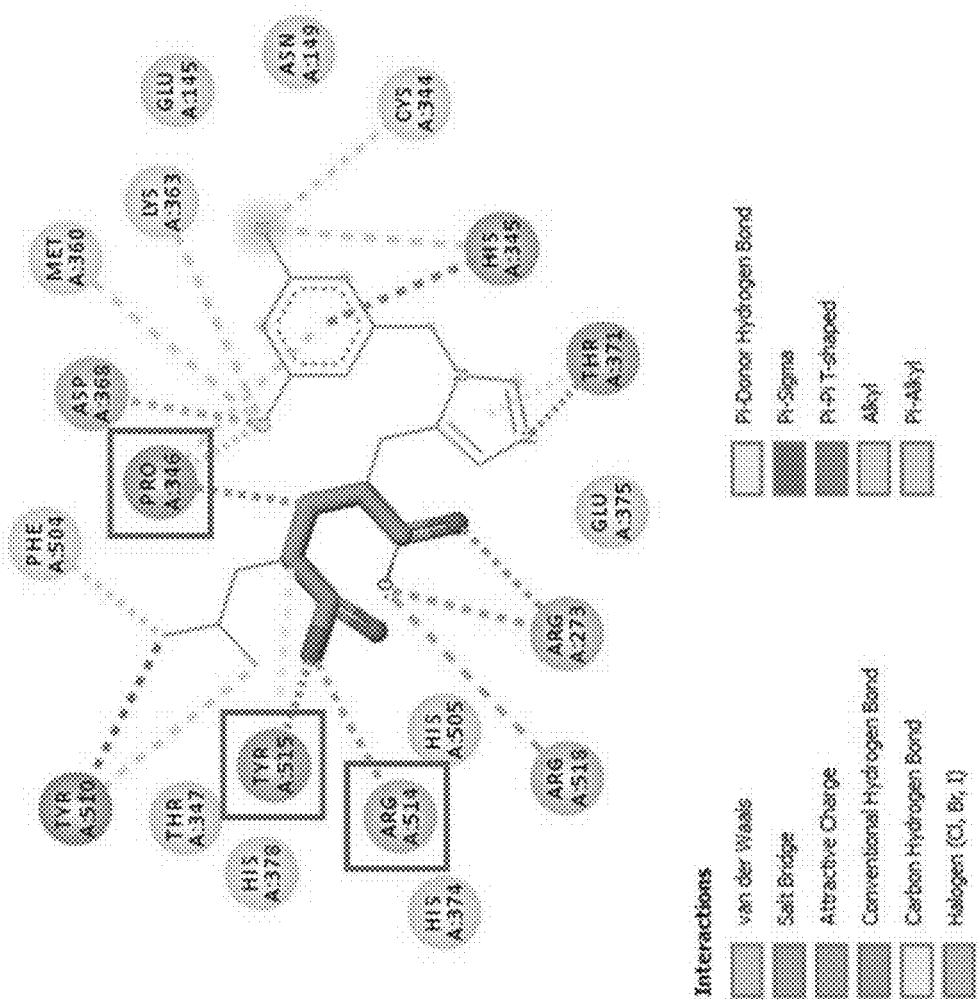
Figure 3B:
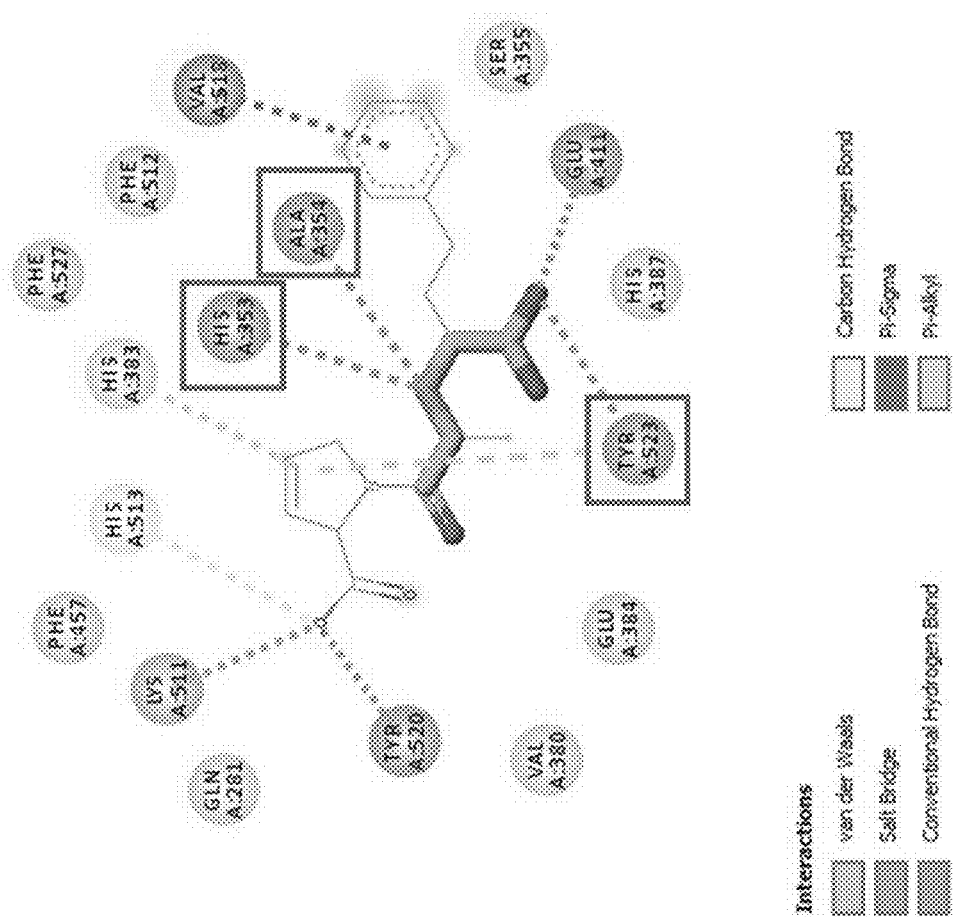
Figure 3E:
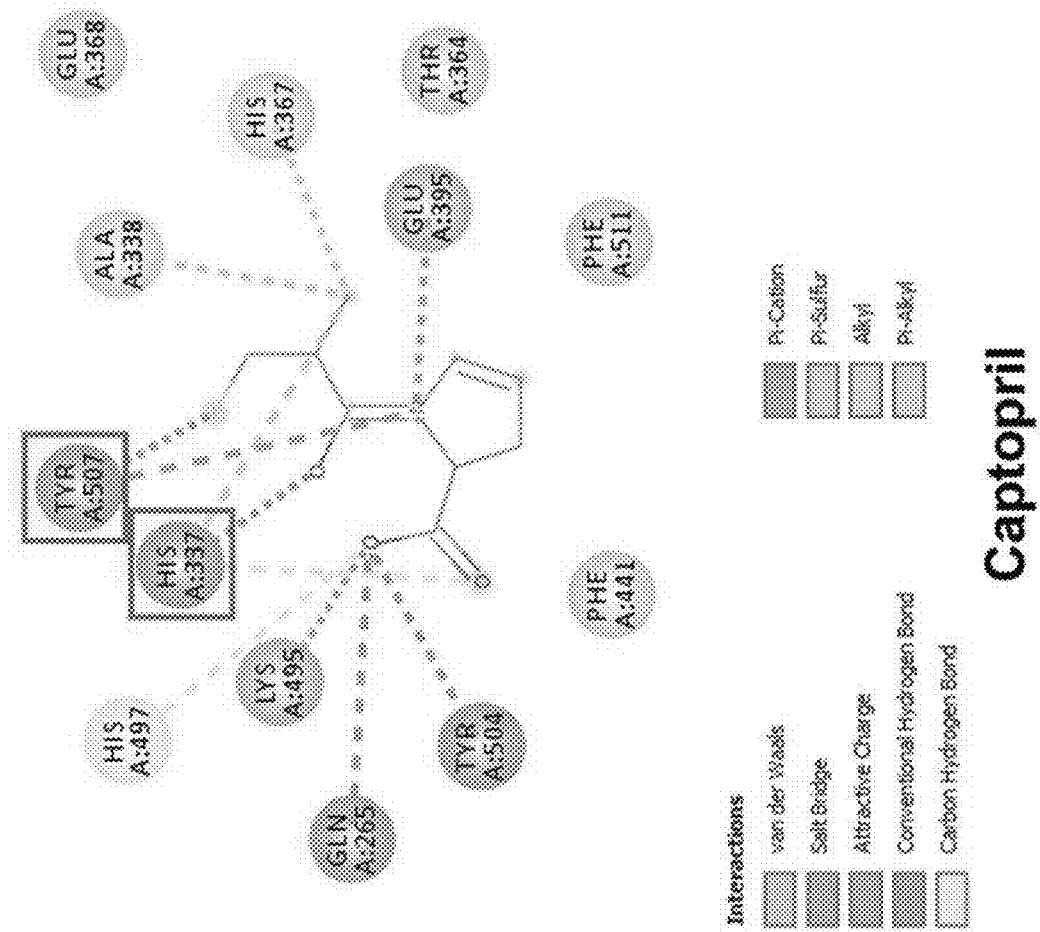
Figure 3F:
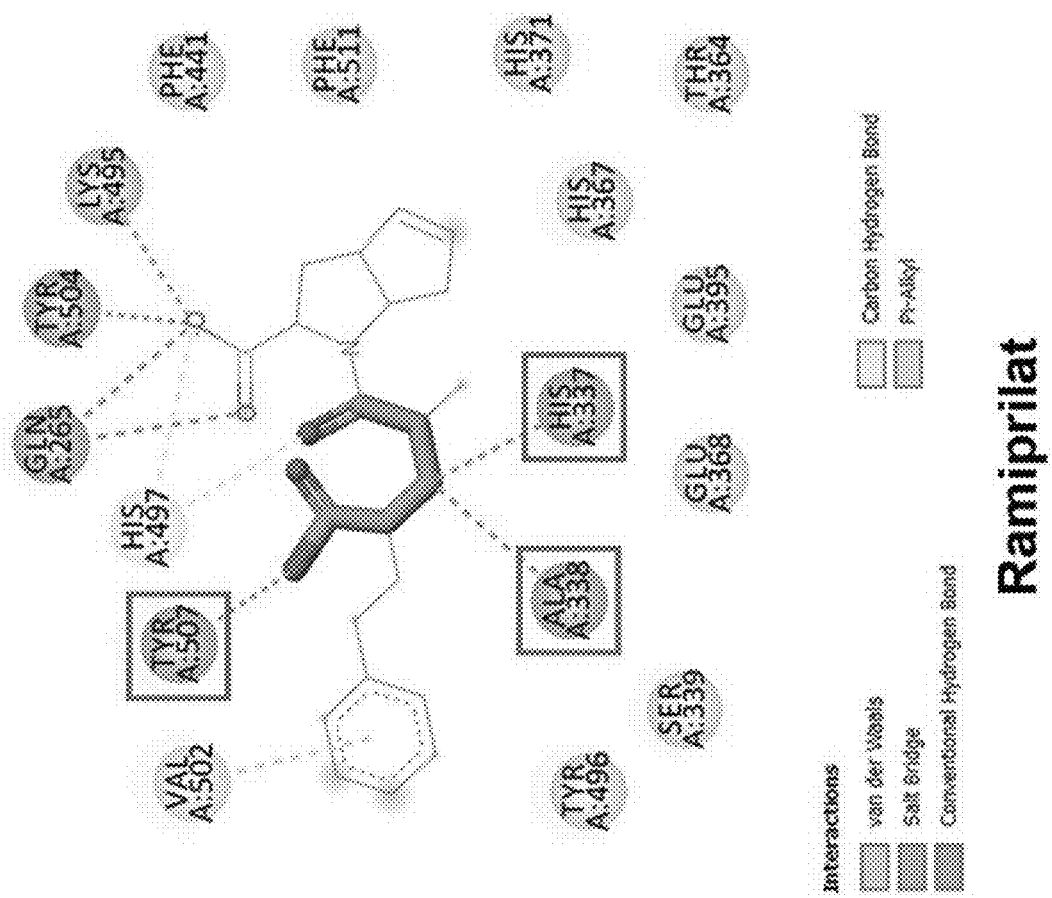

Through a computational structural superimposition analysis, the 3-dimensional structures of ACE and ACE2 complexes were well aligned to each other (FIGS. 1 and 2). It was further observed that several peptide analogs of the pharmacological ACEi class that possess a (2-oxoethyl) glycine moiety resembled that of the classical ACE2 inhibitor MLN-4760 and its analogs, such as lisinopril, enalaprilat, perindoprilat, and ramiprilat, may afford hydrogen bond interactions with the amino acid residues within the binding pocket of the ACE2 enzyme active site, which were found to promote interactions with the amino acid residues in the active site of ACE2 via hydrogen bonding, so as to affect the structural conformation of ACE2 to augment or interfere with ACE2-S-protein binding (FIGS. 1, 2 and 3A to 3F). Hence, these peptide analogs were selected as candidates for the subsequent screening of SARS-CoV-2-ACE2 binding inhibitors using the developed biosensing platform.

Referring to FIGS. 3A to 3F, ACEi of different subtypes forms hydrogen bonding with different amino acid residues of the ACE2 binding pockets via their acetone-glycine moiety (i.e., enalaprilat and lisinopril with His353, Ala354 and Tyr523 vs. perindoprilat and ramiprilat with His337, Ala338 and Tyr507). This may result in differential ACEi-ACE2 interactions. Meanwhile, the absence of hydrogen bond between captopril (negative control: without acetone-glycine moiety) and Ala338 residue may reduce the stability and affinity of captopril towards ACE1 as well as ACE2.

Figure 4:
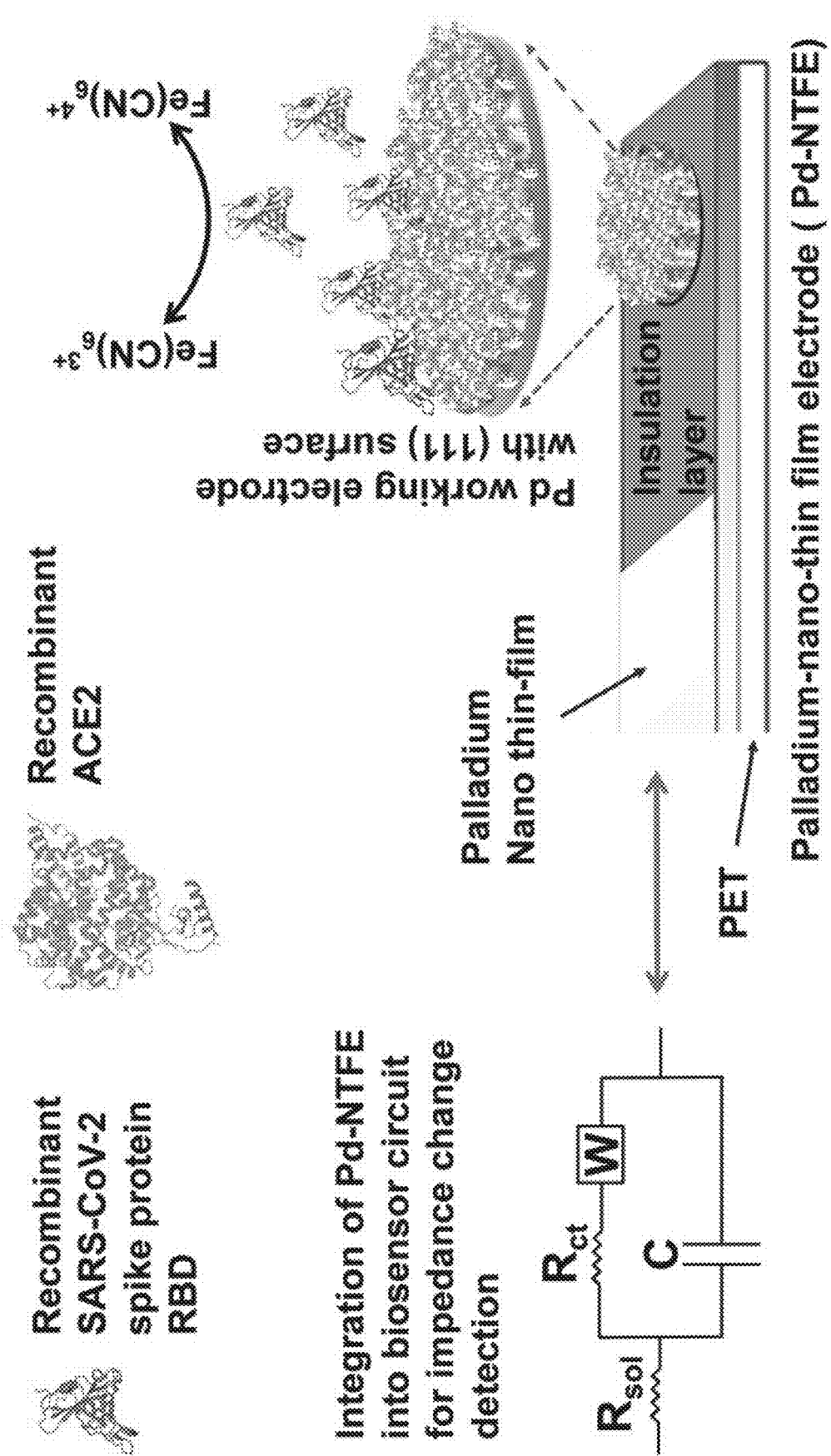
FIG. 4 is a diagram illustrating the electrochemical impedance spectroscopy (EIS)-based biosensing platform with ACE2-coated palladium nano-thin film electrode (Pd-NTFE) as a biosensing probe against SARS-CoV-2 S-protein. $R_{ct}$: charge transfer resistance; $R_{sol}$: solution resistance; C: capacitance; W: Warburg impedance; PET: polyethylene terephthalate.

Example 2: Electrochemical Impedance Spectroscopy (EIS)-Based Biosensor Design and Characterization In this Example, an EIS-based biosensing platform was prepared to identify potential pharmacological inhibitors from the selected FDA-approved ACE/ACE2-interacting peptide analogs to the interaction of ACE2 and SAR-CoV-2 S-protein (FIG. 4).

Figure 5A:
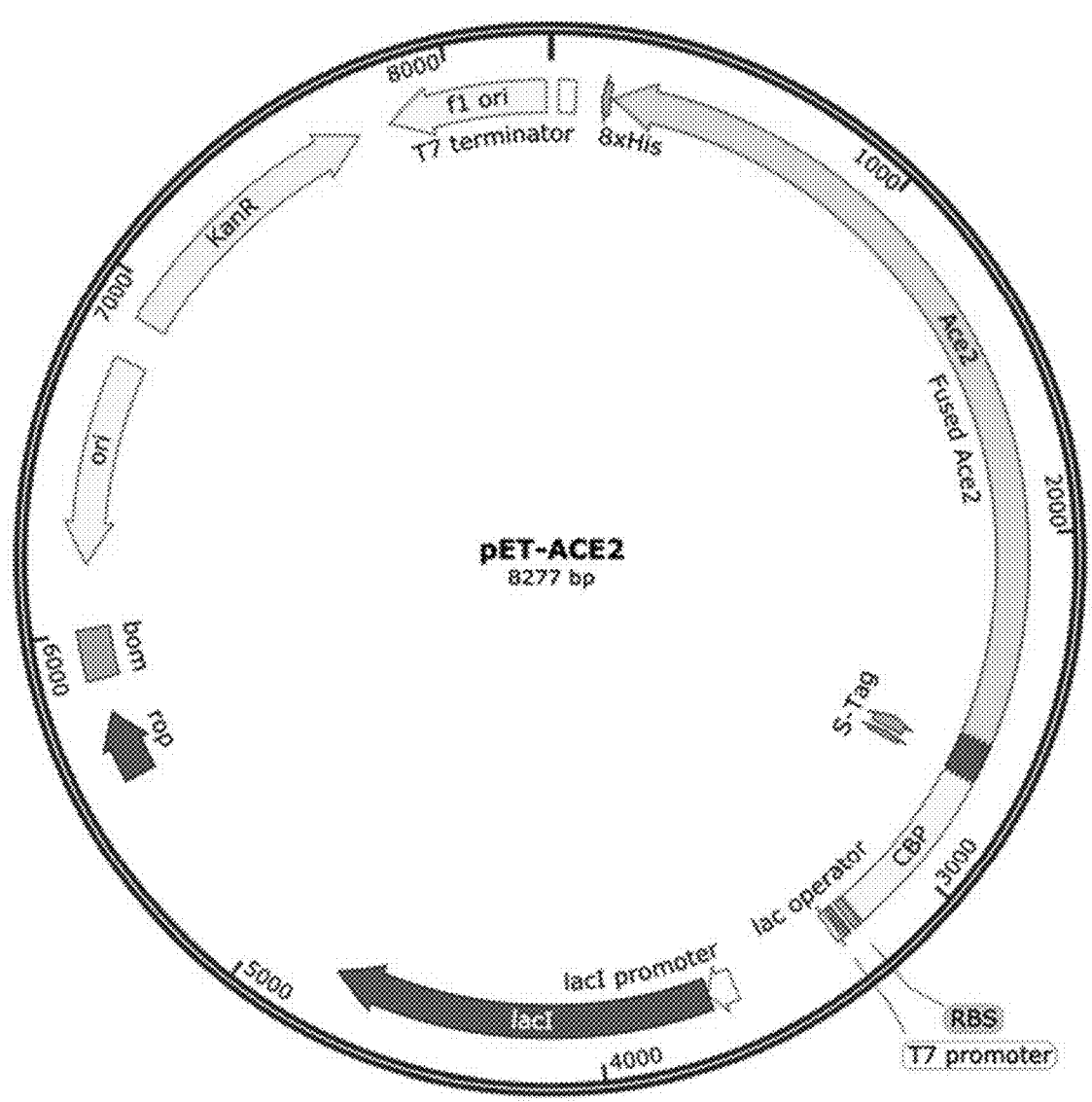
FIGS. 5A and 5B show diagrams illustrating plasmid maps of pET-ACE2 and pUC-spike RBD for expressing ACE2 and SARS-CoV-2 S-protein, respectively. RBD: receptor binding domain; RBS: ribosome binding site; CBP: cellulose binding domain-containing protein; bom: basis of mobility region from pBR322; rop: repressor of primer; CAP binding site: catabolite activator protein binding site.
Figure 5B:
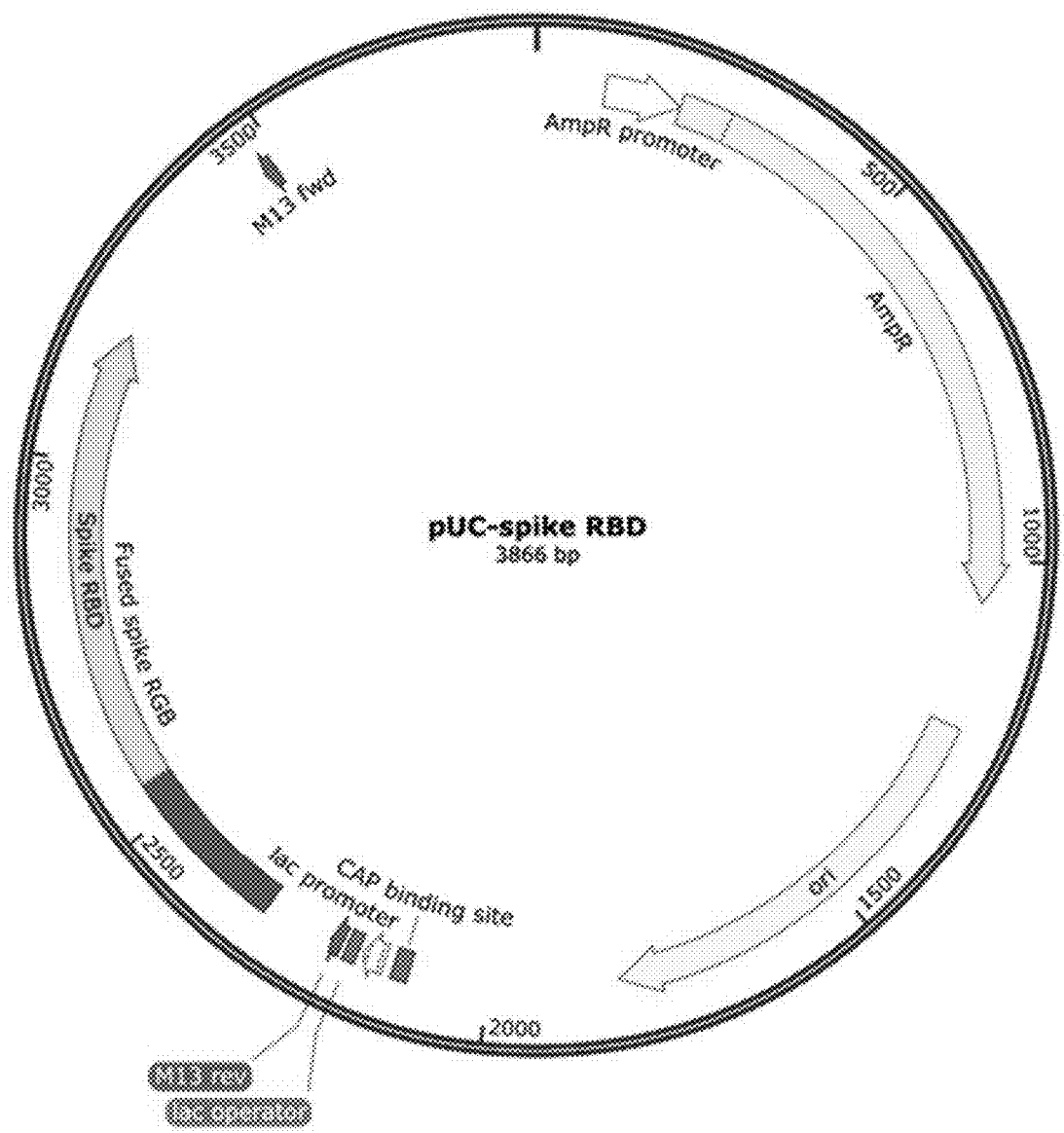

(2.1) Recombinant Expression and Characterization of ACE2 and SARS-CoV-2 S-Protein ACE2 and SARS-CoV-2 S-protein receptor binding domain (RBD) (herein referred to as S-protein) were recombinantly expressed via the *Escherichia coli* system. Briefly, gene sequences for ACE2 and S-protein were obtained from SWISS-MODEL and were synthesized through the chemical synthesis method by Genomics Co. (Taipei, Taiwan). The synthesized ACE2 and S-protein gene fragments were then sub-cloned into pUC expression vectors, respectively (FIGS. 5A and 5B), and the resulting vectors were transformed into XLI-Blue strain *E. coli* host. To overexpress the recombinant ACE2 and S-protein, the refreshed hosts were induced with 0.5 mM isopropyl β-D-thiogalactopyranoside (IPTG) and incubated into 250 mL Luria-Bertani medium at 37° C. for 18 hours. The amino acid sequences of the recombinant ACE2 and S-protein were represented by SEQ ID NO: 1 and SEQ ID NO: 2, respectively.

After the incubation, the recombinant ACE2 and S-protein were isolated from the bacterial inclusion body and refolded with the quasi-static over-critical folding process (QSoCFP). Briefly, denatured ACE2 or S-protein from the inclusion body was dissolved in a denatured solvent. The denatured proteins were then refolded step by step through reducing the concentration of denaturant and salts in the protein solution and gradually adjusting the solution pH from 12 to 8.8. The ACE2 and S-protein were expected to be refolded after a series of buffer changes.

Figure 6A:
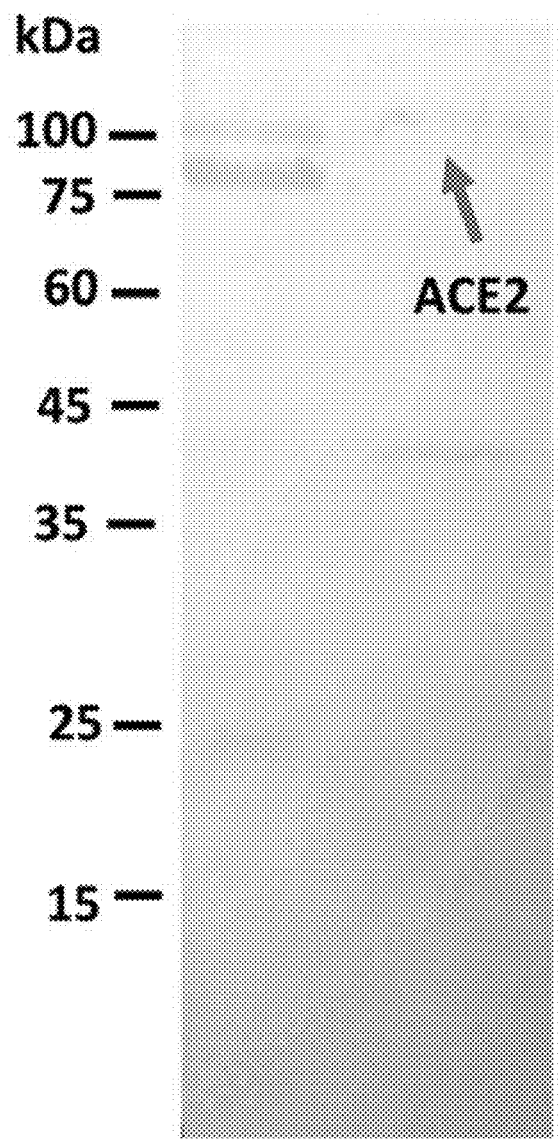
FIGS. 6A to 6C show the results of confirmation of the identities of recombinant ACE2 (using anti-ACE2 monoclonal antibody, FIG. 6A) and recombinant S-protein (receptor binding domain, RBD; using anti-S-protein antibody, FIG. 6B), and the results of ACE2-S-protein binding assay (FIG. 6C).
Figure 6B:
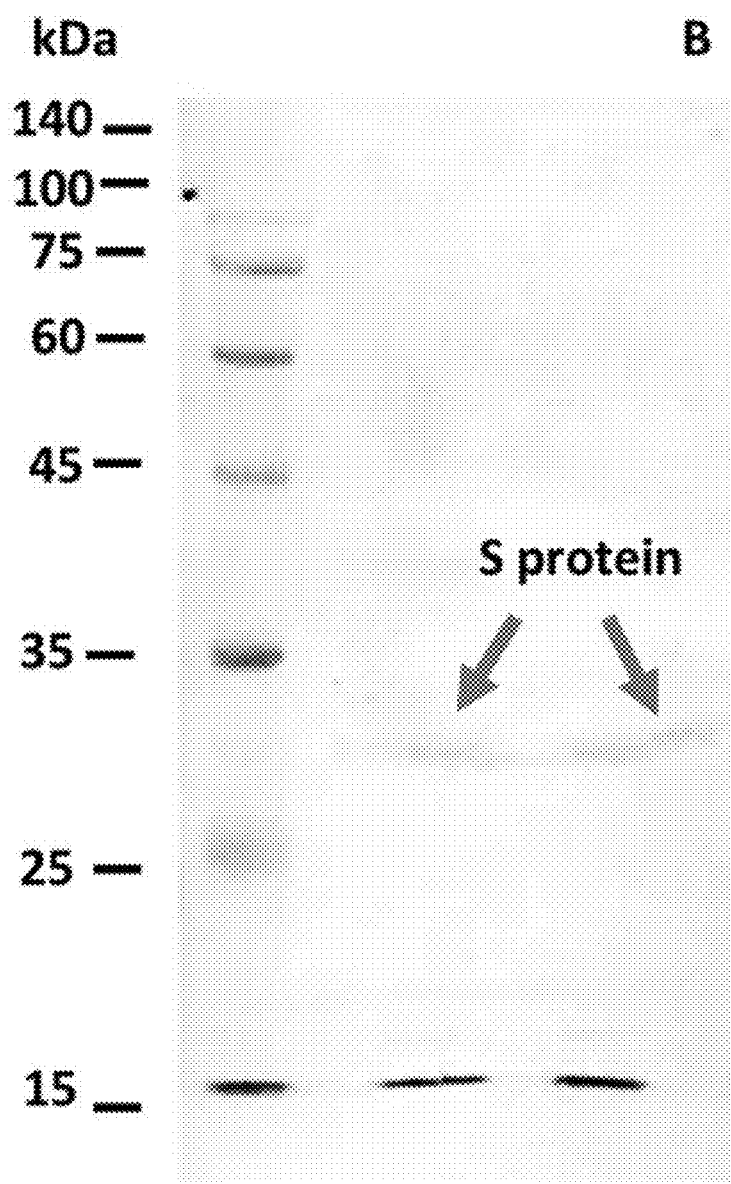

Upon completion of the protein refolding, sodium dodecyl sulfate polyacrylamide gel electrophoresis (SDS-PAGE) and western blotting (using anti-ACE2 (Novus Biologicals LLC, Centennial CO, USA) and anti-S-protein (Genetex Inc., Hsinchu, Taiwan) polyclonal antibodies) were performed to confirm the identity and purity of the expressed ACE2 and S-protein. The concentrations of ACE2 and S-protein were determined using ultraviolet-visible (UV-vis) spectroscopy at a wavelength of 280 nm, and the results were shown in FIGS. 6A and 6B, respectively. Physico-chemical characterization studies such as dynamic light scattering (DLS, laser wavelength at 532.15 nm, Coherent, Santa Clara, CA, USA), transmission electron microscopy (TEM), circular dichroism (CD), etc. were then on the ACE2 and S-protein.

(2.2) ACE2 and S-Protein Dot Blot Binding Assay

A dot blot binding assay was performed to assess the affinity of the synthesized recombinant S-protein to recombinant ACE2. The polyvinylidene difluoride (PVDF) membrane was activated using 100% ethanol for 1 min before the deposition and drying of ACE2 protein (0.2 mg/mL) onto the membrane at the center of the grid (3 to 4 mm in diameter). The membrane was then incubated in a blocking solution (5% skim milk in TBS-T (tris-buffered saline with 0.1% Tween 20)) for 1 hour, followed by incubation with alkaline phosphatase-conjugated S-protein (1.25 to 2,500 pM) for 2 hours at room temperature. The membrane was then washed thrice with TBS-T for 5 min and incubated with NBT/BCIP (nitro-blue tetrazolium chloride/5-bromo-4-chloro-3'-indolylphosphate p-toluidine salt) reagent for 1 to 15 min. The density of the dark-colored dots developed on the membrane was quantified using the densitometry program (ImageJ, NCBI).

Figure 6C:
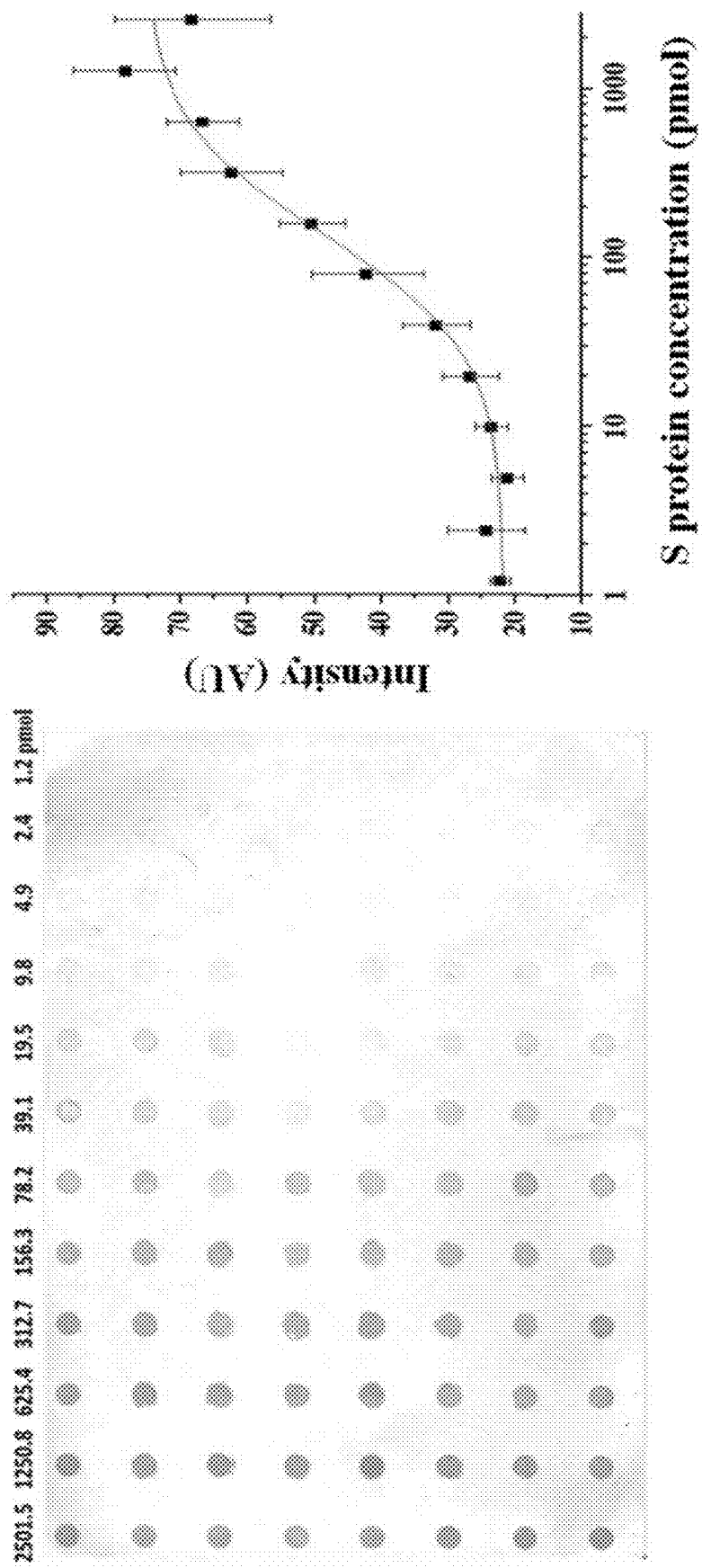

As shown in FIG. 6C, the recombinant S-protein was found to interact with the recombinant ACE2 in a concentration-dependent manner, as reflected by the increase in the intensity of the color dots produced by the S-protein-linked horseshoe peroxidase at the ACE2-spotted regions of the membrane. These findings demonstrated the presence of molecular interactions between the recombinant synthesized S-protein and ACE2, and further validated the feasibility of employing EIS-based biosensing to assay such interactions.

(2.3) nCoV-S Pseudovirus

The nCoV-S Luc pseudovirus was obtained from the National RNAi Core Facility at Academia Sinica, Taiwan by using pCMVdeltaR8.91 and pcDNA3.1 to express S-proteins on the surface of the pseudovirus. The entry of pseudovirus was identified by the luminescence emitted from the luciferase encoded in the transfer vector pLAS2w.FLuc.Ppuro.

(2.4) Preparation of ACE2-Coated Palladium Nano-Thin-Film (Pd-NTF)-Electrochemical Impedance Spectroscopy (EIS) Setup The palladium nano-thin film electrode (Pd-NTFE) was fabricated according to the method reported previously[2]. Briefly, two granule layers of Pd were deposited on the polyethylene terephthalate (PET) substrate by a sputtering process to produce a Pd-NTFE. The crystalline structure of the Pd thin film was investigated using a low-temperature X-ray diffractometer (XRD) (D8, Bruker, Billerica, MA, USA). The scan range was from 20° to 60°, in increments of 0.05°/s. Thereafter, with a fixed small-angle incident X-ray beam at 1°, the XRD signal was analyzed via the Scherrer equation, as shown below:

$$\tau = \frac{K\lambda}{\beta\cos\theta}$$

where, $\tau$ denotes the grain size, K denotes the dimensionless shape factor (about 0.89), $\lambda$ denotes the X-ray wavelength, $\beta$ denotes the full width at half maximum of the intensity (FWHM), and $\theta$ denotes the Bragg angle. The wavelength of X-ray in this example was 1.54 Å.

As a result, the fabricated Pd-NTF electrode was found harboring a retainable Pd surface with specifically coordinated Pd (111) and Pd (200) nanocrystalline structures (granule size respectively at about 3.81 nm and about 6.09 nm, estimated based on the Scherrer equation) that favors the conjugation of biomolecules.

Figure 7A:
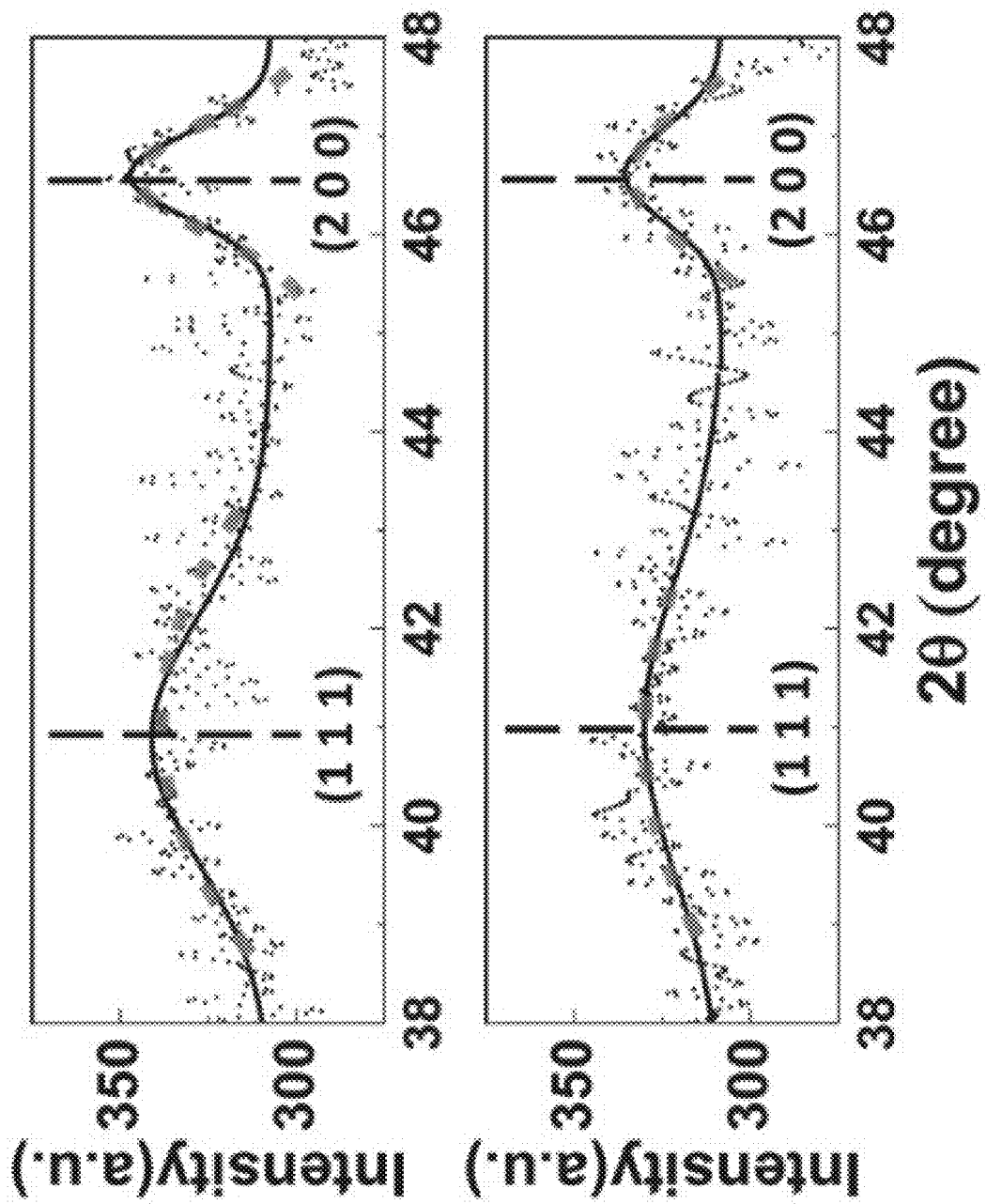
FIGS. 7A to 7C show the characterization of ACE2-Pd-NTF electrode.

To protect the electrode surface from reacting with the environmental elements, a thin layer of indium tin oxide (ITO) was used to cover the surface. Immediately before bio-conjugation, the ITO coating was removed via oxalate acid etching. The XRD analysis indicated that the ITO coating and removal processes did not change the Pd surface structure or the bio-conjugation efficiency (FIG. 7A).

Figure 7B:
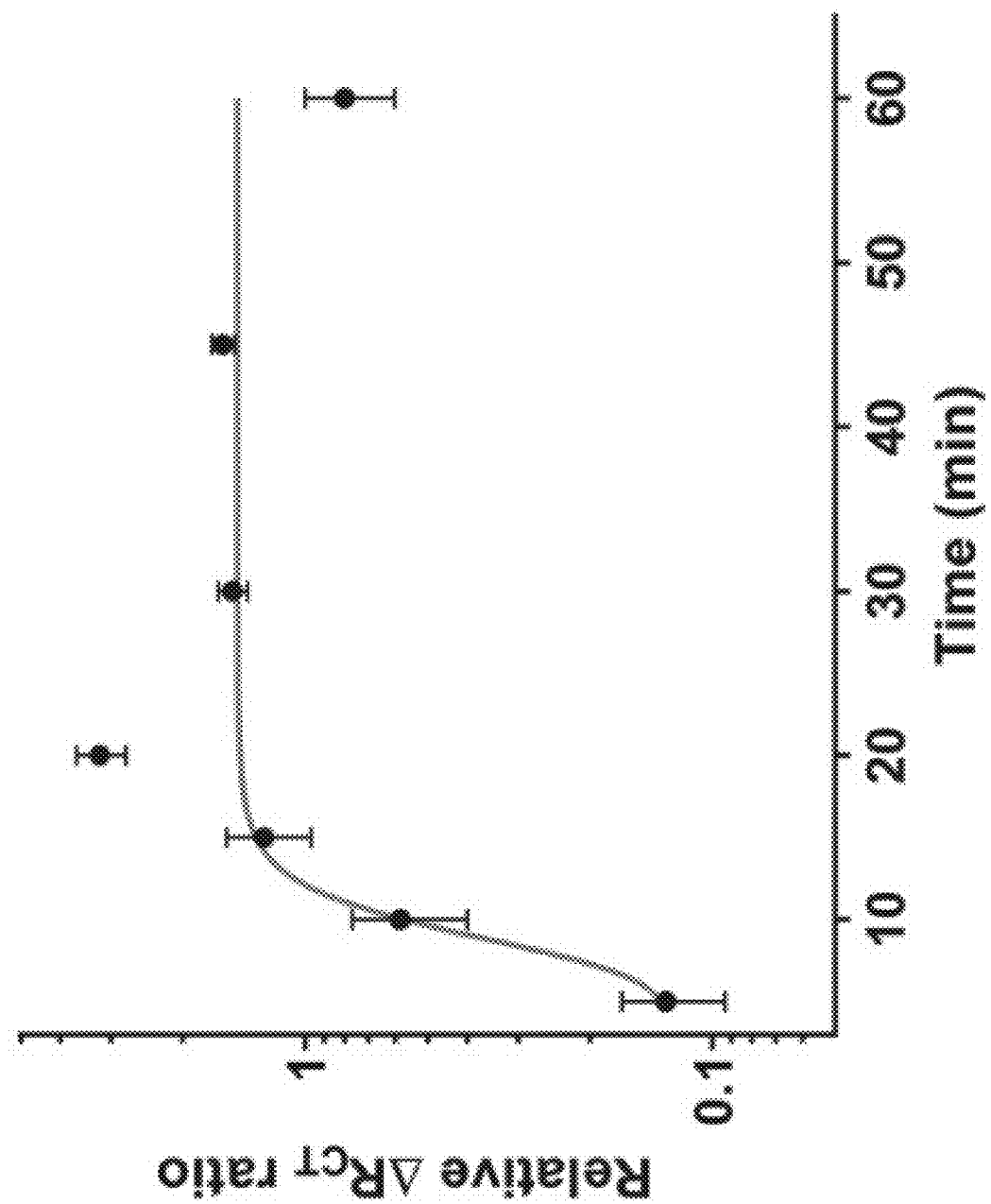

Further, to fabricate the biosensing electrode, 1 µL of the recombinantly-expressed ACE2 (0.8 mg/mL) was then deposited onto the Pd-NTFE and incubated at room temperature for 20 min to form a functional ACE2 layer through the direct formation of Pd—S bonds between ACE2 and the active Pd surface. As shown in FIG. 7B, the Pd-NTFE exposed to the recombinant ACE2 protein allowed its rapid immobilization (within 20 min) on the electrode surface. The formed ACE2-coated Pd-NTFE was then rinsed with double distilled water ($ddH_2O$) to remove excess proteins, followed by backfilling with 1 µL of 1-octadecanethiol (0.1 mM) at room temperature for 10 to 15 min.

The Raman spectra of ACE2 immobilized on the Pd-NTFE were obtained using a custom-built micro-Raman system. The Raman signal was analyzed using an ANDOR KYMERA-328i-A instrument with an ANDOR DR-05880 (Andor Tech. Ltd., Oxford Instruments, Belfast, UK). The formed ACE2-Pd-NTFE biosensor was then analyzed using impedance spectroscopy, whereby the successful coating of ACE2 onto the Pd-NTF was determined through comparing the charge transfer resistance ($R_{ct}$) generated by the Pd-NTF before and after the ACE2 treatment, i.e., an elevation of $R_{ct}$ values indicated successful coating. Scanning electron microscopy (SEM), atomic force microscopy (AFM) and Raman spectroscopy were also performed to further confirm the successful coating of ACE2 onto the Pd-NTFE. Subsequently, the ACE2-Pd-NTFE biosensor was coupled to the impedance spectroscopy device/amplifiers to form the complete ACE2-Pd-NTFE biosensor-EIS setup.

Figure 7C:
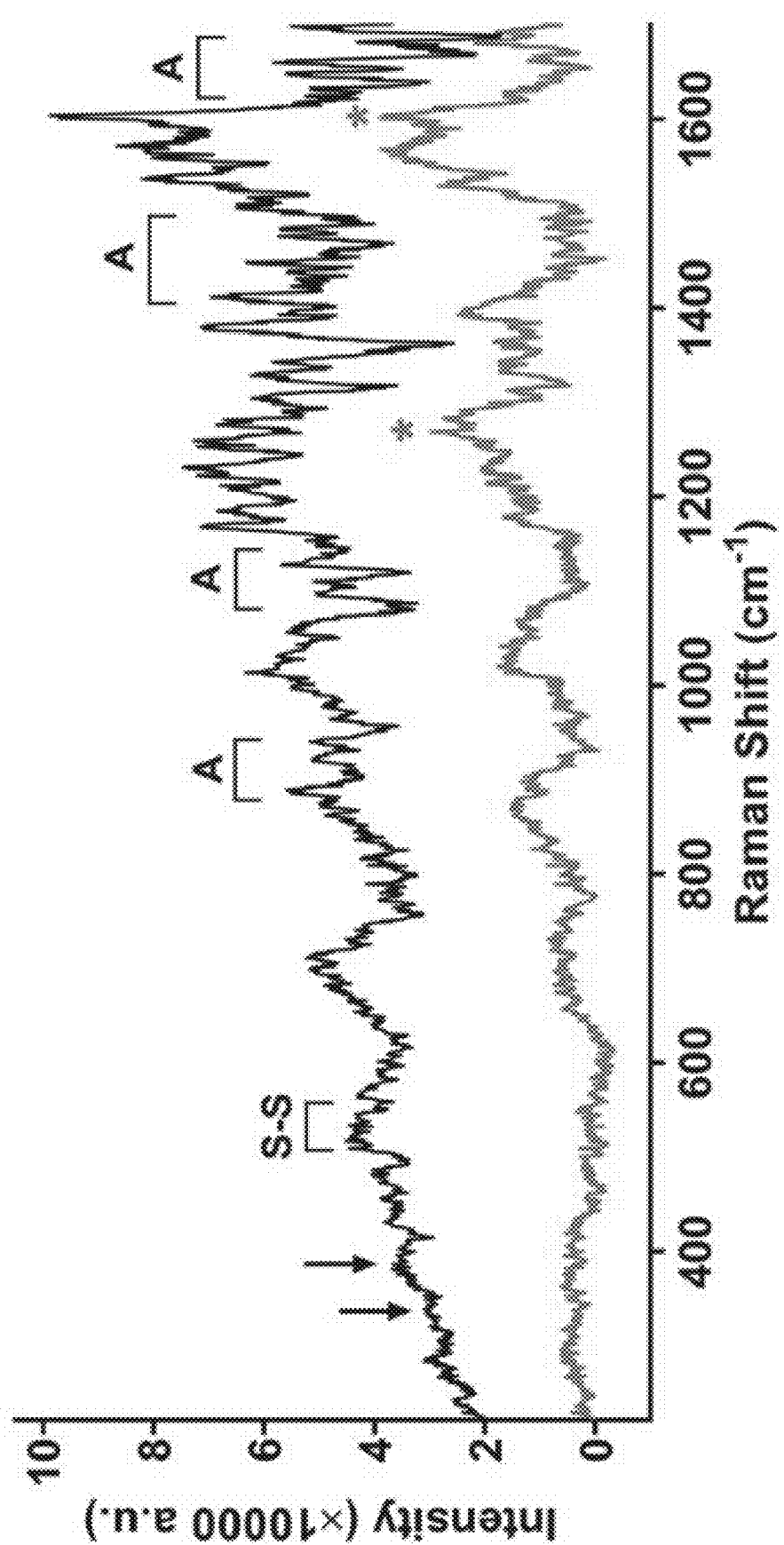

As shown in FIG. 7C, the Raman spectroscopy analysis indicated that ACE2 was immobilized on the Pd-NTF surface via Pd—S linkage with a "Braggite-like" Raman shift from 326 to 392 $cm^{-1}$. The Raman shifts from 500 to 1700 $cm^{-1}$ contained signals for the ACE2 protein and the PET substrate.

These results indicated that ACE2 could bind to the Pd-NTF surface within 20 min with only 0.8 µg. The ultrasensitive detection of Raman spectroscopy signals at low sample amounts in the current analysis may be attributed to the induction of a local surface plasmon resonance (LSPR) phenomenon and an enhanced surface electric field by the unique Pd metal nanostructure on the surface of the biosensing electrode. Furthermore, the enhanced surface electric field generated may reduce the surface impedance of the electrode, thereby elevating the sensitivity of signal detection in EIS.

In this EIS-based biosensing platform, the binding of viral S-protein (or a live virus) to the ACE2 immobilized on the Pd-NTF electrode and the interfering effects of pharmacological inhibitors were detected by monitoring the changes in the electrical impedance at the interface of the solution and S-protein/virus-ACE2-Pd-NTF electrode. Such electrical impedance can be determined by applying a small sinusoidal voltage at different frequencies to the S-protein/virus-ACE2-Pd-NTF electrode, followed by measuring the resulting sinusoidal current responses. Moreover, impedance was calculated based on the current-voltage ratio via an effective equivalent Randel's model[7], whereby the charge transfer resistance ($R_{ct}$) represented the impedance from the ACE2-spike binding.

Figure 8A:
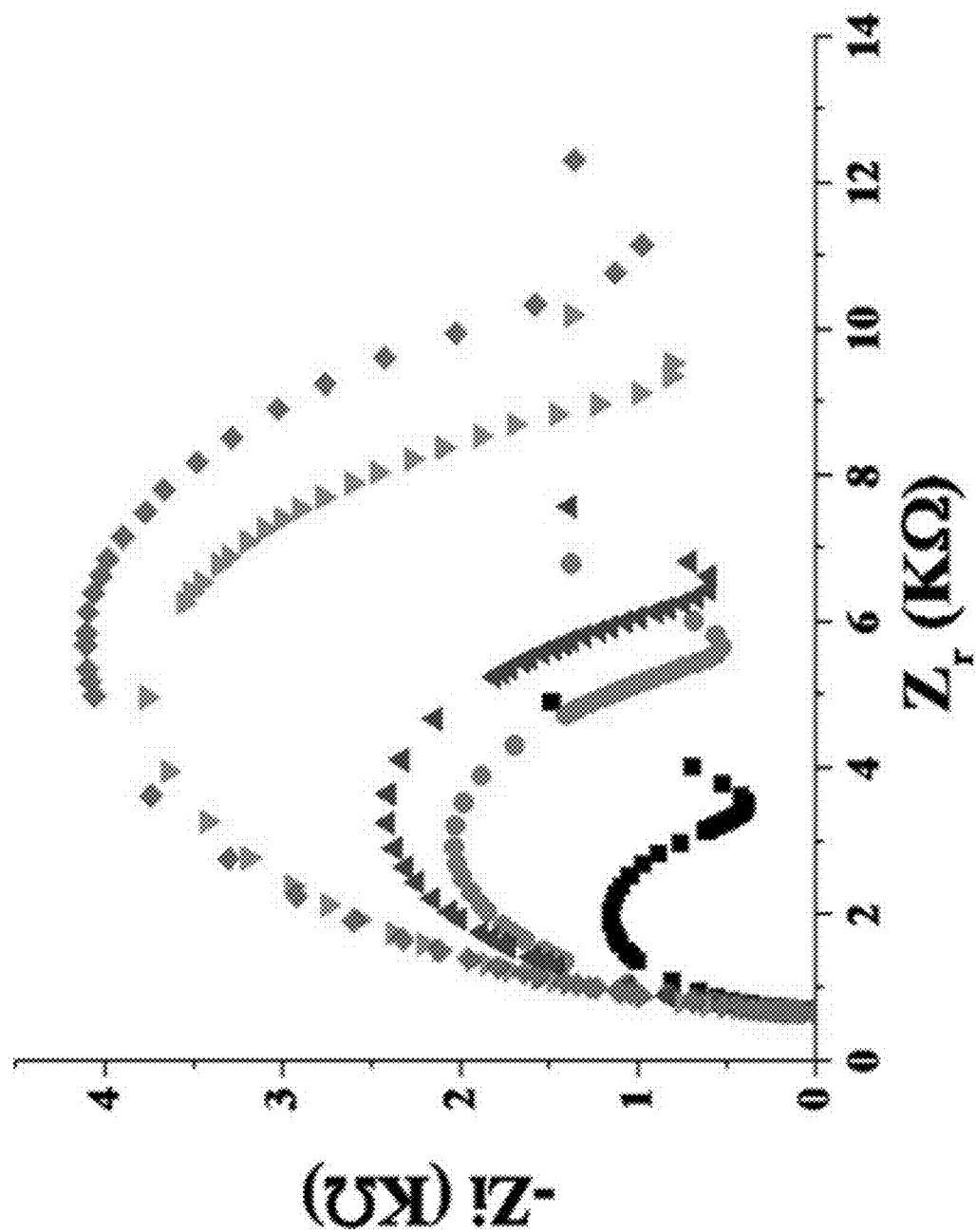
Figure 8B:
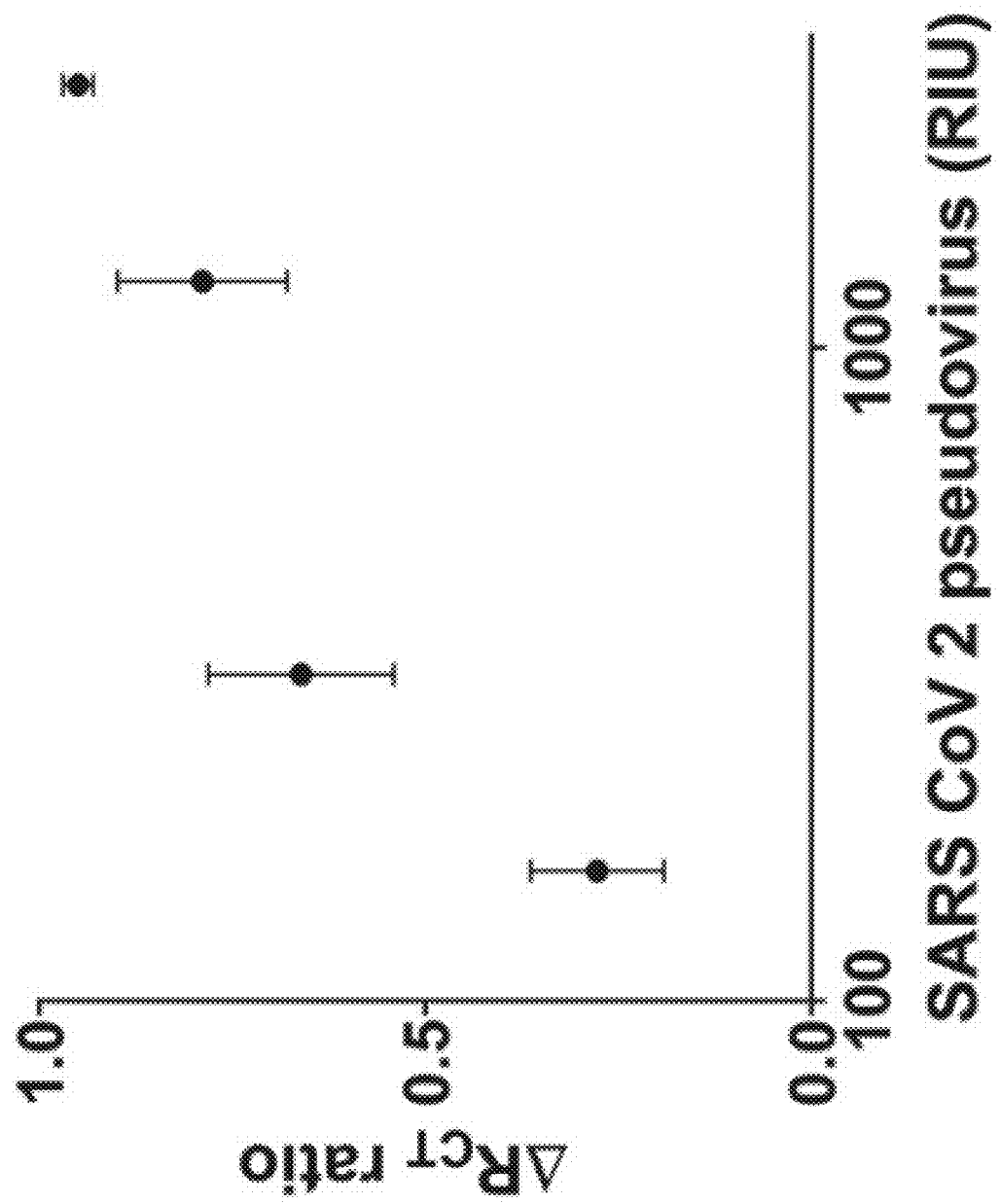
Figure 8C:
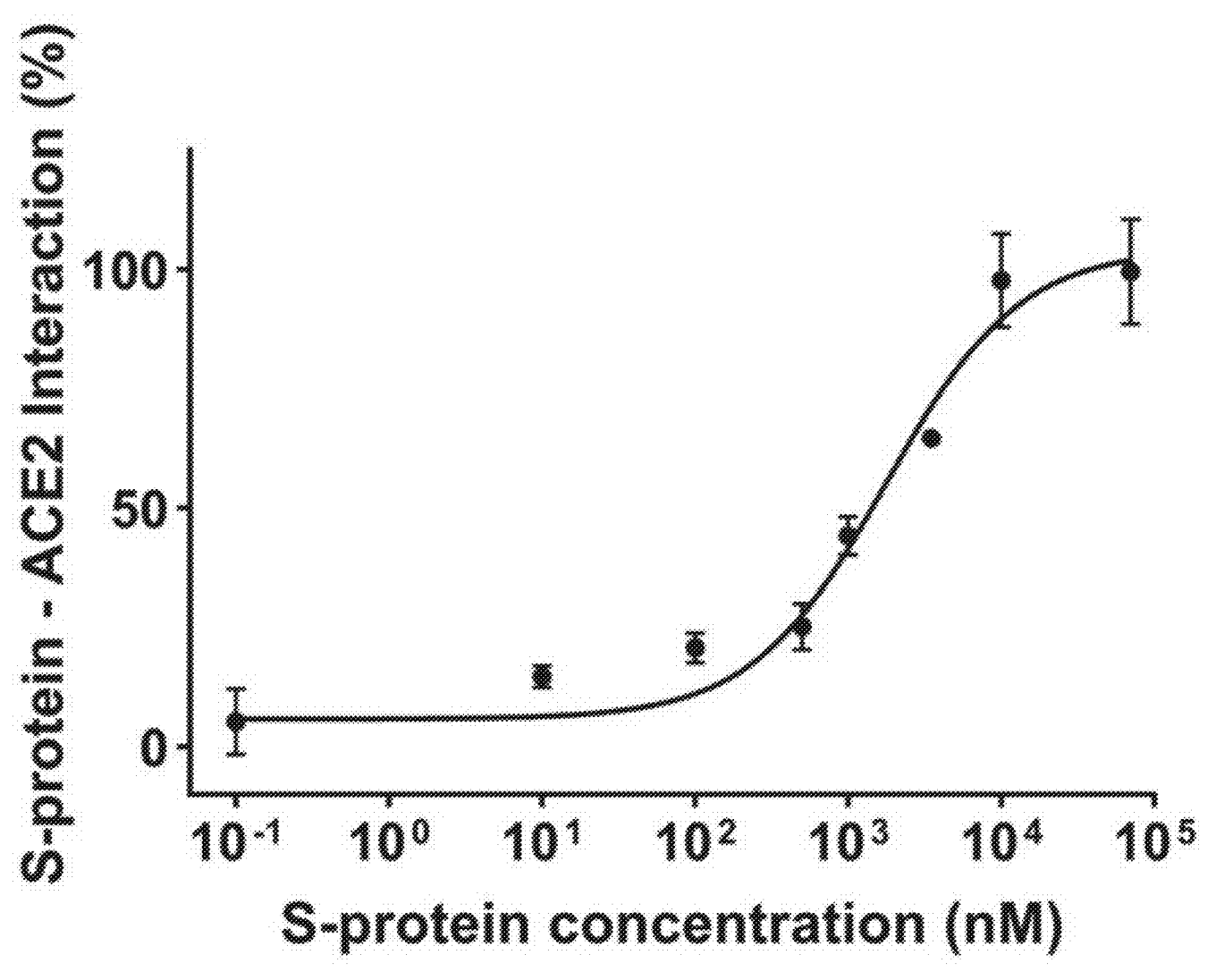

The capability of this EIS-biosensing setup in detecting the binding of SARS-CoV-2 to ACE2 was demonstrated through the successful documentation of the $R_{ct}$ changes following the exposure of the ACE2-coated electrode to an escalating concentration of SARS-CoV-2 pseudovirus (nCoV-S-Luc pseudovirus) (FIGS. 8A and 8B). Furthermore, in the case that the recombinant S-protein of SARS-CoV-2 was adopted as a model system to investigate the effect of pharmacological inhibitors on the interaction between S-protein and ACE2, a dose-response curve that represents the dose-dependent interaction of S-protein with the immobilized ACE2 (base-D-RC, $EC_{50\ S\text{-}protein\ @baseline}=1.74\pm0.31$ µM) (FIG. 8C) can also be generated through calculating the $R_{ct}$ changes before and after the S-protein (at different concentrations) interacts with ACE2 ($\Delta R_{ct}$). All statistical comparisons for $EC_{50}$ and $E_{max}$ values were done via One-Way Analysis of Variance (One-way ANOVA with Dunnett test, Graphpad Prism 8).

Example 3: Identification of SARS-CoV-2-ACE2 Binding Modulators Via EIS-Based Biosensing Platform To assess the modulating effects of ACE2-interacting peptide analogs of ACEi on 5-protein-ACE2 interaction, the surface of ACE2-Pd-NTFE was pre-treated with 1 µL of the peptide analogs of ACEi, such as enalapril, enalaprilat, lisinopril, captopril, perindopril, perindoprilat, ramipril and ramiprilat (prepared in PBS at a concentration of 0.1 to 4 µg/mL), as well as PBS (blank control) for 10 min at room temperature. The treated ACE2-Pd-NTFE was then gently rinsed with distilled water and drained dry, and then connected to the EIS device for impedance measurement. $R_{ct}$ values obtained from the treated ACE2-Pd-NTF electrode were taken as the baseline $R_{ct}$ for the respective treated ACE2-Pd-NTFE.

The ACEi-treated ACE2-Pd-NTFE was then exposed to a series of PBS solutions containing ascending concentrations of recombinantly-expressed SARS-CoV-2 S-protein (0.1 to 100 µM, 2 µL per electrode) for 10 min at room temperature, followed by EIS measurement. The net changes in $R_{ct}$ value ($\Delta R_{ct}$) were calculated by subtracting the baseline $R_{ct}$ signals of ACE2-Pd-NTF electrode from that treated with PBS of S-protein. All $\Delta R_{ct}$ values were further normalized and expressed as the percentage of S-protein-ACE2 interaction by using the $\Delta R_{ct}$ values of the PBS-control group and the saturated S-protein-treated group as the 0% and 100% S-protein-ACE2 interaction, respectively (GraphPad Prism 8.3 software). A dose-response curve (S-protein concentration vs. $\Delta R_{ct}$) was then plotted for the respective ACEi- and PBS-treated groups. The dose-response curves of the ACEi-treated groups were compared to those of the PBS-treated controls to assess the effect of the peptide analogs on the S-protein-ACE2 interaction.

Figure 9A:
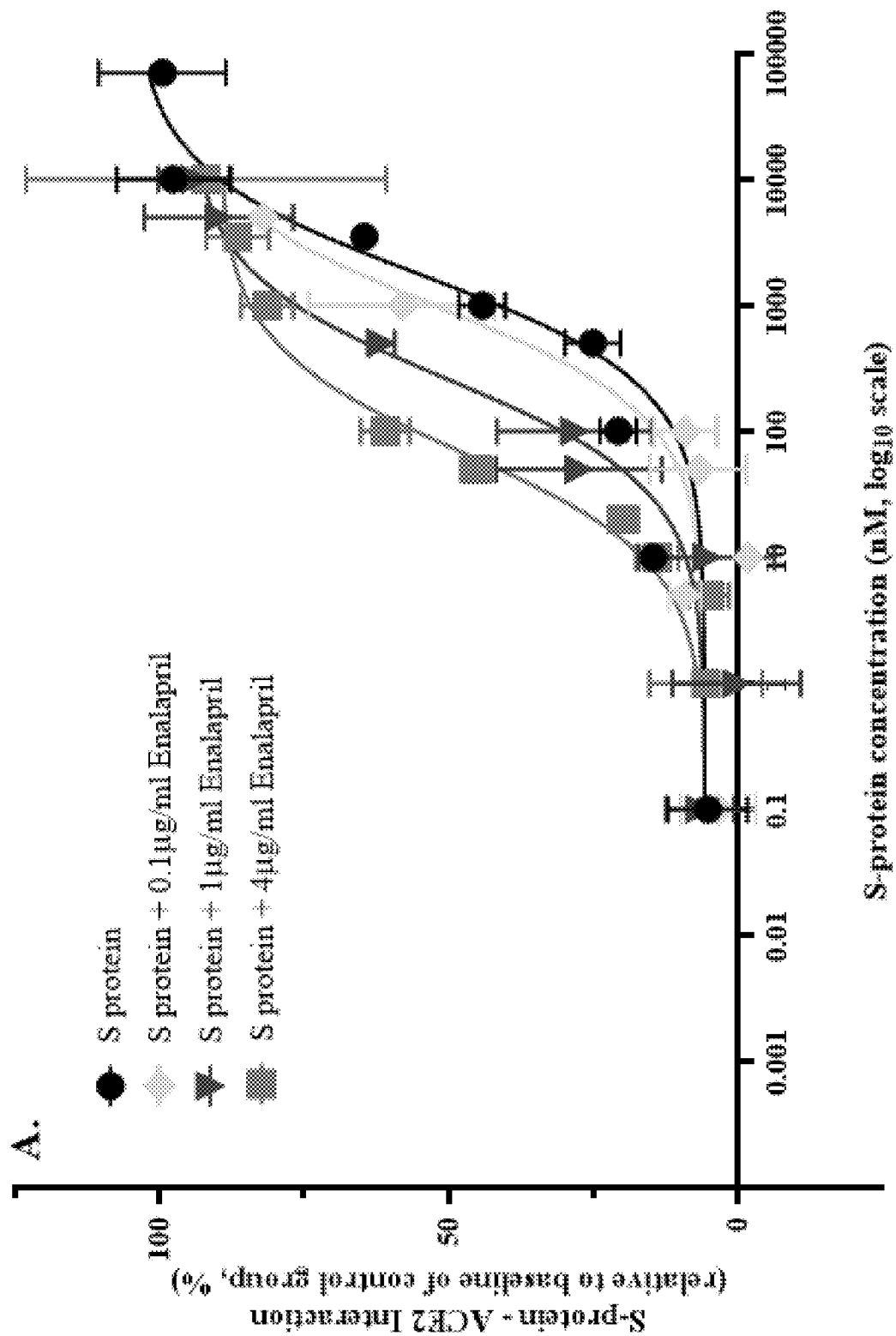

ACEi was found to exhibit paradoxical influences on S-protein-ACE2 binding. Firstly, the EIS-based biosensing platform surprisingly identified the positive modulators of the S-protein-ACE2 binding from among the peptide analogs tested. For example, enalapril positively modulated the S-protein-ACE2 binding at a dose dependent manner (FIG. 9A). At a dose of 4 µg/mL, enalapril increased the potency of S-protein binding to ACE2 by 25-fold ($EC_{50\ S\text{-}protein\ @enalapril}=0.07\pm0.01$ µM compared to $EC_{50\ S\text{-}protein\ @baseline}=1.74\pm0.31$ $p<0.001$), suggesting that the binding of enalapril to ACE2 has likely induced a change in the ACE2 conformation to promote S-protein binding.

Figure 9B:
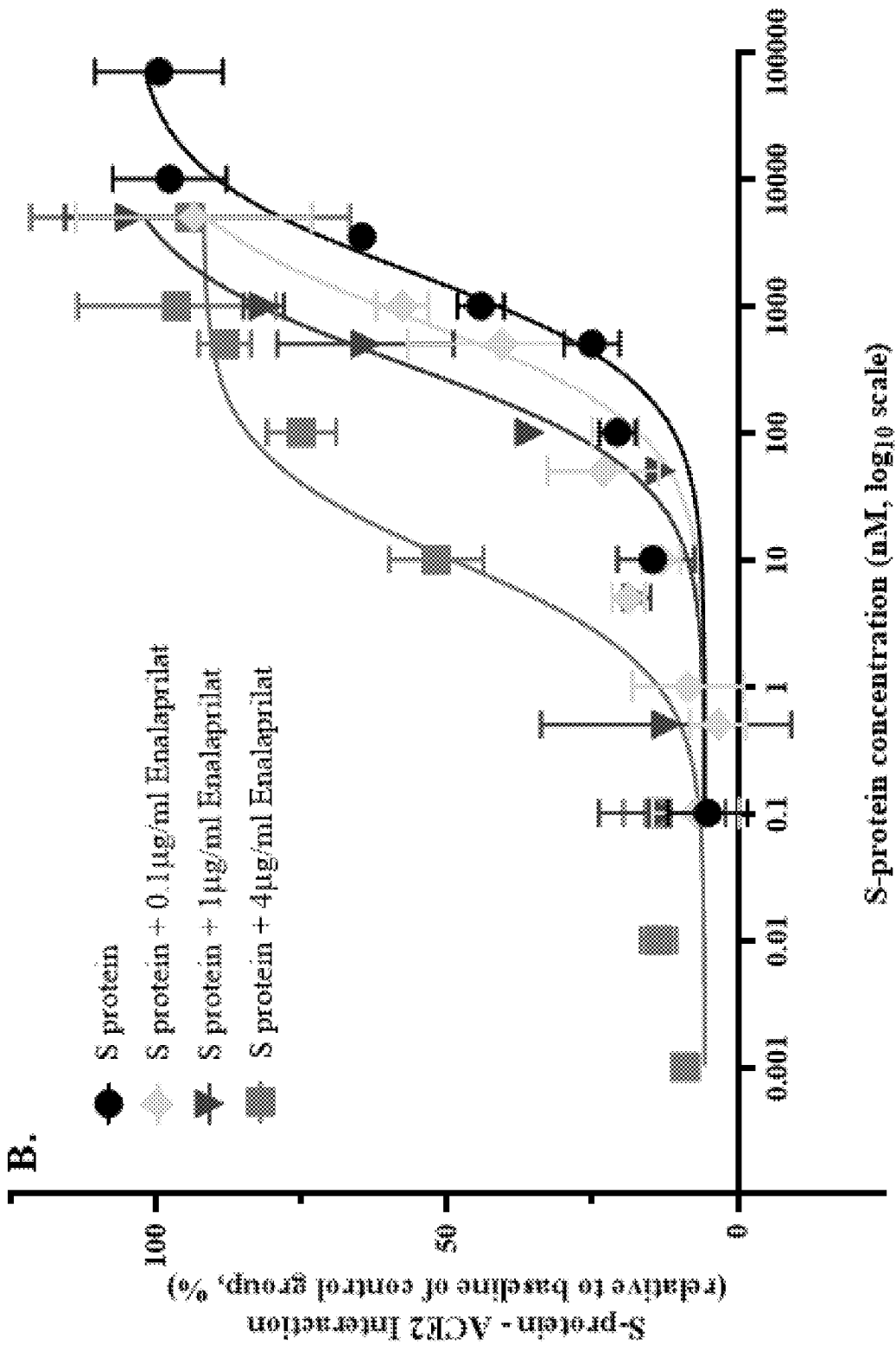

Enalapril is known to metabolize rapidly into its active metabolite enalaprilat post administration to patients. As shown in FIG. 9B, enalaprilat induced a dose-dependent positive modulation on S-protein-ACE2 binding much greater than that of enalapril. At a dose of 4 enalaprilat increased the potency of S-protein binding to ACE2 by approximately 174-fold ($EC_{50\ S\text{-}protein\ @enalaprilat}$=0.01±0.003 µM compared to $EC_{50\ S\text{-}protein\ @baseline}$=1.74±0.31 p<0.001). These results suggest that (i) modulation of the ACE2 conformation by ACEi is structure-dependent, (ii) metabolic conversion of enalapril to enalaprilat further enhances the binding of S-protein to ACE2, and (iii) the increase in the binding of S-protein to ACE2 is likely correlated to the metabolic conversion of the ethoxycarbonyl (—COO—$C_2H_5$) terminal of the glycine moiety of enalapril to —COOH terminal in acetone-glycine moiety of enalaprilat.

Figure 9C:
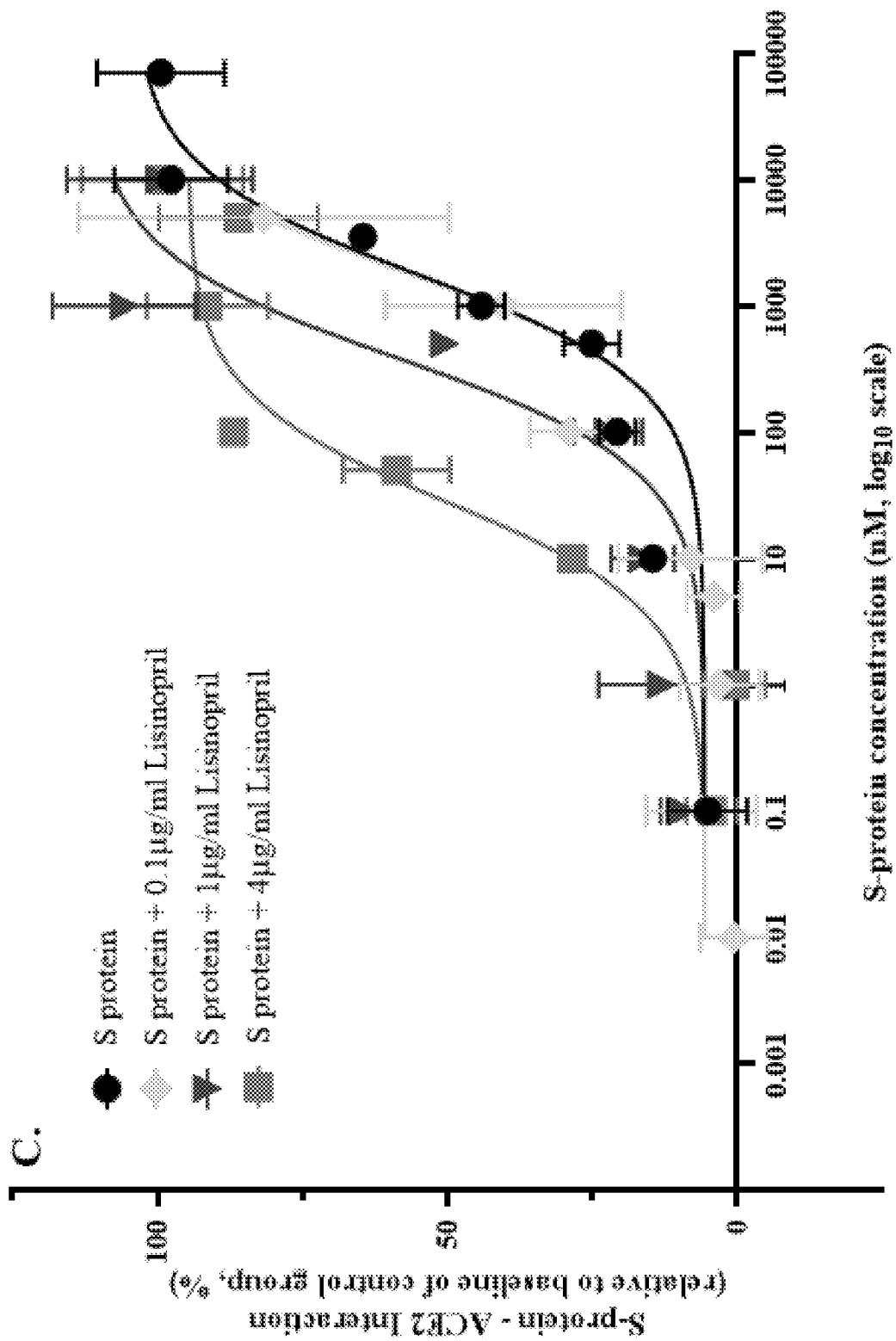

Lisinopril was found to exhibit a dose-dependent positive modulation on S-protein-ACE2 binding similar to that of enalapril and enalaprilat. At a dose of 4 µg/mL, lisinopril increased the S-protein-ACE2 binding potency by approximately 67-fold ($EC_{50\ S\text{-}protein\ @lisinopril}$=0.03±0.005 µM compared to $EC_{50\ S\text{-}protein\ @baseline}$=1.74±0.31 µM, p<0.001) (FIG. 9C). The extent of positive modulation by lisinopril is slightly lower than that of enalaprilat, but greater than enalapril.

The higher positive-modulation by lisinopril and enalaprilat may be attributed to the presence of an uncapped —COOH terminal on the glycine moiety, as opposed to the ethoxycarbonyl ($C_2H_5$)-capped terminal in enalapril. The weaker positive modulation effects of lisinopril compared to enalaprilat may be due to the presence of —$C_4H_8$—$NH_2$ side chain at the L-lysyl moiety, which affected the interaction of lisinopril with ACE2, and thus the ACE2 conformational change for better S-protein binding.

Figure 9D:
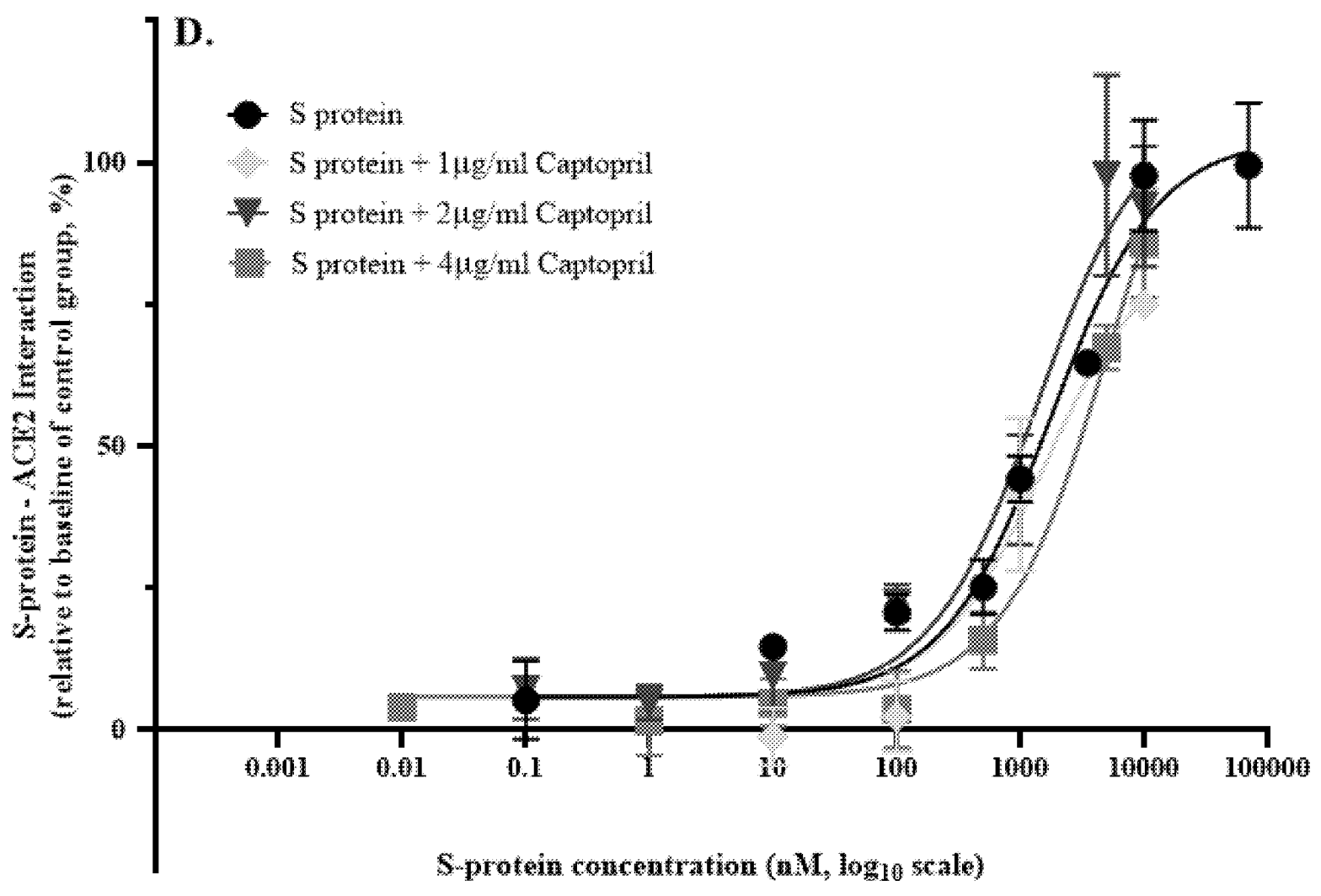

Meanwhile, captopril, an ACEi that is devoid of a glycine moiety in its chemical structure, did not cause statistically significant alterations to the S-protein-ACE2 binding profile at the highest dose tested (4 µg/mL, $EC_{50\ S\text{-}protein\ @captopril}$=5.1±2.62 µM compared to $EC_{50\ S\text{-}protein\ @baseline}$=1.74±0.31 p>0.05) (FIG. 9D). However, computational structural superimposition analysis has suggested that captopril no matter in its monomers or dimeric forms may form hydrogen/salt bridge bonding with ACE2 and thus affects the S-protein-ACE2 binding, implying that the observed loss of S-protein-ACE2 binding modulation by captopril may possibly be due to its chelation by the $Fe^{2+}$ ions in the electrolyte solution (containing $K_2Fe(CN)_6$) employed in this experiment (to interface the ACE2-coated electrode with the biosensing platform reference and counter electrodes).

Figure 10A:
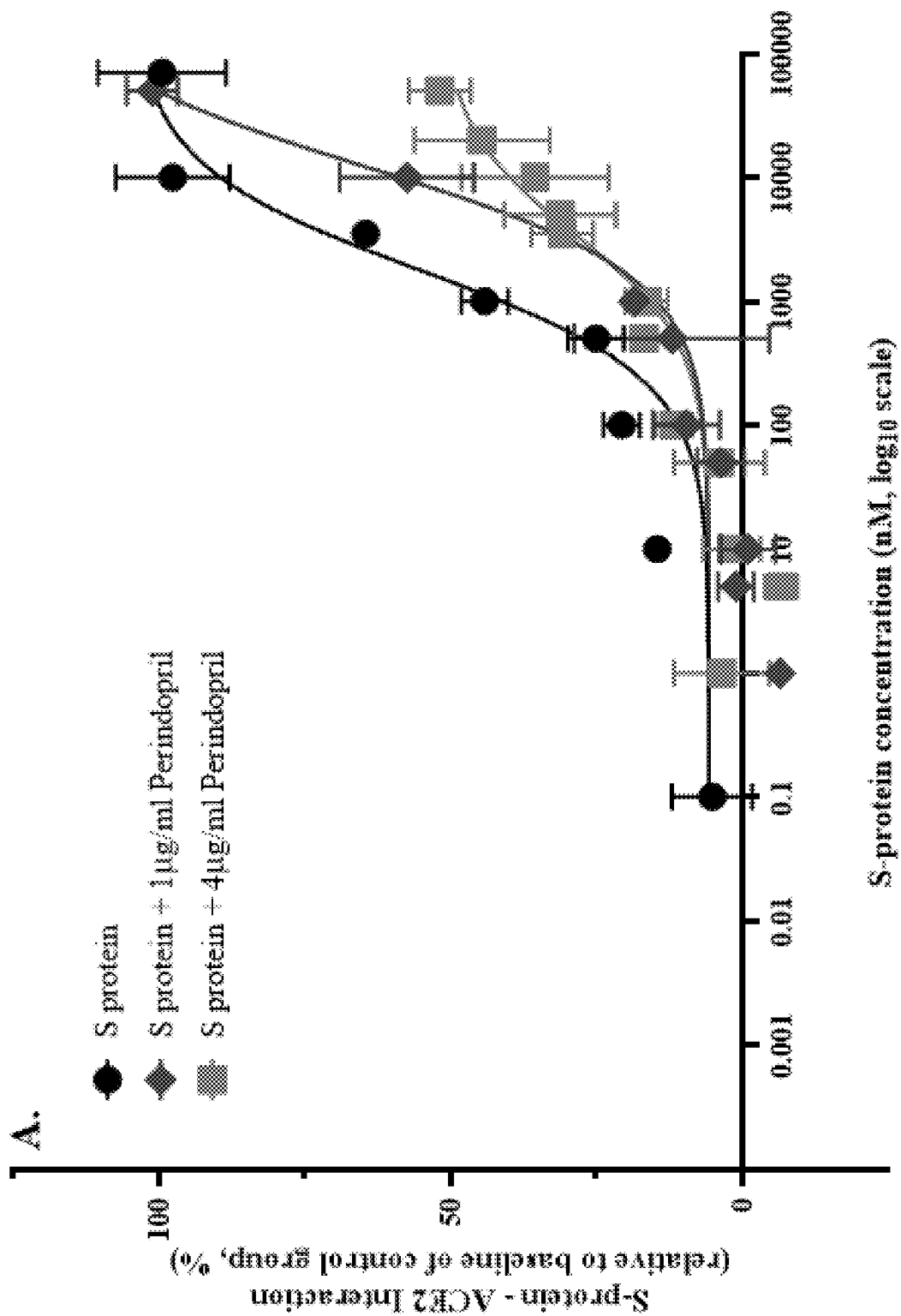
Figure 10B:
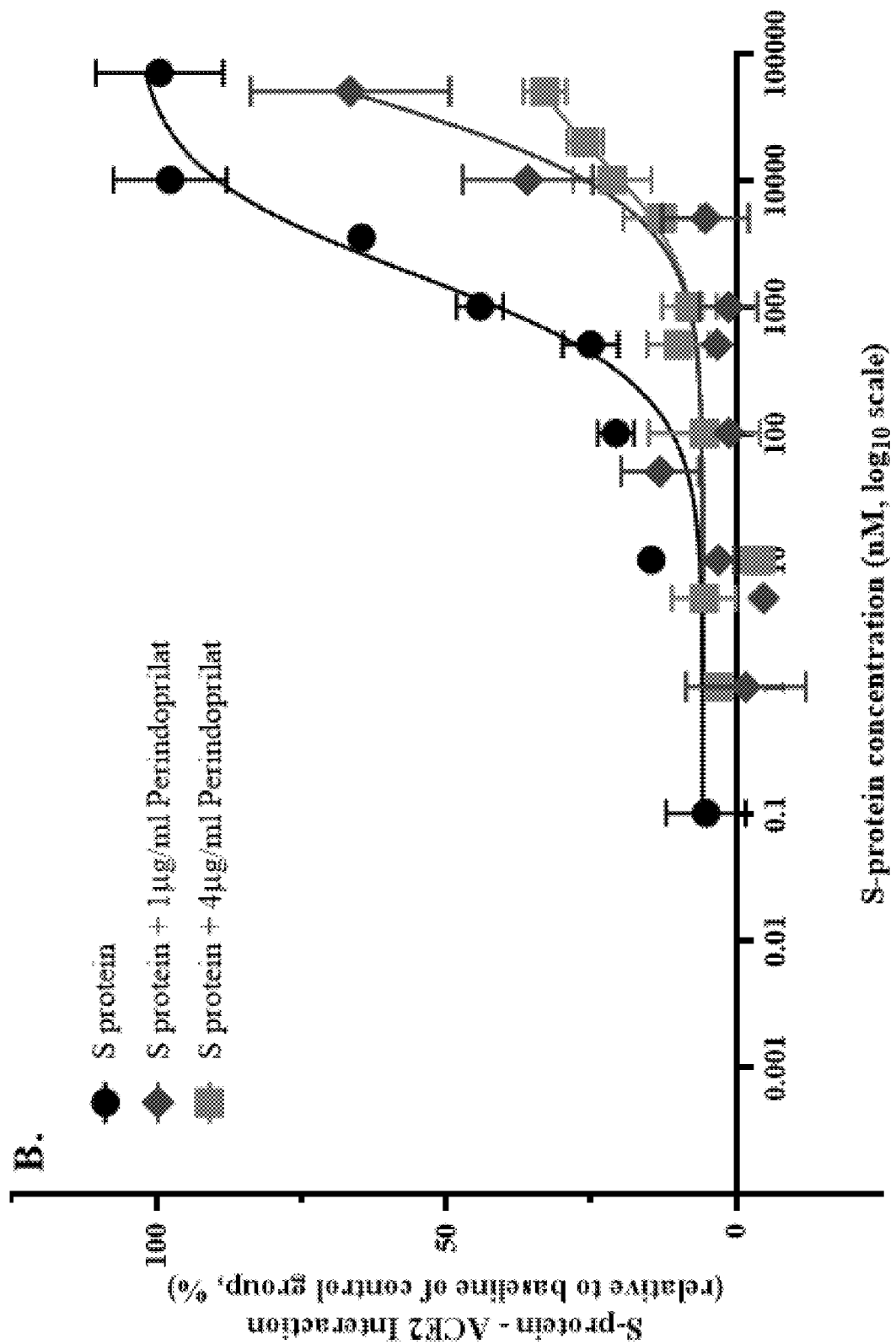

On the other hand, perindopril exerted an entirely opposite mode of modulation to the S-protein-ACE2 interaction compared to that of the above tested ACEi; that is, perindopril antagonized the binding of S-protein to ACE2 in a dose-dependent manner instead of positively modulating the binding activity (FIG. 10A). At a dose of 4 µg/mL, perindopril suppressed the S-protein-ACE2 interaction (at maximum S-protein concentration used in this experiment, $E_{max}$ S-protein) by approximately 48% ($EC_{max\ S\text{-}protein\ @perindopril}$=51.9±5.3% compared to $EC_{max\ S\text{-}protein\ @baseline}$=99.5%±11.0%, p<0.01). Perindoprilat, the active metabolite of perindopril, exhibited similar trends of inhibition against S-protein-ACE2 interaction. As shown in FIG. 10B, at 4 µg/mL, perindoprilat suppressed S-protein binding by 67% ($EC_{max\ S\text{-}protein\ @perindoprilat}$=33.0±3.7% compared to $EC_{max\ S\text{-}protein\ @baseline}$=99.5%±11.0%, p<0.0001), which was 19% stronger than that of the perindopril. These results further suggest the association between the presence of glycine-COOH moiety and the amplification of ACEi modulating effects to the S-protein-ACE2 binding (regardless of positive or negative modulation).

Comparing to enalapril, lisinopril and captopril, perindopril and perindoprilat possess two distinct structural features, i.e., a butyl-amino side chain instead of a 3-phenylpropyl side chain linking to its glycine moiety, and a 1H-indole-2-carboxylic acid moiety instead of an L-proline moiety. These results suggest that these distinctive structures may be correlated to the observed inversion of modulation of perindopril towards S-protein-ACE2 binding.

Figure 10C:
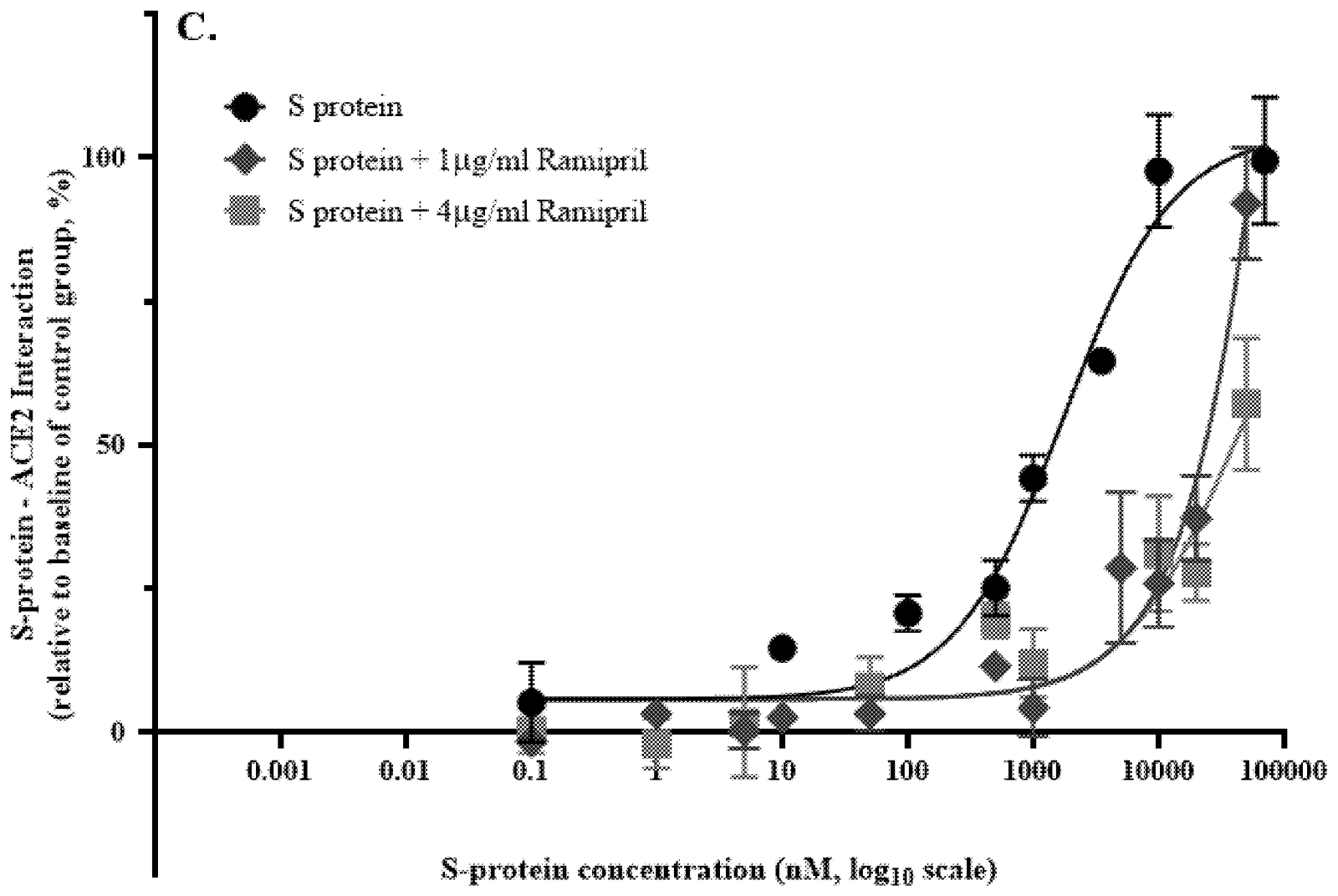
Figure 10D:
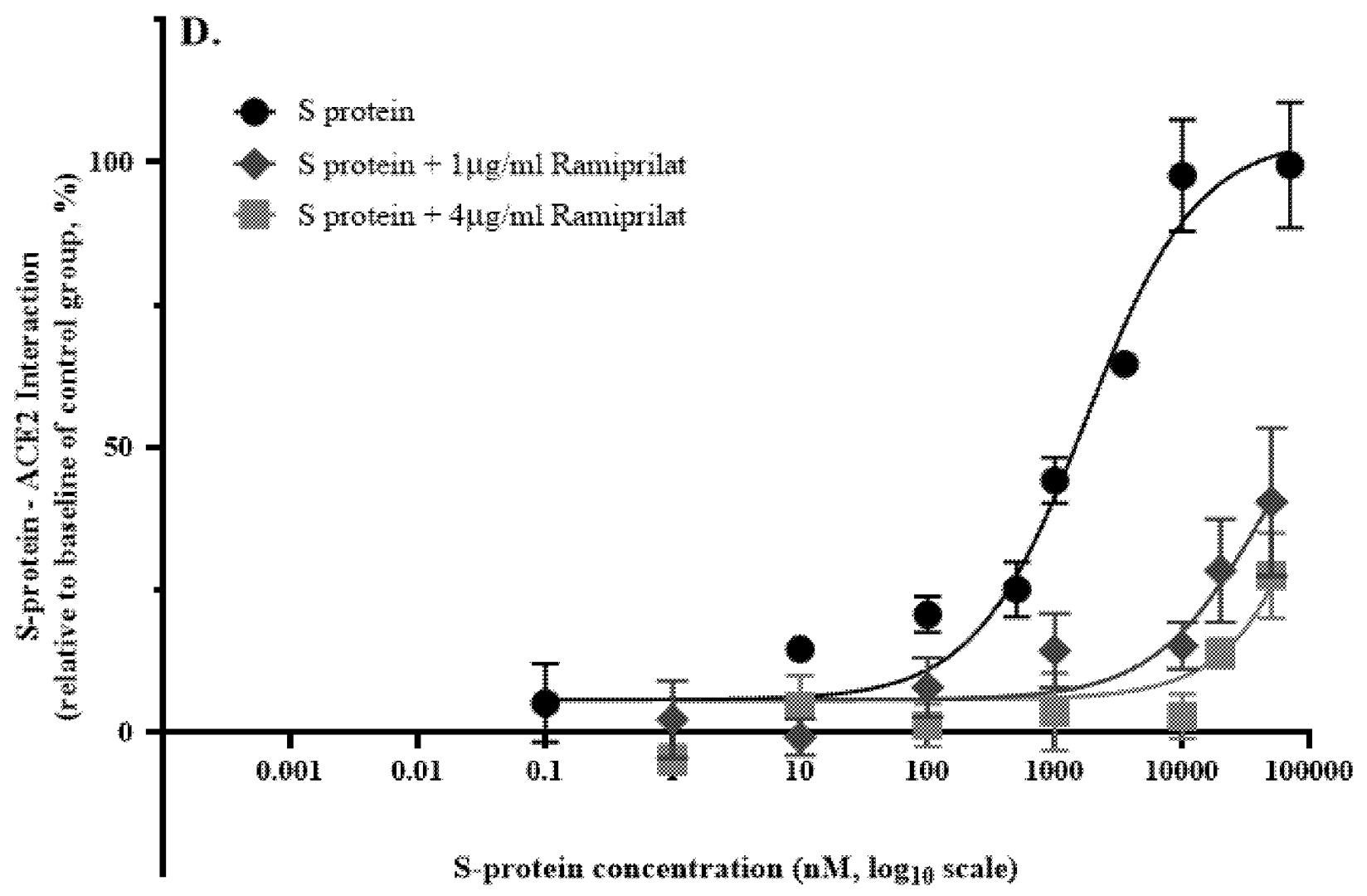

Assessments on the effect of ramipril and its metabolite ramiprilat to the S-protein-ACE2 binding provided further information pertaining to the chemical structure responsible for the ACEi antagonistic effects to the S-protein-ACE2 interaction. Similar to perindopril and perindoprilat, ramipril and ramiprilat antagonized the binding of S-protein to ACE2 at a dose-dependent manner (FIGS. 10C and 10D). At a dose of 4 µg/mL, ramipril suppressed the S-protein's ACE2 binding efficacy by approximately 42% ($EC_{max\ S\text{-}protein\ @ramipril}$=57.1±11.4% compared to $EC_{max\ S\text{-}protein\ @baseline}$=99.5%±11.0%, p<0.01) (FIG. 10C), while ramiprilat exhibited 30% stronger inhibition than that of the ramipril (72% suppression of S-protein-ACE2 maximum binding efficacy, $EC_{max\ S\text{-}protein\ @ramiprilat}$=27.6±7.5% compared to $EC_{max\ S\text{-}protein\ @baseline}$=104.2%±4.8%, p<0.01) (FIG. 10D).

Ramipril possesses a 3-phenylpropyl-glycine moiety similar to that of enalapril and lisinopril, and a cyclopenta[b]pyrrole-2-carboxylic acid moiety that resembles the 1H-indole-2-carboxylic acid moiety of perindopril and perindoprilat. These results suggest that such antagonistic effect of ramipril is mainly contributed by the presence of the bulky group of the rigid fused ring structure in the ACEi, instead of the structural difference at the side chain of the glycine moiety. Similar bulky group of the rigid fused ring (1H-indole-carboxylic acid moiety) was also found in perindopril and perindoprilat.

From the above, both active metabolites of perindopril and ramipril exhibited stronger suppressive effects than the parent compounds. These findings indicated correlations of the suppressive activities to the metabolic alteration of the inhibitors' chemical structures. Moreover, it suggests the potential of perindopril and ramipril and their metabolites as pharmacological inhibitors of the SARS CoV-2-ACE2 binding.

Example 4: Binding Selectivity of S-Protein to Pd-NTF Electrodes Under Different Conditions To verify the binding selectivity of the S-protein to the ACE2-Pd-NTF electrode, the binding of the S-protein to the plain and non-ACE2 protein-coated Pd-NTF electrodes (in the absence and presence of selected model drugs, i.e., perindoprilat and lisinopril) were assessed by incubating ascending concentrations of S-protein with:

(i) plain Pd-electrode in the absence of peptide analogues;

(ii) plain Pd-electrode in the presence of peptide analogues (one inhibitor, i.e., perindoprilat, and one positive modulator, i.e., lisinopril);

(iii) lysozyme-coated Pd-electrode in the absence of peptide analogues; or (iv) lysozyme-coated Pd-electrode in the presence of peptide analogues (one inhibitor, i.e., perindoprilat, and one positive modulator, i.e., lisinopril), followed by the determination of the impedance change before and after incubation ($\Delta R_{ct}$).

Figure 11A:
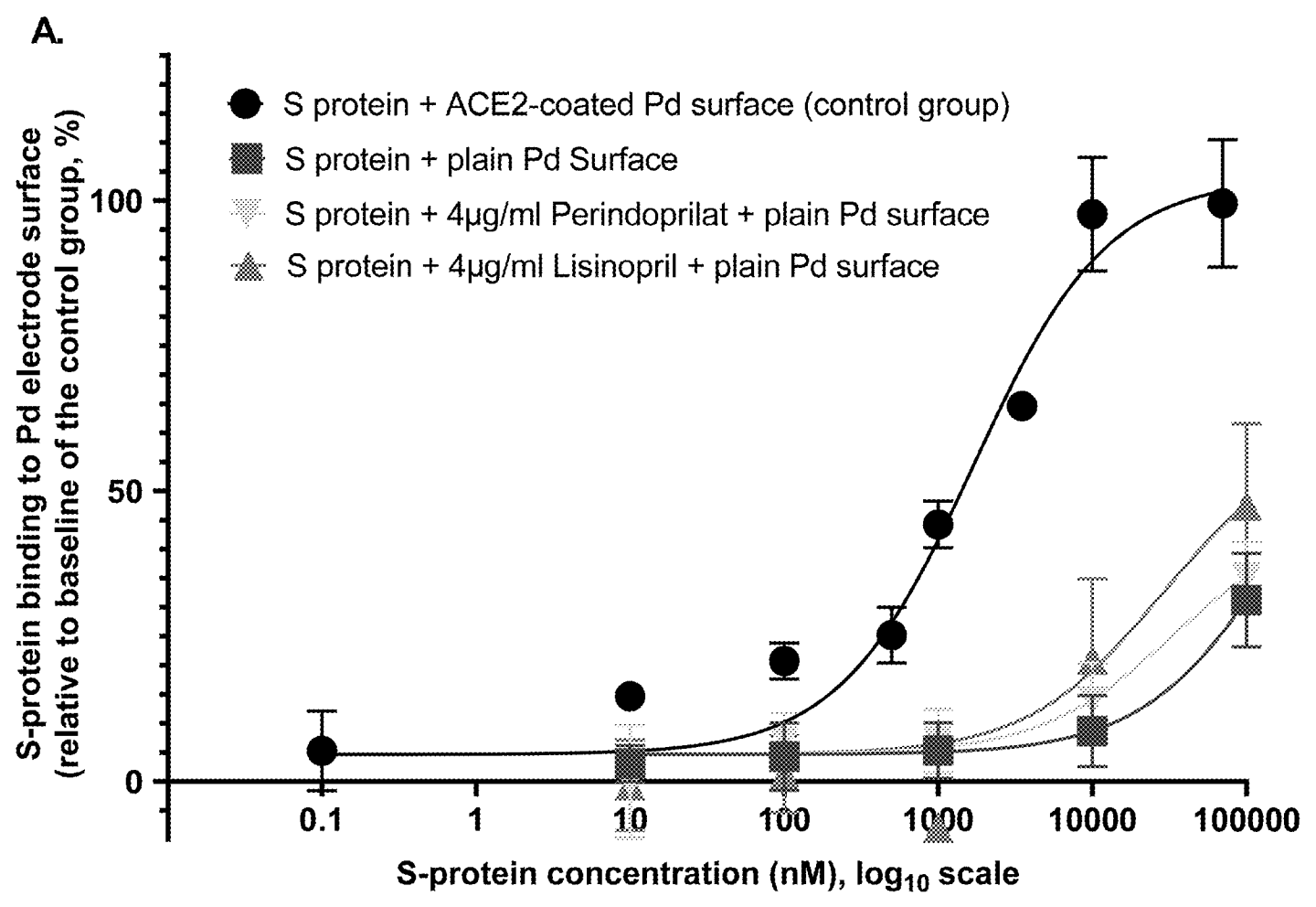
Figure 11B:
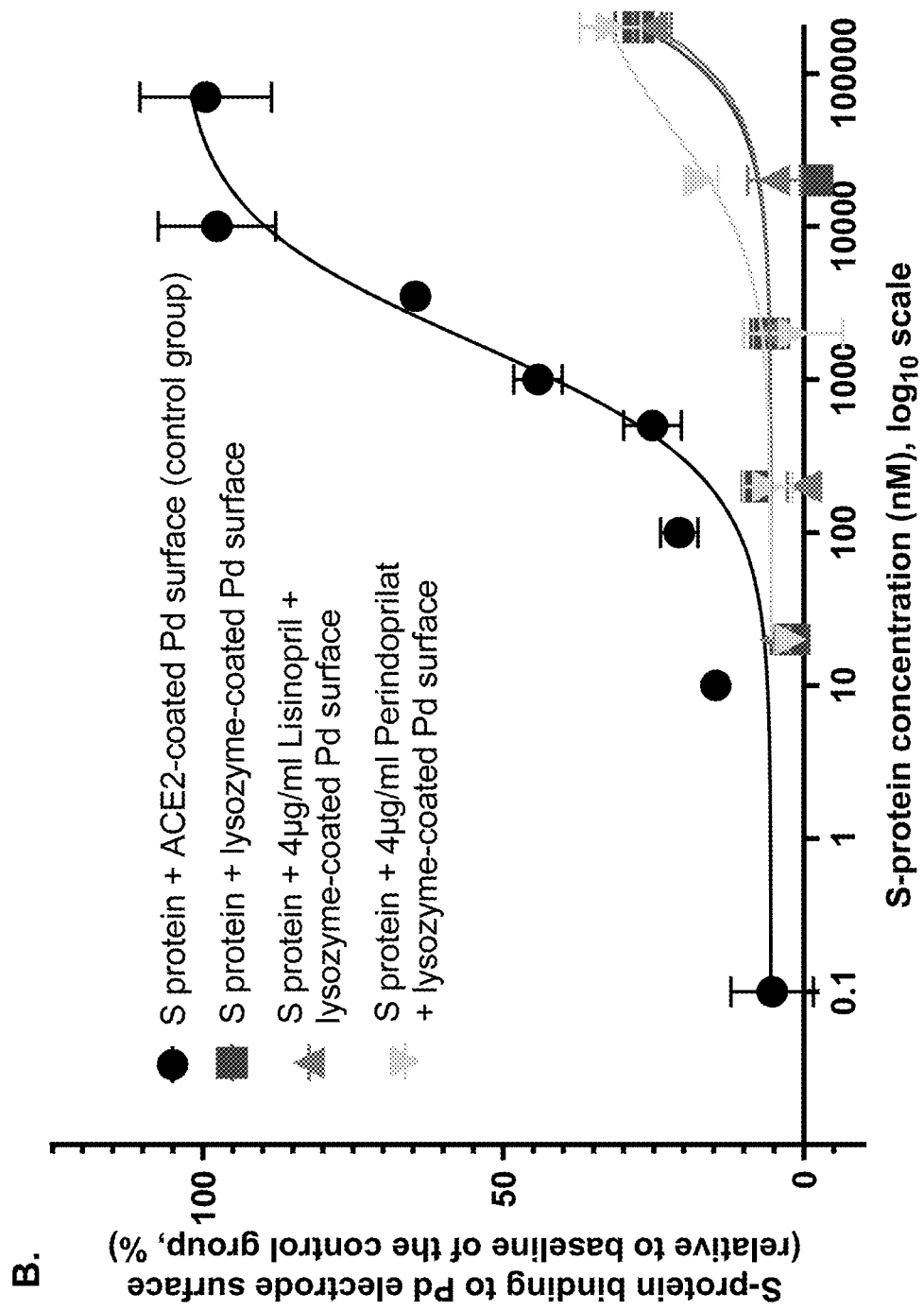

The binding of the S-protein to the plain Pd-NTF electrodes (FIG. 11A) and lysozyme-coated Pd-NTF electrodes (FIG. 11B) was observed only at high S-protein concentrations (both at more than 100 µM) and at a much lower efficiency (68.8% and 72.5% lower than that generated when the S-protein was incubated with ACE2-Pd-NTFE). The presence of perindoprilat and lisinopril did not change the binding patterns of the S-protein to the bare and lysozyme-coated Pd-NTF electrodes (FIGS. 11A and 11B). These results indicated non-selective interactions of the S-protein with both the plain and lysozyme-coated Pd-NTF electrodes.

Figure 11C:
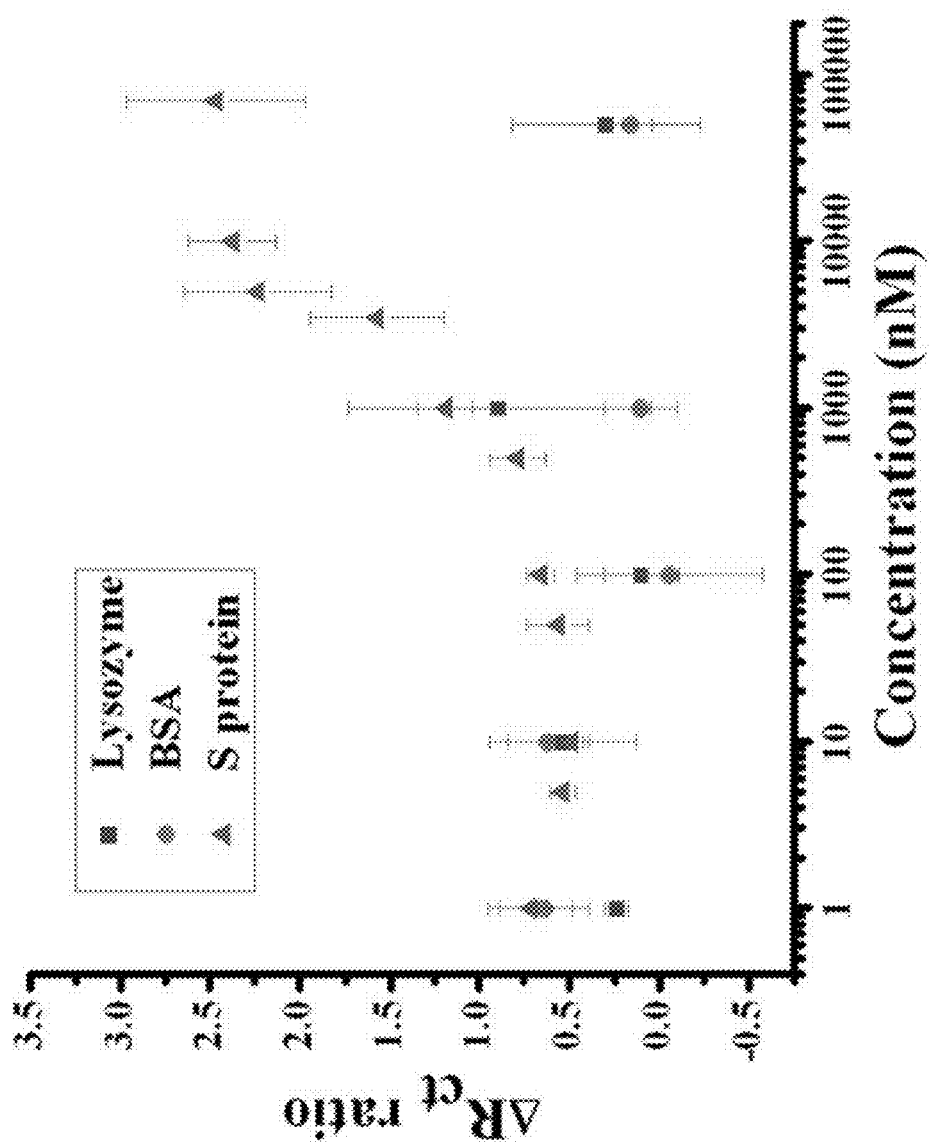

The ligand binding selectivity of the ACE2-Pd-NTFE was tested by incubating the ACE2-Pd-NTFE with ascending concentrations of S-protein, albumin, and lysozyme, followed by the determination of the impedance change before and after the incubation ($\Delta R_{ct}$). Concentration-dependent escalation in $\Delta R_{ct}$ was observed when the ACE2-Pd-NTFE was exposed to increasing concentrations of S-protein, except when it was exposed to increasing concentrations of albumin or lysozyme (FIG. 11C). These results suggested selective interaction of S-protein with ACE2 protein-coated Pd-NTF electrodes.

Example 5: Effect of ACEi on the In Vitro Replication of SARS-CoV-2

The modulation of ACE2-S-protein binding by the selected ACEi was evaluated with an in vitro SARS-CoV-2 infectivity study. In this example, ACE2-expressing human oral cavity squamous cell carcinoma cells (OEC-M1) were pretreated with ACEi, followed by incubating with quantum dot-labelled S-protein (QD-S-protein).

(5.1) Cell Culture and Western Blot Analysis

OEC-M1 cells were cultured in RPMI 1640 medium supplemented with 10% fetal bovine serum (FBS), 100-unit penicillin, 100 µg streptomycin, and 0.25 µg amphotericin B (Fungizone) (all from Gibco, Thermo Fisher, Waltham, MA, USA) per milliliter. The cells were seeded into a 6-well plate at a density of $3 \times 10^5$ cells/well for 18 hours at 37° C. and 5% $CO_2$ before treatment.

The expression of ACE2 in OEC-M1 cells in the absence or presence of selected peptide analogs (after 30 or 60 min of treatment at 20 µM) was evaluated by western blotting. Briefly, the cells were lysed in lysis buffer (20 mM Tris-HCl pH 7.5, 150 mM NaCl, 2 mM ethylenediaminetetraacetic acid (EDTA), and 1% Triton X-100) to obtain crude extract. The proteins were subjected to 10% SDS-PAGE and transferred onto a PVDF membrane (Millipore, Burlington, MA, USA) in a wet transfer system (Bio-Rad, Hercules, CA, USA) for 120 min at 400 mA. The PVDF membrane was then incubated in blocking solution (5% milk powder in PBS containing 0.1% Tween 20), followed by probing with primary antibodies (rabbit anti-ACE2 (ab108252, 1/1000 dilution, Abcam, Cambridge, UK) and mouse anti-α-tubulin (GTX628802, 1/20,000 dilution, GeneTex, Irvine, CA, USA)). Anti-mouse and anti-rabbit IgG-conjugated horseradish peroxidase antibodies (1:10,000) were used as secondary antibodies. Peroxidase activity was visualized using Enhanced Chemiluminescence Kit (Millipore, Burlington, MA, USA). Chemiluminescence imaging was performed using a BioSpectrum Imaging System (UVP, USA), and densitometric analyses were performed using AlphaImager 2200 software (ProteinSimple, Santa Clara, CA, USA).

Figure 12:
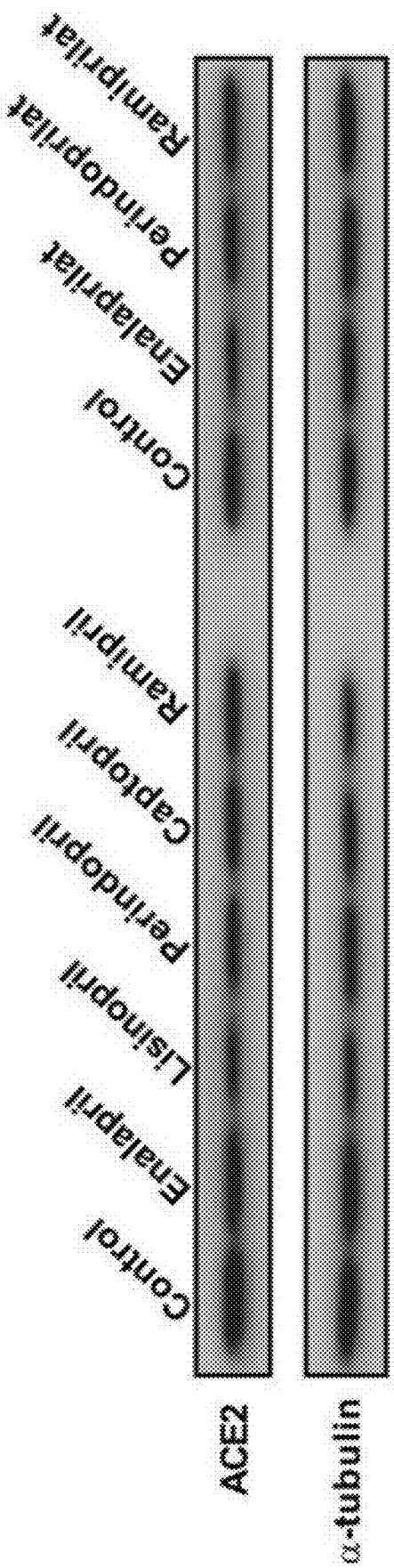
FIG. 12 shows the expression of ACE2 by human oral cavity squamous cell carcinoma cells (OEC-M1 cells) in the absence or presence of various selected peptide analogs (30- and 60-min pre-treatment at 20 μM respectively).

The results of western blot analysis were shown in FIG. 12, implying that ACE2 expression was not affected by treatment with the selected peptide analogs.

(5.2) Preparation of S-Protein Conjugated Quantum Dot (QD-S-Protein)

Figure 13:
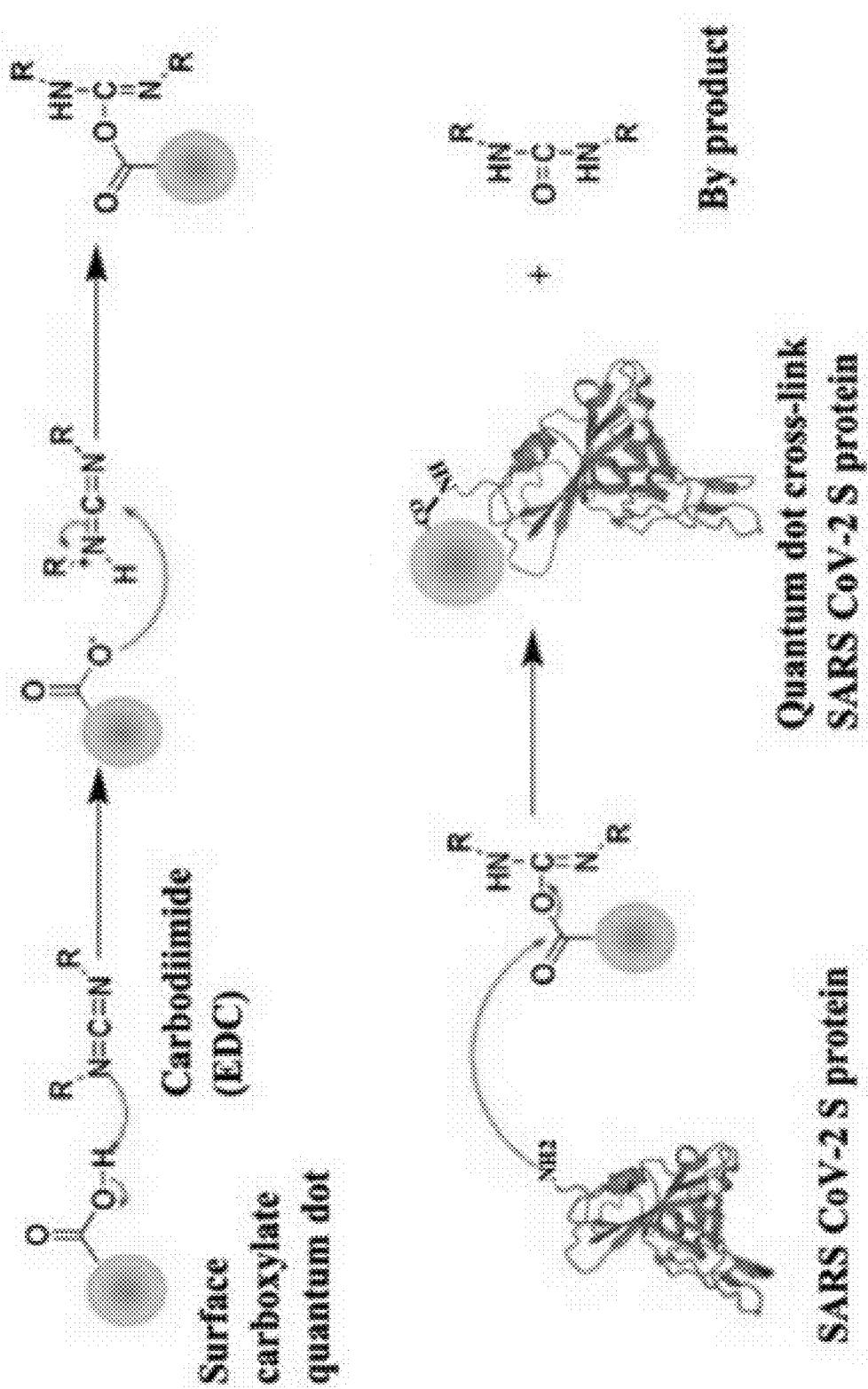
FIG. 13 shows a diagram illustrating the preparation of S-protein conjugated quantum dot (QD-S-protein).

A cadmium selenide core-zinc oxide shell (CdSe@ZnO) quantum dot (QD) (particle size about 2.5 nm, excitation and emission wavelengths at 400 and 525 nm, respectively) was a gift from Professor Dai-wen Pang of Nankai University, China[8]. The QD-labeling of S-protein was done by adding carboxyl-modified QD to the S-protein at a molar ratio of 1:5 in 500 µL of deionized water containing 0.1 M 1-ethyl-3-(3-dimethylaminopropyl) carbodiimide (EDC, Merck KGaA, St. Louis, MI, USA). The reaction mixture was then incubated for 12 hours at 4° C. on a rotating wheel in the dark. Thereafter, the reaction mixture was dialyzed in a dialysis tube with 3 kDa molecular weight cut-off against 50 mM Tris-HCl buffer (pH 7.5) for three rounds (10 hours/round) to remove excess EDC from the mixture. Estimation of the QD-labeled S-protein concentration in the dialyzed product was then performed via UV spectroscopy (at a wavelength of 280 nm with the S-protein extinction coefficient (ε) of 45,240 $M^{-1}cm^{-1}$). The mechanism of QD labeling of the S-protein was illustrated in FIG. 13.

(5.3) Confocal Microscopy for S-Protein Uptake by OEC-M1 Cells

To detect S-protein uptake by OECM-1 cells, the cells were seeded on glass cover slides in 24-well plates and left to attach overnight. The cells were then treated with 800 nM purified QD-S-protein for 30, 60, and 120 min. After removing QD-S-protein from the medium and washing thrice with PBS, the cells were fixed with 4% paraformaldehyde. Fluorescent and cellular morphology images were captured with a digital camera and a charge-coupled device image sensor with a differential interference contrast channel (FluoView FV1000, Olympus, Tokyo, Japan). High-resolution images were scanned from bottom to top (z-sections) to evaluate QD-S-protein in vitro binding.

Figure 14A:
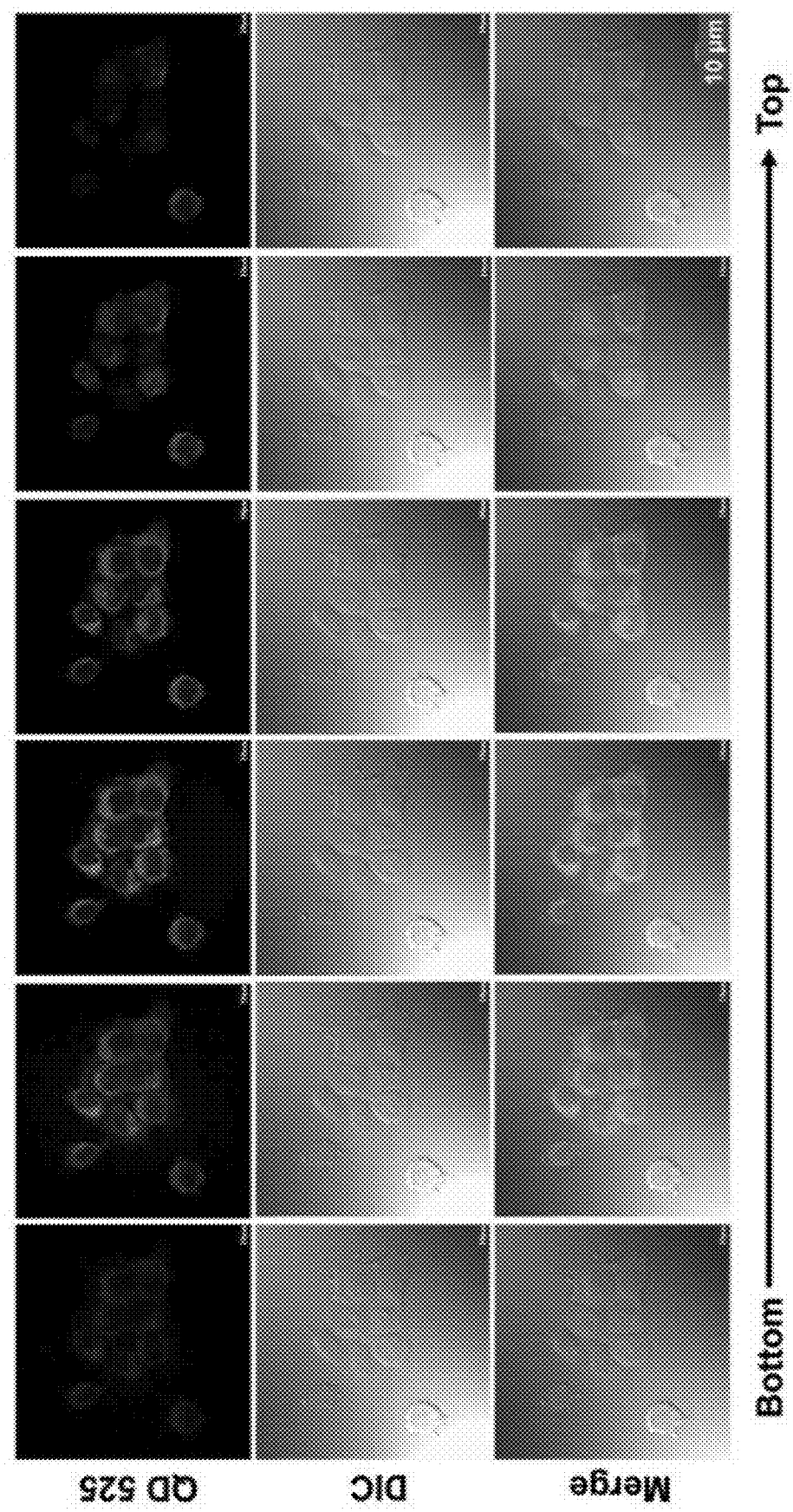
FIGS. 14A to 14C show the Z-stack confocal microscopic images (1 μm slicing), differential interference contrast (DIC) and merged images of OEC-M1 cells after treated with QD-S-protein for 30 min (FIG. 14A), 60 min (FIG. 14B) and 120 min (FIG. 14C).
Figure 14B:
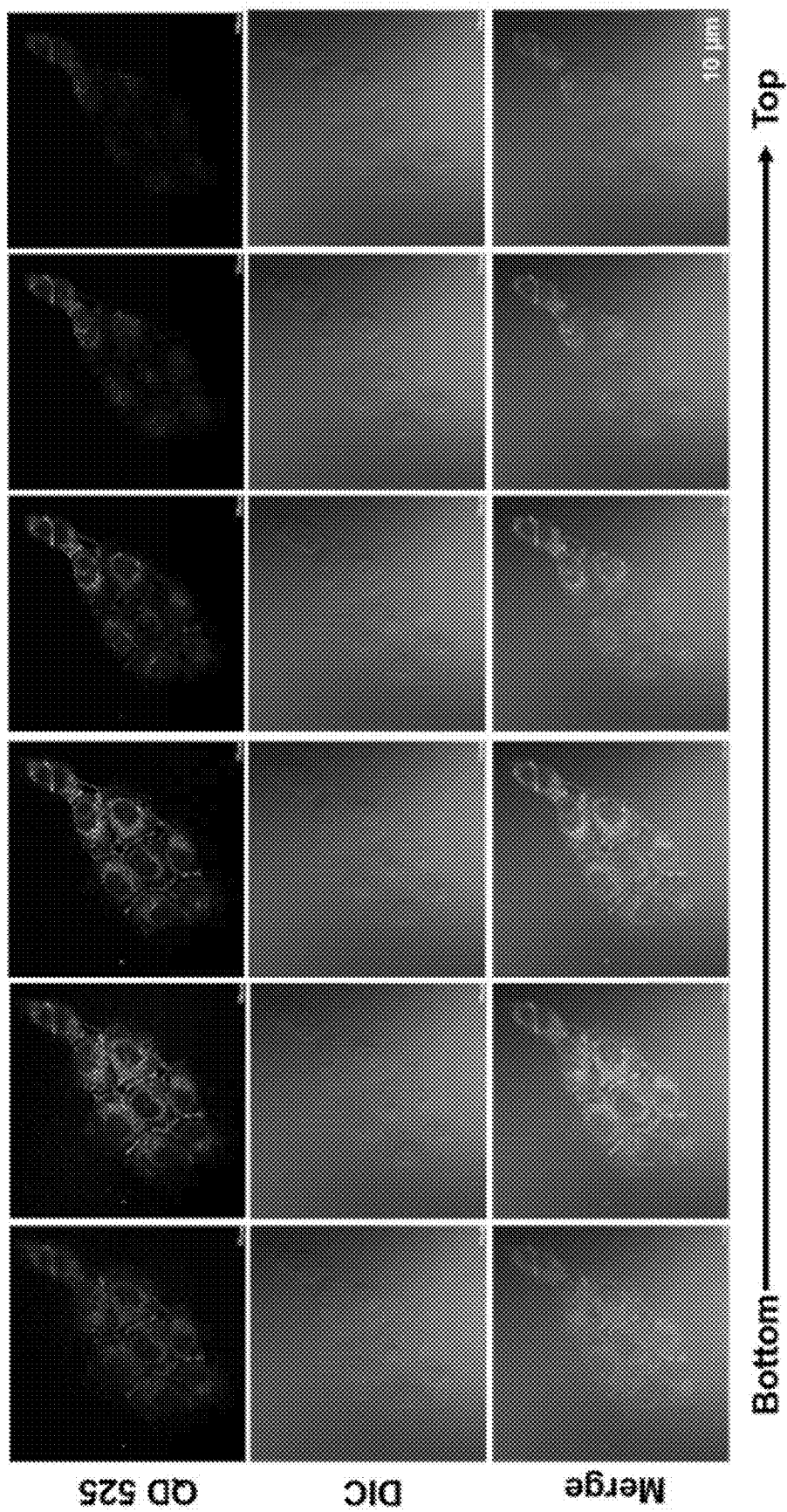
Figure 14C:
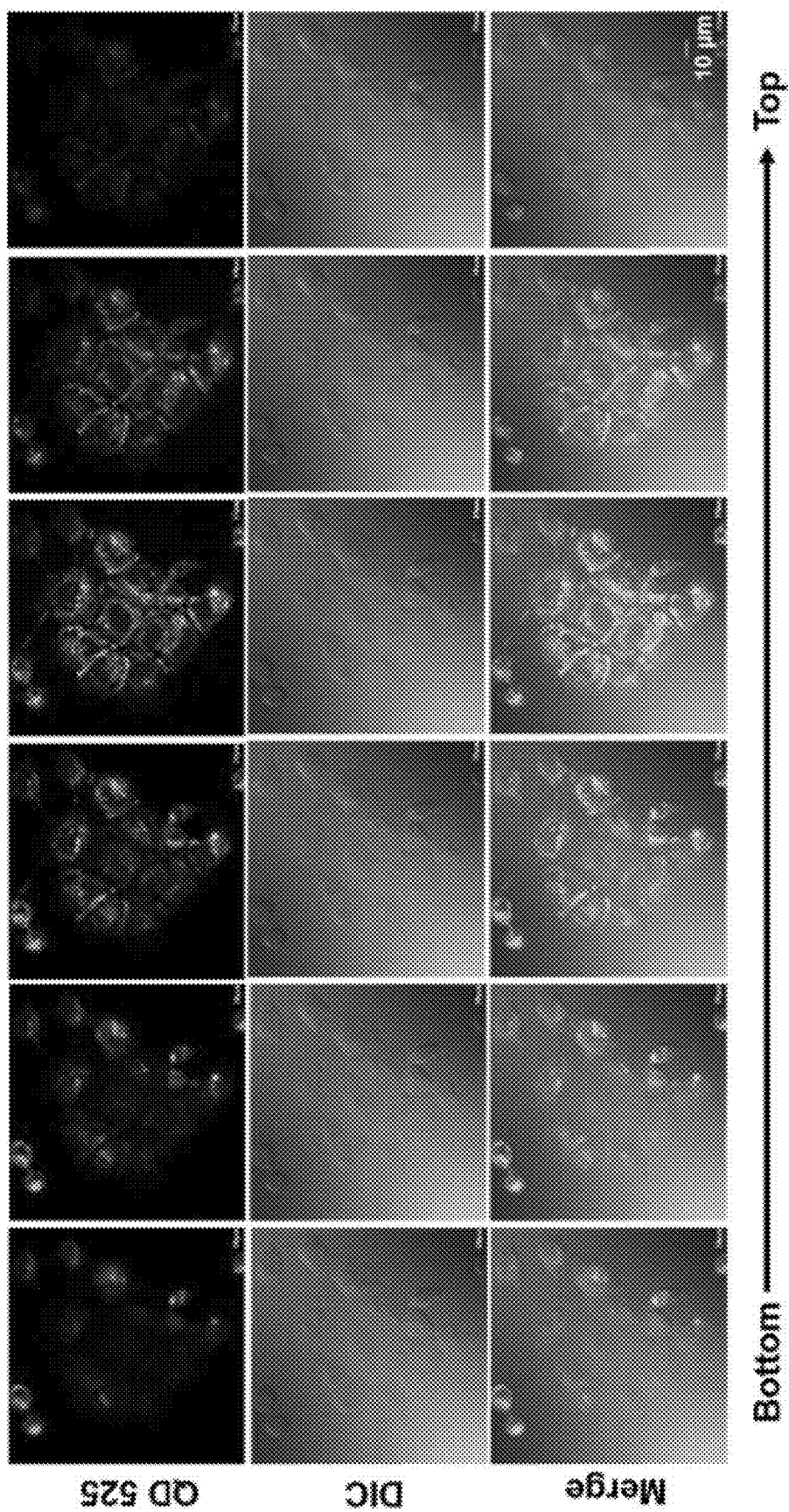

In this example, QDs were conjugated to S-proteins as a fluorescent probe. Confocal Z-stack images showed that most of the QD-S-proteins were internalized by the OEC-M1 cells beginning at 30 min post incubation (as evidenced by the detection of QD fluorescence at the middle scanning layers of the Z dimension in FIG. 14A), while minimal/no QD-S-proteins were detected at the top and bottom layers (FIGS. 14B and 14C). These observations suggest the swift uptake of S-protein by the OEC-M1 cells, likely through its interaction with ACE2 expressed on the cell surface.

(5.4) In Vitro SARS-CoV-2 Infectivity

To examine the effects of the ACEi on SARS-CoV-2 replication, $2 \times 10^5$ ACE2-expressing OEC-M1 cells were pre-treated with the peptide analogs of ACEi, i.e., enalapril, enalaprilat, lisinopril, captopril, perindopril, or ramipril, at 20 µM for 30 min, followed by exposure to 1 multiplicity of infection (MOI) of SARS-CoV-2 (SARS-CoV-2/human/TWN/CGMH-CGU-01/2020) for 1 hour in the presence of the respective peptide analogs of ACEi. A blank control group was also included, whereby the cells received similar treatment but no ACEi was included in the cell culture media. After incubation, all cells were washed with PBS and incubated at 37° C. for another 24 hours.

At the end of the 24-hour incubation, cell culture media were harvested, and SARS-CoV-2 RNA was extracted from the media using LabTurbo Viral Mini Kit with LabTurbo 48 Compact System (LabTurbo, Taipei, Taiwan).

The viral RNA expression was then determined using quantitative real-time PCR, i.e., cDNAs were synthesized using the MMLV Reverse Transcription Kit (Protech, Taipei, Taiwan). The primers and probes were targeted to the envelope protein gene (E gene) of SARS-CoV-2 according to the recommendations by the Taiwan Center for Disease Control (CDC). Primer and probe sequences for E gene of SARS-CoV-2 were as follows:

```
Primer Forward:
                                        (SEQ ID NO: 3)
5'-ACAGGTACGTTAATAGTTAATAGCGT-3';

Primer Reverse:
                                        (SEQ ID NO: 4)
5'-ATATTGCAGCAGTACGCACACA-3';

Probe:
                                        (SEQ ID NO: 5)
5'-FAM-ACACTAGCCATCCTTACTGCGCTTCG-BBQ-3'
```

(FAM: short version for fluorescein; BBQ: BlackBerry Quencher).

Subsequently, Roche Light Cycler 480 System (Roche, Basel, Switzerland) and 2×qPCR BIO Probe Blue Mix Lo-ROX (Kapa Biosystems, Wilmington, MA, USA) were deployed for quantitative detection of nucleic acids.

Figure 15:
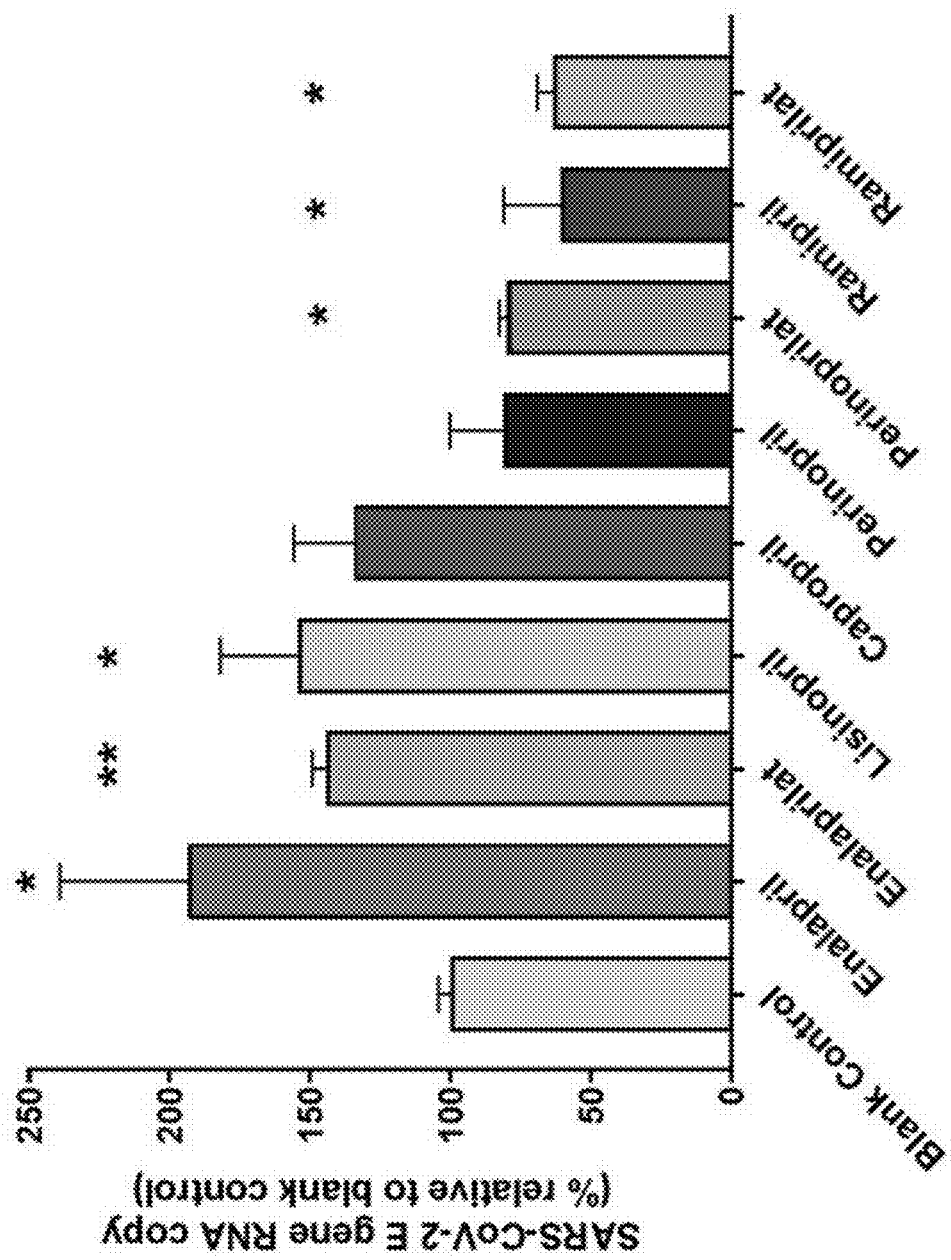
FIG. 15 shows the expression of SARS-CoV-2 E gene RNA in ACE2-expressing OEC-M1 cells pre-treated with the ACEi drugs (relative to blank control, *$p<0.05$, **$p<0.01$, unpaired t-test).

As shown in FIG. 15, upon treatment with ramipril and ramiprilat, E gene RNA copies in the culture media of OEC-M1 cells were reduced by 39.3% and 36.4%, respectively (both $p<0.05$ vs. blank control). In contrast, E gene RNA copies reduced by approximately 18.8% and 20.1% with perindopril and perindoprilat treatments ($p<0.05$ for perindoprilat vs. blank control). On the other hand, E gene RNA was found increased in the media harvested from cells treated with enalapril, enalaprilat and lisinopril (increased by 93.7%, 44.4% and 54.2%, respectively, relative to the blank control, $p<0.05$). Interestingly, the E gene RNA copy for the captopril-treated group was elevated by 34.5%, suggesting possible positive modulation of SARS-CoV-2-ACE2 binding by captopril in vitro. Overall, the findings of this experiment were found to be consistent to that of the above EIS-based biosensing studies, and further suggested the potential use of the developed EIS-based biosensing platform for rapid screening of inhibitors for SARS-CoV-2-ACE2 binding.

Example 6: Stability of SARS-CoV-2 Variant

To compare the stability of two SARS-CoV-2 variants, namely, SARS-CoV-2 variants having spike protein with the D614 mutation (S-D614) and D614G mutation (S-G614), the infectivity of the variants, the integrity of the viral RNA, and the ability of the spike protein to bind ACE2 after storage at refrigeration (4° C.) and freezing (−20° C.) for different periods were determined.

(6.1) Materials and Methods

Cell line: Vero E6 (American Type Culture Collection, Manassas, VA, USA) cells were grown in Dulbecco's modified Eagle's medium (DMEM) containing 10% FBS, 1% antibiotic/antimycotic solution, and 1% L-glutamine (Gibco, Grand Island, NY, USA). The cells were cultured at 37° C. with 5% $CO_2$.

Viruses: The S-D614 SARS-CoV-2/human/TWN/CGMH-CGU-01/2020 (GISAID accession number EPI_ISL_411915; NCBI accession number MT192759.1) and S-G614 SARS-CoV-2/human/TWN/CGMH-CGU-25/2020 (GISAID accession number EPI_ISL_444278; NCBI accession number MT479227.1) variants were originally isolated from a patient with COVID-19 from Chang Gung Memorial Hospital (Taiwan). Viral amplification and manipulation were performed in an accredited biosafety level 3 laboratory at the Chang Gung Memorial Hospital. The S-G614 variant had four synonymous and four nonsynonymous mutations in the coding region. The nonsynonymous mutations include ORF1ab-C794T(T265I), ORF1ab-C14144T(P4715L), S-A1841G(D614G), and ORF3a-G171C(Q57H). There was also a mutation in the 5' untranslated region C241T. The SARS-CoV-2 stocks of the S-D614 and S-G614 variants were diluted in DMEM with 2% FBS at $10^2$ to $10^4$ plaque-forming unit (PFU)/mL and stored at 4° C. and −20° C. for different durations (1, 4, 7, 21, and 30 days). Thereafter, they were transferred to −80° C. until further analyses such as titration, RNA quantification, and RNA integrity analysis. Viruses were propagated in Vero E6 cells, maintained in DMEM with 2% FBS and stored at −80° C. until further study.

Plaque assay: Vero E6 cells were seeded into a six-well cell culture plate and grown for 18 to 24 hours at 37° C. At 90% confluence, the medium was removed, and 10-fold serial viral dilutions (from $10^0$ to $10^{-4}$) were allowed to adsorb onto the cells for 60 min. The cells were washed with PBS and grown in DMEM containing 2% FBS with 0.4% of agarose for 3 days. To visualize the plaques, the cells were inactivated with 10% formalin for at least 1 hour and were then stained with 0.5% crystal violet.

Viral RNA extraction and real-time PCR: Viral RNA was extracted using the LabTurbo Viral DNA/RNA Mini Kit according to the manufacturer's instructions and using the LabTurbo 48 Compact System (Taigen Bioscience, Taipei, Taiwan). The E and nsp12 genes were quantified as described previously[9].

SARS-CoV-2 pseudovirus (nCoV-S Luc pseudovirus/S-D614): The SARS-CoV-2-S Luc pseudovirus (provided by the National RNAi Core Facility, Academia Sinica, Taiwan) uses pCMVdeltaR8.91 and pcDNA3.1 to express the spike protein on the viral surface. The transfer vector pLAS2w.FLuc.Ppuro carried by the virus expressed firefly luciferase.

Recombinant expression and characterization of the human ACE2 protein: Recombinant human angiotensin-converting enzyme 2 (rhACE2) was expressed in the *Escherichia coli* system as described above. rhACE2 refolding was confirmed by western blotting, and its interaction with the SARS-CoV-2 spike protein receptor-binding domain was confirmed by electrochemical impedance spectroscopy measurements as described above.

Statistical analysis: Student's t test was used to compare the results of the viral titer changes between 4° C. and −20° C. on the same day, presented in FIGS. 16B and 16C. The two-way analysis of variance (ANOVA) with Newman-Keuls multiple-comparison test was used to analyze the ACE2-binding ability of the same virus variant at different temperatures and that of different variant viruses at the same temperature. Statistical analysis was performed using GraphPad Prism v9.3.3 (GraphPad Software, Inc., CA, USA). Linear regression models were used to determine the correlation between genome copies of structural (E) and nonstructural genes (nsp12) with $C_T$ values obtained from real-time PCR, and the $R^2$ value was used to assess model fitness. Statistical analysis was conducted using the R software v3.6.1, and the distribution of genome copies and their correlations were visualized using the R package ggplot2 as previously described[9].

Figure 16A:
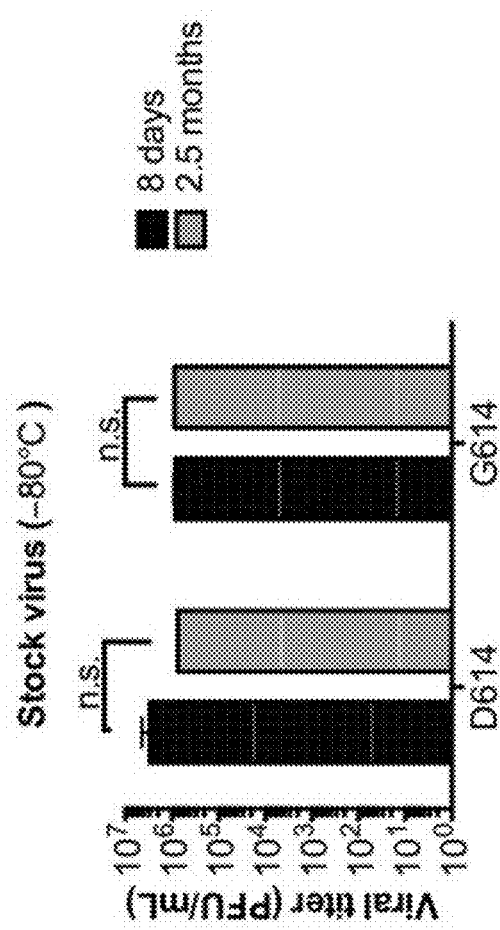
FIGS. 16A to 16G show the titers of SARS-CoV-2 S-D614 and S-G614 variants after storage at 4° C., −20° C., and −80° C. for different durations.

(6.2) Higher Infectivity of the SARS-CoV-2 S-G614 Variant than that of S-D614 after Cold Storage As shown in FIG. 16A, the titers of the SARS-CoV-2 S-D614 and S-G614 variants remained stable after 2.5 months of storage at −80° C. compared with the baseline values (8 days of storage). However, 14 days of storage at 4° C. significantly reduced the titer of the S-D614 variant compared with storage at −20° C. (FIG. 16B). The titers of the S-D614 variant were almost undetectable after 30 days of storage at 4° C. but decreased by only 1 log unit relative to the baseline level (0 days of storage) when stored at −20° C. These findings indicated that the S-D614 variant was more stable at −20° C. than at 4° C.

Figure 16C:
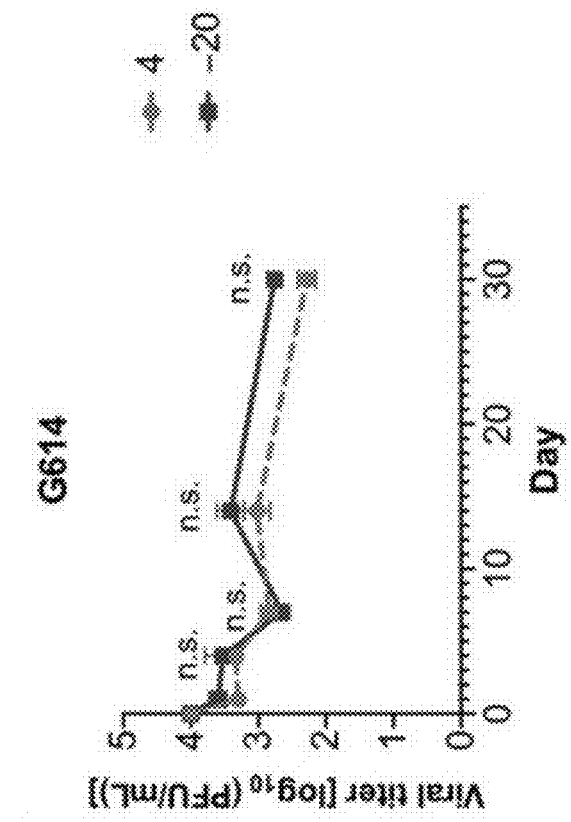
Figure 16B:
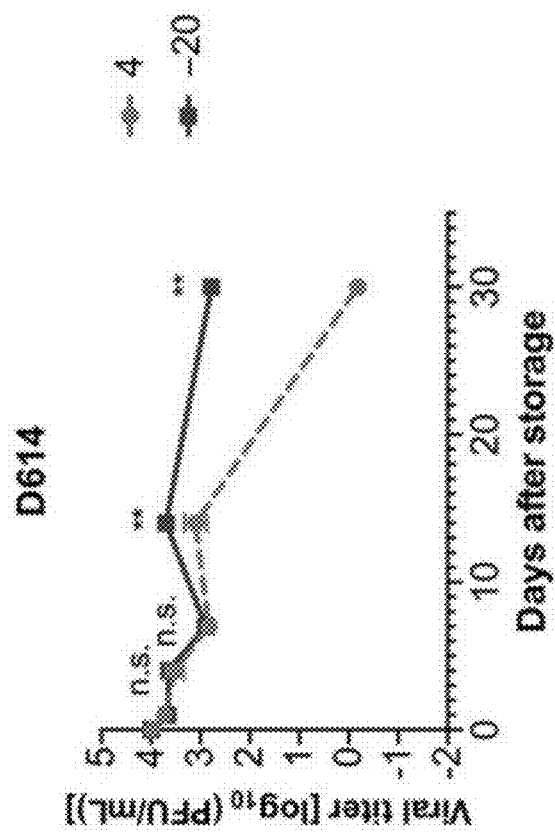

Similarly, the titers of the S-G614 variant decreased approximately 1 log unit compared with the initial titer after storage at −20° C. for 30 days (FIG. 16C). Interestingly, unlike the S-D614 variant, the S-G614 variant retained a considerable degree of infectivity when stored at 4° C. for 30 days (FIG. 16C), suggesting that the stability of the S-G614 variant after 30-day storage at 4° C. and −20° C. was similar.

Figure 16E:
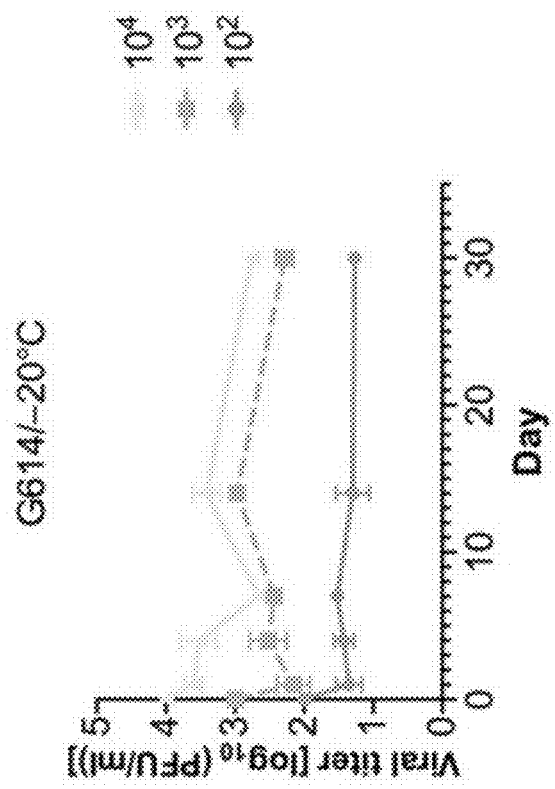
Figure 16D:
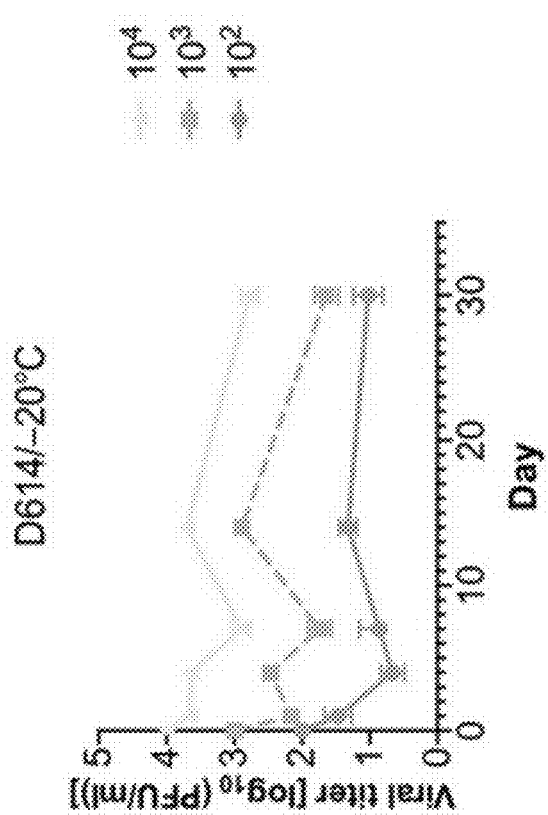
Figure 16G:
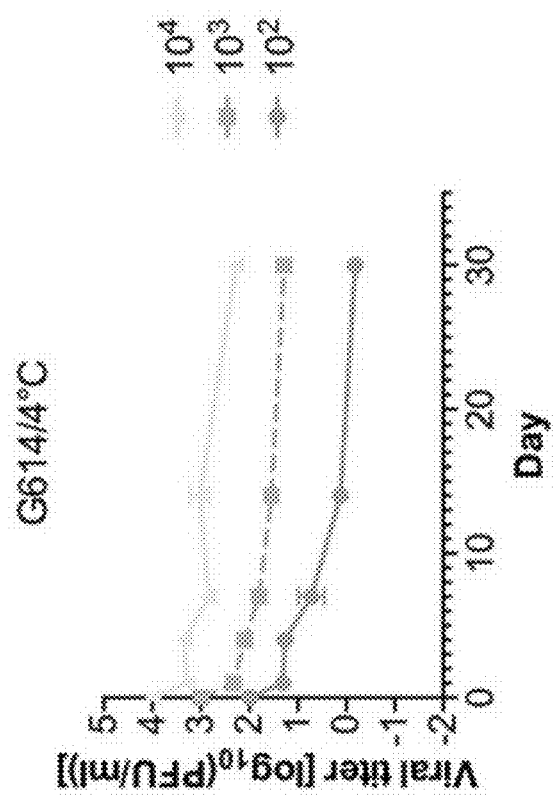
Figure 16F:
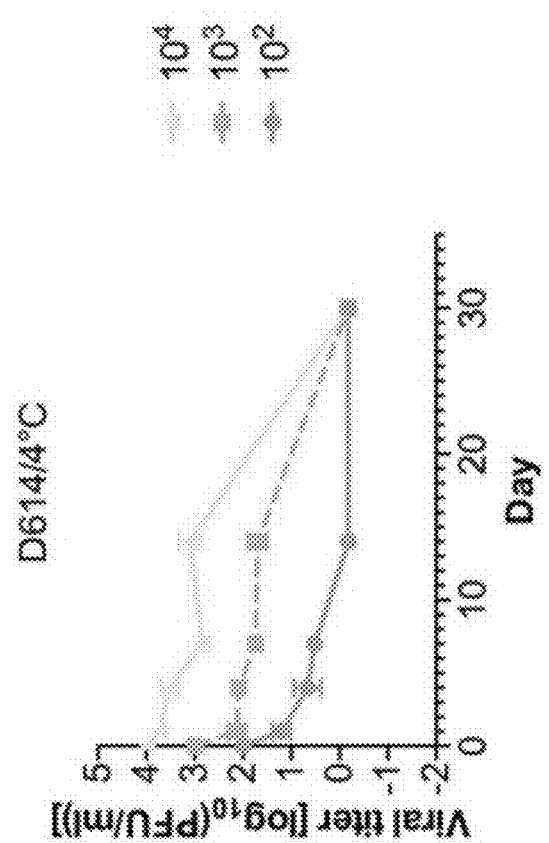

Further, the stability of the variants at low initial viral titers was determined, because the viral concentrations in the environment and on surfaces were typically not as high as that in laboratory cultures. For this purpose, higher initial titers ($10^4$) in FIGS. 16B and 16C were compared with lower initial titers ($10^2$ and $10^3$) as shown in FIGS. 16D to 16G. As a result, S-D614 and S-G614 with both high and low initial titers remained infectious even after 30 days of storage at −20° C. (FIGS. 16D and 16E). However, the S-D614 variant exhibited higher infectivity for a longer duration at high initial viral titers ($10^3$ and $10^4$ PFU/mL) than low initial titers ($10^2$ PFU/mL) at 4° C. (FIGS. 16F and 16G). That is, the relatively stable S-G614 variant with high initial titers remained infectious when stored at 4° C. for 30 days (FIGS. 16F and 16G). These findings indicated that SARS-CoV-2 with low viral titers was less stable at 4° C.

Figure 17A:
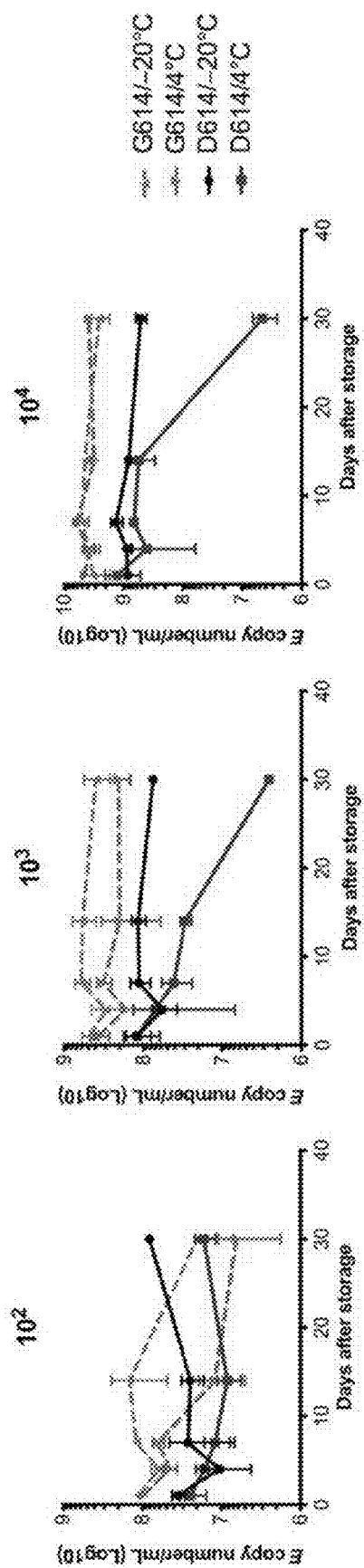
FIGS. 17A and 17B show the RNA copy numbers of the SARS-CoV-2 S-D614 and S-G614 variants stored at 4° C., −20° C., and −80° C. Virus stocks were diluted to $10^2$, $10^3$, and $10^4$ PFU/mL. Viral RNA was extracted, and copy numbers were determined by targeting E (FIG. 17A) and nsp12 (FIG. 17B) genes.
Figure 17B:
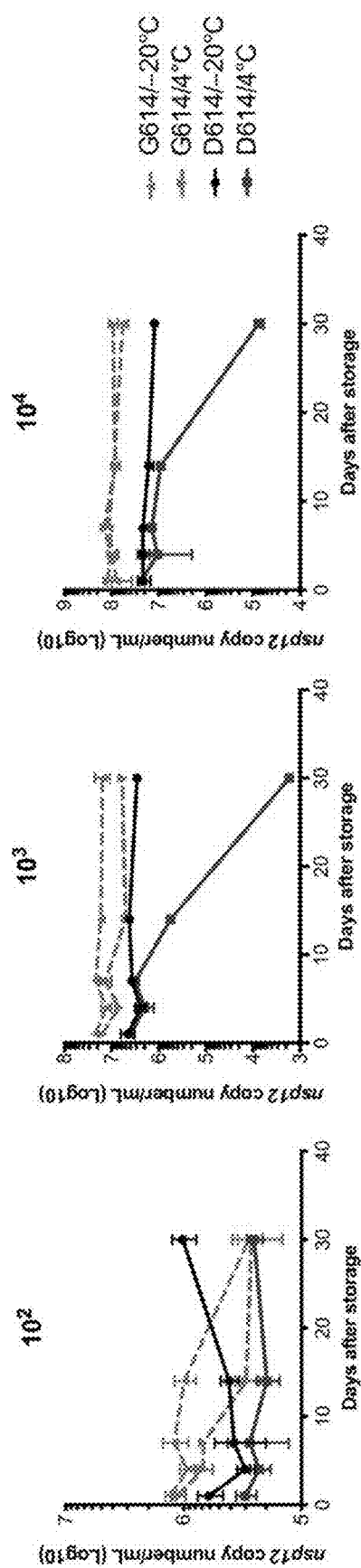

(6.3) Higher RNA Integrity of the SARS-CoV-2 S-G614 Variant than that of S-D614 after Cold Storage The TaqMan probe system was used to quantify the expression of structural E and nonstructural nsp12 genes because degraded viral RNA cannot be amplified and detected. In both E and nsp12 genes (FIGS. 17A and 17B), the trends in the copy numbers of viral RNA from the S-D614 and S-G614 variants were consistent with those of the infectious viral titer, implying that the decrease in viral titer correlated with viral RNA degradation.

Figure 18A:
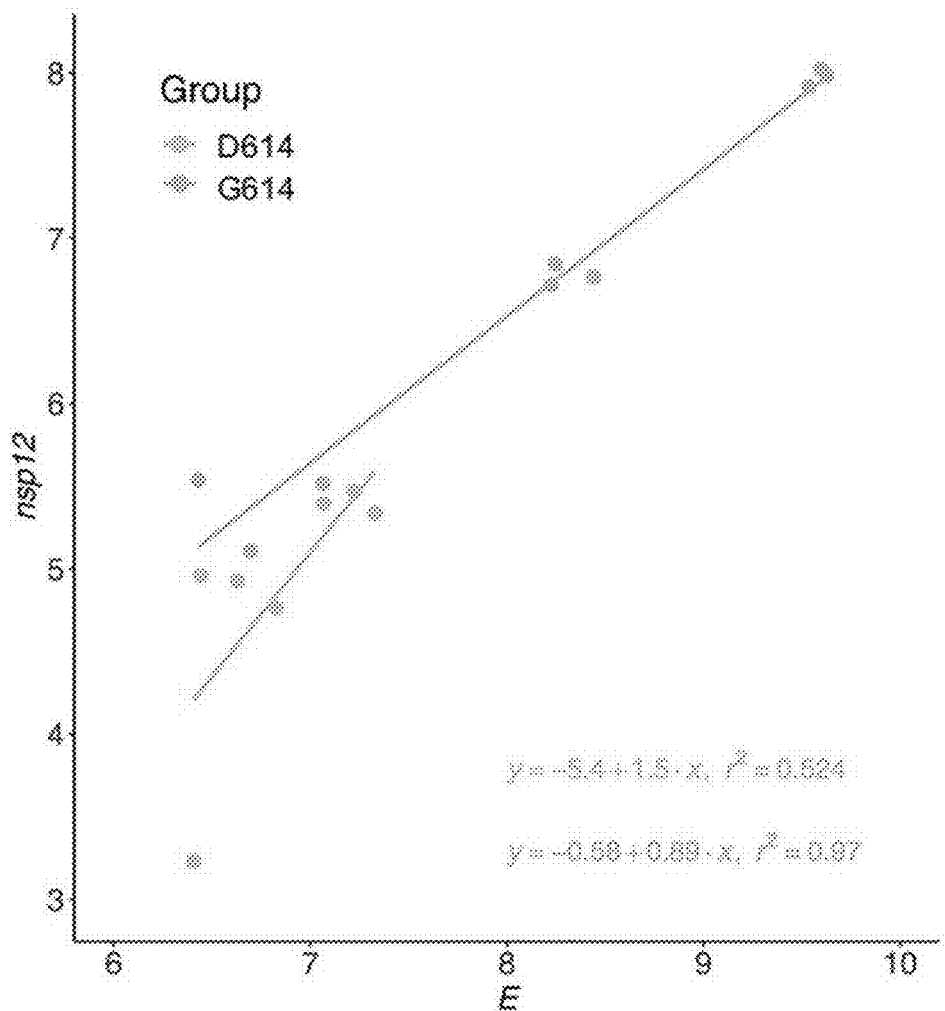
FIGS. 18A and 18B show the correlation between the copy number of nsp12 and E genes in the S-D614 and S-G614 variants of SARS-CoV-2 stored at 4° C.
Figure 18B:
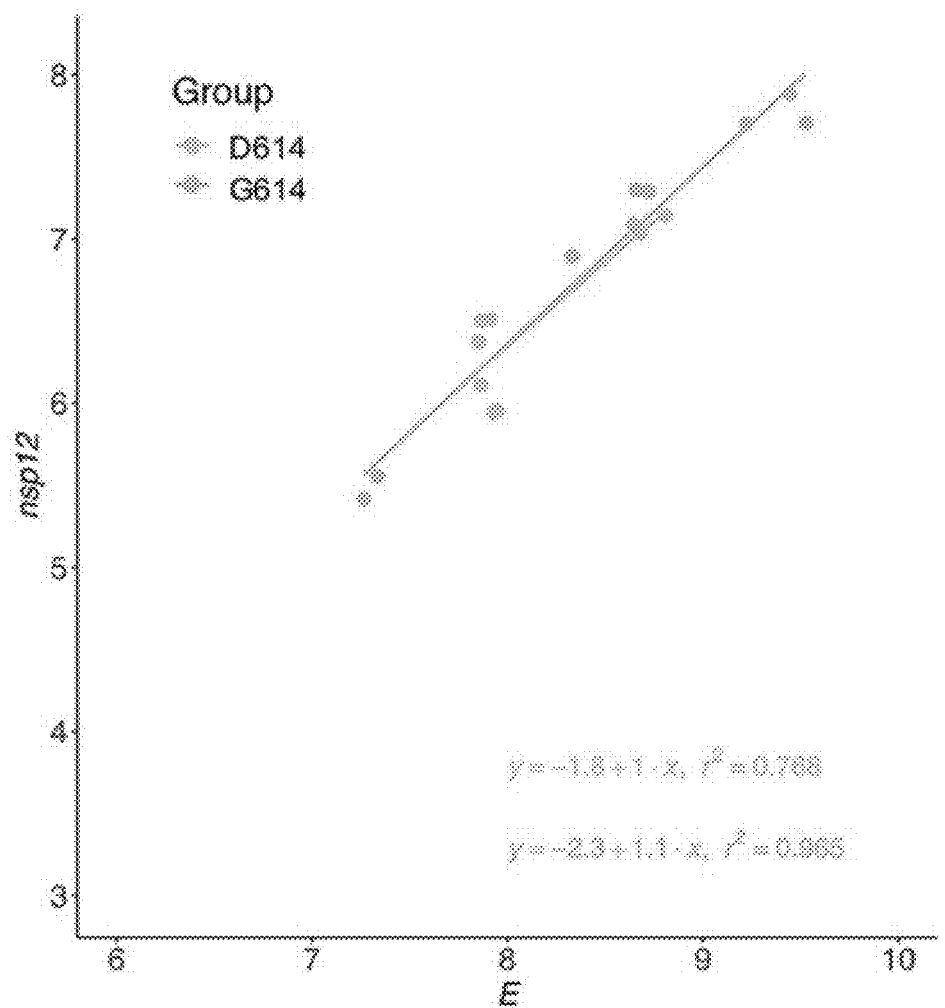

Further, the integrity of SARS-CoV-2 RNA was analyzed by determining the linear relationship between nsp12 and E gene copies. As shown in FIGS. 18A and 18B, the S-G614 variant showed a higher correlation between the E and nsp12 genes than the S-D614 variant after storage at 4° C. (FIG. 18A) and −20° C. (FIG. 18B), indicating that the genome of the S-G614 variant was more stable. Moreover, the correlation between E and nsp12 genes of the S-D614 variant was higher at −20° C. than at 4° C., whereas that in the S-G614 variant was similar at both temperatures. These results were consistent with those observed for viral titers.

Figure 19:
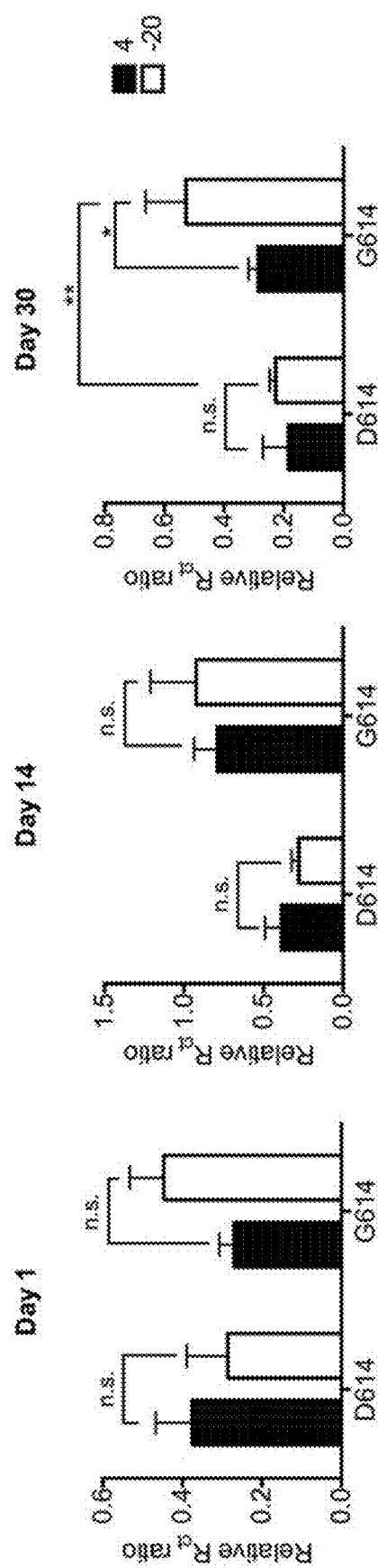
FIG. 19 shows the binding of the SARS-CoV-2 spike protein with recombinant human angiotensin-converting enzyme 2 (rhACE2). Pseudoviruses carrying SARS-CoV-2 S-D614 and S-G614 are stored at −20° C. or 4° C. for different durations, and then added to rhACE2-coated chips. The relative $R_{ct}$ ratio is considered proportional to the amount of spike protein bound to ACE2. Error bars represent standard deviations derived from three independent experiments (*$p<0.05$, **$p<0.01$, ns: not significant).

(6.4) Greater Binding of the SARS-CoV-2 S-G614 Variant to Recombinant Human ACE2 than that of S-D614 after Cold Storage Either S-D614 or S-G614 pseudovirus was added to the chip of Pd-NTFE coated with rhACE2 at equal transduction unit (transduction unit [TU]/μL), and the changes in resistance were observed. FIG. 19 showed that there is no significant difference in the binding ability of the S-D614 and S-G614 pseudoviruses to rhACE2 at different temperatures on the first day. Further, the binding ability of the S-D614 pseudovirus at different temperatures did not significantly change after 30 days of storage. However, after 14 and 30 days, the binding ability of the S-G614 pseudovirus at −20° C. was significantly higher than that at 4° C. Thus, the rhACE2-binding ability of the S-G614 variant on day 30 of storage at −20° C. was significantly higher than that of the S-D614 variant. Moreover, storage at 4° C. was not conducive for the maintenance of the rhACE2-binding ability of both variants, whereas storage at −20° C. better maintained the binding ability of the S-G614 variant compared with that of the S-D614 variant.

From the above, these results reveal that the EIS-based biosensing platform provided herein is capable of identifying both positive and negative modulators of the SARS-CoV-2 S-protein-ACE2 binding. This sensor platform offers sensitive and rapid detection of the binding of modulators to ACE2 in a small sample volume (e.g., 1 μL). With this detection system, the binding of as little as 4 pg or 0.1 μg/mL modulator can be detected. The elevated detection sensitivity of this thin film biosensing platform may be correlated to the enhanced local surface plasmon resonance and electric field (for better Raman signals and EIS detection) on the biosensing electrode by its multi-layered Pd surface nanostructure. Such a Pd nanogranule coating also enables direct immobilization of the recombinant ACE2 to the probes within 20 min, with which the fabrication of the biosensing electrode is greatly accelerated and simplified.

Also, the EIS-based biosensing platform provided herein can be applied in SARS-CoV-2 variant, so as to determine the binding of the SARS-CoV-2 variant to ACE2 and identify modulators against SARS-CoV-2 variants.

Further, these results also reveal that the peptide analogs of the pharmacological ACEi class may modulate the binding of SARS-CoV-2 S-protein to the ACE2 receptor differentially in a dose-dependent manner, depending on their chemical structures; that is, (i) ACEi that possesses a 3-phenylpropyl-glycine moiety, e.g., enalapril/enalaprilat and lisinopril, may positively modulate the S-protein-ACE2 binding, while (ii) the presence of a bulky group of the rigid fused ring in the structure of ACEi (i.e., the cyclopenta[b]pyrrole-2-carboxylic acid moiety for ramipril/ramiprilat, and 1H-indole-2-carboxylic acid moiety for perindopril/perindoprilat) may invert the mode of modulation of ACEi towards the S-protein-ACE2 binding regardless of structural difference at the glycine moiety, allowing them to antagonize the S-protein-ACE2 binding non-competitively.

The positive modulating effects of ACEi may be further enhanced by the presence of a carboxyl terminal at the glycine moiety (e.g., those in enalaprilat and lisinopril), but weaken by the presence of an n-butyl amine ($C_4H_8$—$NH_2$) side chain at L-lysyl moiety in the ACEi core structure (e.g., those in lisinopril). On the other hand, similar glycine-carboxyl terminal was found to enhance the antagonizing effect of ACEi, should the ACEi contain a cyclopenta[b]pyrrole-2-carboxylic acid moiety (e.g., ramiprilat) or 1H-indole-2-carboxylic acid moiety (e.g., perindoprilat).

These findings demonstrate the potential use of the developed EIS-based biosensing platform for rapid screening of modulators for SARS-CoV-2-ACE2 binding. Also, the findings on the attenuation of the ACE2-S-protein binding and SARS-CoV-2 infectivity by ramipril, ramiprilat, perindopril, and perindoprilat may suggest a direction in the development of molecules with a similar bulky group of rigid fused ring structures (e.g., quinapril, benazepril, trandolapril, cilazapril, and moexipril) but devoid of the pharmacological effects of these compounds as adjunctive agents for the treatment of SARS-CoV-2 infection. In addition, the positive modulatory effects of lisinopril, enalapril, and enalaprilat on ACE2-S-protein binding and SARS-CoV-2 infectivity are unexpected and can be of clinical importance, as it may suggest an increased risk for SARS-CoV-2 infection in ACE2-expressing cells of patients who are on these medications.

Hence, the electrochemical biosensing platform of the present disclosure provides a simple, reliable, and rapid approach for the screening of potential inhibitors and modulators of pharmacological ligand-receptor interactions, as well as provides an alternative strategy for antivirus drug discovery, which is useful in accelerating the development of antivirus drugs, so as to control the outbreak of coronavirus. The present disclosure also suggests that not all ACEi are equal and that different ACEi may impose different modes of modulation on SARS-CoV-2 cell uptake and infectivity, thereby assisting in better decision making in the use of ACEi on the COVID-19 patients with hypertension or other cardiovascular diseases.

While some of the embodiments of the present disclosure have been described in detail above, it is, however, possible for those of ordinary skill in the art to make various modifications and changes to the embodiments shown without substantially departing from the teaching and advantages of the present disclosure. Such modifications and changes are encompassed in the scope of the present disclosure as set forth in the appended claims.

REFERENCE

[1] Xu, X.; Chen, P.; Wang J. F.; Feng J.; Zhou, H.; Li, X.; Zhong W.; Hao P., Evolution of the novel coronavirus from the ongoing Wuhan outbreak and modeling of its spike protein for risk of human transmission. Science China Life Sciences 2020, 63, 4.

[2] Zhao, Y.; Zhao, Z.; Wang, Y.; Zhou, Y.; Ma, Y; Zuo, W., Single-cell RNA expression profiling of ACE2, the putative receptor of Wuhan 2019-nCov. bioRxiv 2020, 2020.01.26.919985.

[3] Wan, Y; Shang, J.; Graham, R.; Baric, R. S.; Li, F., Receptor recognition by novel coronavirus from Wuhan: An analysis based on decade-long structural studies of SARS. Journal of Virology 2020, JVI.00127-20.

[4] Sommerstein, R.; Kochen, M. M.; Messerli, F. H.; Grani, C., Coronavirus Disease 2019: Do angiotensin-converting enzyme inhibitors/angiotensin receptor blockers have a biphasic effect? Journal of the American Heart Association 2020, 9 (7), e016509.

[5] Aronson, J. K.; Ferner, R. E., Drugs and the renin-angiotensin system in covid-19. BMJ 2020, 369, m1313.

[6] Messerli, F. H.; Bangalore, S.; Bavishi, C.; Rimoldi, S. F., Angiotensin-converting enzyme inhibitors in hypertension. To use or not to use? 2018, 71 (13), 1474-1482.

[7] Ramanavicius, A.; Finkelsteinas, A.; Cesiulis, H.; Ramanaviciene, A., Electrochemical impedance spectroscopy of polypyrrole based electrochemical immunosensor. Bioelectrochemistry 2010, 79 (1), 11-16.

[8] Liu, X. L.; Peng, C. W.; Chen, C.; Yang, X. Q.; Hu, M. B.; Xia, H. S.; Liu, S. P.; Pang, D. W.; Li, Y., Quantum dots-based double-color imaging of HER2 positive breast cancer invasion. Biochemical and Biophysical Research Communications 2011, 409 (3), 577-582.

[9] Huang, C. G.; Lee, K. M.; Hsiao, M. J.; Yang, S. L.; Huang, P. N.; Gong, Y. N.; Hsieh, T. H.; Huang, P. W.; Lin, Y. J.; Liu, Y. C.; Tsao, K. C.; Shih, S. R., Culture-based virus isolation to evaluate potential infectivity of clinical specimens tested for COVID-19. Journal of Clinical Microbiology 2020, 58 (8), e01068-20.

What is claimed is:

1. A method for screening a modulator of a viral infection, comprising:
   providing a biosensing platform including:
      an insulating support;
      a working electrode formed from an electrically conductive layer deposited on a surface of the insulating support; and
      angiotensin converting enzyme 2 (ACE2) or a fragment thereof coated on the working electrode;
   pretreating the working electrode of the biosensing platform with a modulator candidate;
   contacting the working electrode with a spike protein or a fragment thereof from a virus of interest in absence or presence of the modulator candidate; and
   measuring a level of electrochemical impedance of the working electrode,
   wherein a difference in the level of the electrochemical impedance of the working electrode pretreated with the modulator candidate compared to a reference level indicates the modulator candidate as the modulator capable of altering an interaction of the ACE2 and the spike protein or a variant thereof, thereby modulating the viral infection.

2. The method according to claim 1, wherein the modulator is a compound represented by formula (I) below:

$$\text{(I)}$$

wherein:
   A is absent or a 4- to 6-membered ring optionally substituted with 1 to 5 moieties of deuterium, halo, amino, hydroxyl, $C_{1-6}$ alkyl, or $C_{1-6}$ alkoxy;
   X is NH or $CH_2$;
   R is —SH or —$CHR_2C(=O)OR_1$;
   $R_1$ is H, deuterium, or a substituted or unsubstituted moiety selected from the group consisting of $C_{1-6}$ alkyl, $C_{3-10}$ cycloalkyl, $C_{3-10}$ cycloheteroalkyl, $C_{6-10}$ aryl, and $C_{4-10}$ heteroaryl;
   $R_2$ is a substituted or unsubstituted moiety selected from the group consisting of $C_{1-6}$ alkyl, $C_{2-6}$ alkenyl, $C_{2-6}$ alkynyl, $C_{1-6}$ alkoxy, $C_{2-6}$ alkenyloxy, $C_{1-6}$ alkylcarbonyl, $C_{1-6}$ alkyloxycarbonyl, $C_{1-6}$ alkylamino, $C_{3-20}$ cycloalkyl, $C_{3-20}$ cycloheteroalkyl, $C_{6-20}$ aryl, and $C_{4-20}$ heteroaryl;
   $R_3$ is H, deuterium, halo, cyano, hydroxyl, carboxyl, amino, formyl, nitro, or a substituted or unsubstituted moiety selected from the group consisting of $C_{1-6}$ alkyl, $C_{2-6}$ alkenyl, $C_{2-6}$ alkynyl, $C_{1-6}$ alkoxy, $C_{2-6}$ alkenyloxy, $C_{1-6}$ alkylcarbonyl, $C_{1-6}$ alkyloxycarbonyl, $C_{1-6}$ alkylamino, $C_{3-20}$ cycloalkyl, $C_{3-20}$ cycloheteroalkyl, $C_{6-20}$ aryl, and $C_{4-20}$ heteroaryl;
   $R_4$ is H, deuterium, amino, halo, hydroxyl, or a substituted or unsubstituted moiety selected from the group consisting of $C_{1-6}$ alkyl and $C_{1-6}$ alkoxy;
   $R_5$ is H, deuterium, or a substituted or unsubstituted moiety of $C_{1-6}$ alkyl; and
   m is an integer of 1 to 4.

3. The method according to claim 1, wherein the modulator is an angiotensin-converting enzyme (ACE) inhibitor.

4. The method according to claim 1, wherein the virus is a coronavirus selected from severe acute respiratory syndrome coronavirus (SARS-CoV), Middle East respiratory syndrome coronavirus (MERS-CoV), SARS-CoV-2, mouse hepatitis virus (MHV), porcine epidemic diarrhea virus (PEDV), and a variant thereof.

5. A method for protecting a subject from a viral infection, comprising administering to the subject an effective amount of the modulator screened by the method of claim 1.

6. The method according to claim 5, wherein the modulator is a compound represented by formula (II) below:

$$\text{(II)}$$

wherein:
   $R_1$ is H, deuterium, or a substituted or unsubstituted moiety selected from the group consisting of $C_{1-6}$ alkyl, $C_{3-10}$ cycloalkyl, $C_{3-10}$ cycloheteroalkyl, $C_{6-10}$ aryl, and $C_{4-10}$ heteroaryl;
   $R_2$ is a substituted or unsubstituted moiety selected from the group consisting of $C_{1-6}$ alkyl, $C_{2-6}$ alkenyl, $C_{2-6}$ alkynyl, $C_{1-6}$ alkoxy, $C_{2-6}$ alkenyloxy, $C_{1-6}$ alkylcarbonyl, $C_{1-6}$ alkyloxycarbonyl, $C_{1-6}$ alkylamino, $C_{3-20}$ cycloalkyl, $C_{3-20}$ cycloheteroalkyl, $C_{6-20}$ aryl, and $C_{4-20}$ heteroaryl;
   $R_3$ is H, deuterium, halo, cyano, hydroxyl, carboxyl, amino, formyl, nitro, or a substituted or unsubstituted moiety selected from the group consisting of $C_{1-6}$ alkyl, $C_{2-6}$ alkenyl, $C_{2-6}$ alkynyl, $C_{1-6}$ alkoxy, $C_{2-6}$ alkenyloxy, $C_{1-6}$ alkylcarbonyl, $C_{1-6}$ alkyloxycarbonyl, $C_{1-6}$ alkylamino, $C_{3-20}$ cycloalkyl, $C_{3-20}$ cycloheteroalkyl, $C_{6-20}$ aryl, and $C_{4-20}$ heteroaryl;
   $R_4$ is H, deuterium, amino, halo, hydroxyl, or a substituted or unsubstituted moiety selected from the group consisting of $C_{1-6}$ alkyl and $C_{1-6}$ alkoxy;
   $R_5$ is H, deuterium, or a substituted or unsubstituted moiety of $C_{1-6}$ alkyl;
   n is 0, 1 or 2;
   m is an integer of 1 to 4; and
   wherein the protecting is inhibition of infectivity of the virus in the subject.

7. The method according to claim 6, wherein the substituted moiety consists of the moiety and one or more substituents selected from the group consisting of deuterium, alkyl, alkenyl, alkynyl, hydroxyalkyl, fluoroalkyl, chloroalkyl, bromoalkyl, iodoalkyl, perfluoroalkyl, aryl, heteroaryl, cycloalkyl, cycloalkenyl, cycloheteroalkyl, carboxyl, aralkyl, aralkenyl, aralkynyl, heteroaralkyl, heteroaralkenyl, heteroaralkynyl, heterocyclyl, acyl, aminocarbonyl, aminoalkyl, amino, alkylamino, hydroxyl, alkoxy, aryloxy, silyloxy, amido, imidoyl, carbamoyl, halo, cyano, nitro, phosphate group, thio, thioether, sulfo, and sulfamido.

8. The method according to claim 6, wherein:
R$_1$ is H or C$_{1-6}$ alkyl optionally substituted with 1 to 5 moieties of deuterium, halo, amino, hydroxyl, C$_{1-6}$ alkyl, or C$_{1-6}$ alkoxy;
R$_2$ is C$_{1-6}$ alkyl, C$_{1-6}$ alkoxy, C$_{1-6}$ alkylamino, C$_{3-20}$ cycloalkyl, C$_{3-20}$ cycloheteroalkyl, C$_{6-20}$ aryl, or C$_{4-20}$ heteroaryl, wherein C$_{1-6}$ alkyl, C$_{1-6}$ alkoxy, C$_{1-6}$ alkylamino, C$_{3-20}$ cycloalkyl, C$_{3-20}$ cycloheteroalkyl, C$_{6-20}$ aryl, or C$_{4-20}$ heteroaryl is optionally substituted with 1 to 5 moieties of deuterium, halo, amino, hydroxyl, C$_{1-6}$ alkyl, C$_{1-6}$ alkoxy, C$_{3-10}$ cycloalkyl, C$_{3-10}$ cycloheteroalkyl, C$_{6-10}$ aryl, or C$_{4-10}$ heteroaryl;
R$_3$ is C$_{1-6}$ alkyl, C$_{2-6}$ alkenyl, C$_{2-6}$ alkynyl, C$_{1-6}$ alkoxy, C$_{2-6}$ alkenyloxy, C$_{1-6}$ alkylcarbonyl, C$_{1-6}$ alkyloxycarbonyl, or C$_{1-6}$ alkylamino, wherein C$_{1-6}$ alkyl, C$_{2-6}$ alkenyl, C$_{2-6}$ alkynyl, C$_{1-6}$ alkoxy, C$_{2-6}$ alkenyloxy, C$_{1-6}$ alkylcarbonyl, C$_{1-6}$ alkyloxycarbonyl, or C$_{1-6}$ alkylamino is optionally substituted with 1 to 5 moieties of deuterium, halo, hydroxyl, cyano, amino, nitro, carboxyl, C$_{1-6}$ alkyl, C$_{1-6}$ alkoxy, or C$_{1-6}$ alkylamino;
R$_4$ is H, halo, C$_{1-6}$ alkyl or C$_{1-6}$ alkoxy, wherein C$_{1-6}$ alkyl or C$_{1-6}$ alkoxy is optionally substituted with 1 to 5 moieties of deuterium, halo or hydroxyl; and
R$_5$ is H or C$_{1-6}$ alkyl optionally substituted with 1 to 5 moieties of deuterium, halo, amino, hydroxyl, C$_{1-6}$ alkyl, or C$_{1-6}$ alkoxy.

9. The method according to claim 8, wherein:
R$_1$ is H or an unsubstituted C$_{1-6}$ alkyl;
R$_2$ is C$_{1-6}$ alkyl optionally substituted with 1 to 5 moieties of C$_{1-6}$ alkyl, C$_{3-10}$ cycloalkyl, C$_{3-10}$ cycloheteroalkyl, C$_{6-10}$ aryl, or C$_{4-10}$ heteroaryl;
R$_3$ is C$_{1-6}$ alkyl optionally substituted with 1 to 5 moieties of deuterium, halo, hydroxyl, cyano, amino, nitro, carboxyl, C$_{1-6}$ alkyl, C$_{1-6}$ alkoxy, or C$_{1-6}$ alkylamino;
R$_4$ and R$_5$ are H; and
n is 1 or 2.

10. The method according to claim 9, wherein:
R$_1$ is H, methyl, ethyl, or propyl;
R$_2$ is methyl, ethyl, propyl, or benzyl; and
R$_3$ is methyl, ethyl, propyl, n-butyl, or n-butylamine.

11. The method according to claim 6, wherein the modulator is formulated into an antiviral medicine for administration.

12. The method according to claim 5, wherein the modulator is a compound represented by formula (III) below:

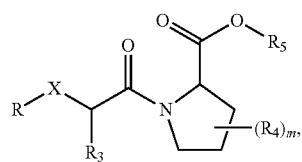

(III)

wherein:
X is NH or CH$_2$;
R is —SH or —CHR$_2$C(=O)OR$_1$;
R$_1$ is H or an unsubstituted C$_{1-6}$ alkyl;
R$_2$ is C$_{1-6}$ alkyl optionally substituted with 1 to 5 moieties of C$_{1-6}$ alkyl, C$_{3-10}$ cycloalkyl, C$_{3-10}$ cycloheteroalkyl, C$_{6-10}$ aryl, or C$_{4-10}$ heteroaryl;
R$_3$ is C$_{1-6}$ alkyl optionally substituted with 1 to 5 moieties of deuterium, halo, hydroxyl, cyano, amino, nitro, carboxyl, C$_{1-6}$ alkyl, C$_{1-6}$ alkoxy, or C$_{1-6}$ alkylamino;
R$_4$ is H, deuterium, amino, halo, hydroxyl, or a substituted or unsubstituted moiety selected from the group consisting of C$_{1-6}$ alkyl and C$_{1-6}$ alkoxy;
R$_5$ is H, deuterium, or a substituted or unsubstituted moiety of C$_{1-6}$ alkyl; and
wherein the protecting induces an immune response against the virus in the subject.

13. The method according to claim 12, wherein the modulator is formulated into a vaccine composition for administration.

14. The method according to claim 5, wherein the modulator is selected from the group consisting of:

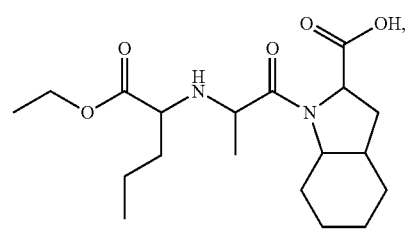

perindopril

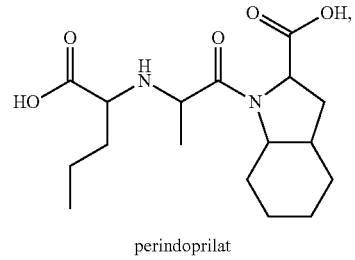

perindoprilat

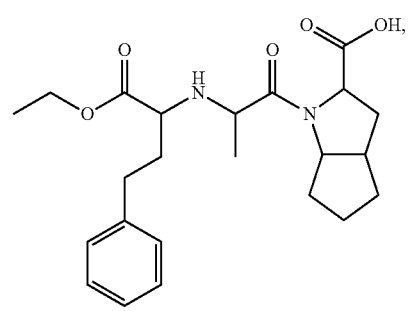

ramipril

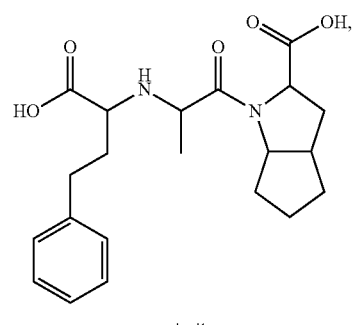

ramiprilat

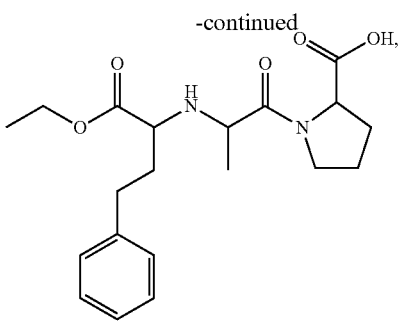
enalapril

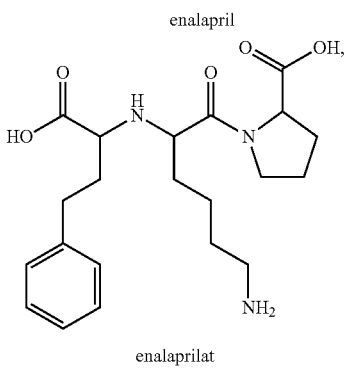
enalaprilat

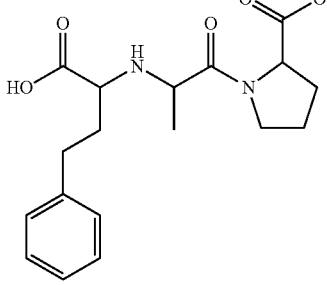
lisinopril

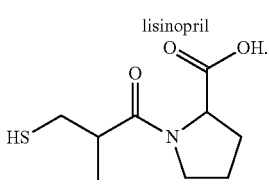
captopril

15. The method according to claim 5, wherein the viral infection is caused by a coronavirus.

16. The method according to claim 15, wherein the coronavirus is severe acute respiratory syndrome coronavirus (SARS-CoV), Middle East respiratory syndrome coronavirus (MERS-CoV), SARS-CoV-2, mouse hepatitis virus (MHV), porcine epidemic diarrhea virus (PEDV), or a variant thereof.

17. The method according to claim 5, wherein the subject is suffering from hypertension or a cardiovascular disease, and/or at a risk of developing the viral infection.

18. A biosensing platform for detecting a viral infection in a subject, comprising:
   an insulating support;
   a working electrode formed from an electrically conductive layer deposited on a surface of the insulating support;
   angiotensin converting enzyme 2 (ACE2) coated on the working electrode; and
   a compound binding to the ACE2, wherein the compound is represented by formula (III) below:

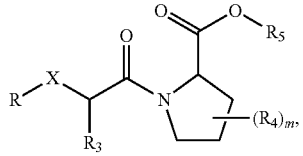

(III)

wherein:
   X is NH or $CH_2$;
   R is —SH or —$CHR_2C(=O)OR_1$;
   $R_1$ is H or an unsubstituted $C_{1-6}$ alkyl;
   $R_2$ is $C_{1-6}$ alkyl optionally substituted with 1 to 5 moieties of $C_{1-6}$ alkyl, $C_{3-10}$ cycloalkyl, $C_{3-10}$ cycloheteroalkyl, $C_{6-10}$ aryl, or $C_{4-10}$ heteroaryl;
   $R_3$ is $C_{1-6}$ alkyl optionally substituted with 1 to 5 moieties of deuterium, halo, hydroxyl, cyano, amino, nitro, carboxyl, $C_{1-6}$ alkyl, $C_{1-6}$ alkoxy, or $C_{1-6}$ alkylamino;
   $R_4$ is H, deuterium, amino, halo, hydroxyl, or a substituted or unsubstituted moiety selected from the group consisting of $C_{1-6}$ alkyl and $C_{1-6}$ alkoxy;
   $R_5$ is H, deuterium, or a substituted or unsubstituted moiety of $C_{1-6}$ alkyl; and
   m is an integer of 1 to 4.

19. The biosensing platform according to claim 18, wherein the electrically conductive layer is composed of palladium, platinum, gold, ruthenium, silver, copper, nickel, indium tin oxide (ITO) or any combination thereof.

20. The biosensing platform according to claim 18, wherein the compound represented by formula (III) is enalapril, enalaprilat, lisinopril, or captopril.

* * * * *